US011717547B2

(12) United States Patent
Krishnan et al.

(10) Patent No.: US 11,717,547 B2
(45) Date of Patent: *Aug. 8, 2023

(54) COMPOSITIONS AND METHODS FOR THE TREATMENT OF AUTOSOMAL RECESSIVE CONGENITAL ICHTHYOSIS

(71) Applicant: Krystal Biotech, inc., Pittsburgh, PA (US)

(72) Inventors: Suma Krishnan, San Francisco, CA (US); Pooja Agarwal, Mars, PA (US); John C. Freedman, Pittsburgh, PA (US); Mark E. O'Malley, Pittsburgh, PA (US); Lauren K. Regula, Pittsburgh, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 663 days.

This patent is subject to a terminal disclaimer.

(21) Appl. No.: 16/734,156

(22) Filed: Jan. 3, 2020

(65) Prior Publication Data

US 2020/0197456 A1 Jun. 25, 2020

Related U.S. Application Data

(63) Continuation of application No. 16/381,557, filed on Apr. 11, 2019, now Pat. No. 10,525,090.

(60) Provisional application No. 62/656,768, filed on Apr. 12, 2018.

(51) Int. Cl.
| | | |
|---|---|---|
| A61K 35/763 | (2015.01) | |
| A61K 9/00 | (2006.01) | |
| A61P 17/00 | (2006.01) | |
| C12N 15/52 | (2006.01) | |
| C12N 15/86 | (2006.01) | |

(52) U.S. Cl.
CPC .......... *A61K 35/763* (2013.01); *A61K 9/0014* (2013.01); *A61P 17/00* (2018.01); *C12N 15/52* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 5,658,724 A | 8/1997 | Deluca et al. | |
| 5,672,344 A | 9/1997 | Kelley et al. | |
| 5,998,174 A | 12/1999 | Glorioso et al. | |
| 6,106,826 A | 8/2000 | Brandt et al. | |
| 6,719,982 B1 | 4/2004 | Coffin | |
| 6,846,670 B2 | 1/2005 | Schwartz | |
| 6,887,490 B1 | 5/2005 | Jahoda et al. | |
| 7,531,167 B2 | 5/2009 | Glorioso et al. | |
| 9,314,505 B2 | 4/2016 | Wise et al. | |
| 9,877,990 B2 | 1/2018 | Krishnan et al. | |
| 10,155,016 B2 | 12/2018 | Krishnan et al. | |
| 10,174,341 B2 | 1/2019 | Glorioso et al. | |
| 10,441,614 B2 | 10/2019 | Krishnan et al. | |
| 10,525,090 B2 | 1/2020 | Krishnan et al. | |
| 11,185,564 B2 | 11/2021 | Krishnan et al. | |
| 2003/0082142 A1 | 5/2003 | Coffin et al. | |
| 2004/0253606 A1 | 12/2004 | Aziz et al. | |
| 2008/0299182 A1 | 12/2008 | Zhang | |
| 2011/0212530 A1 | 9/2011 | Baltimore et al. | |
| 2013/0331547 A1 | 12/2013 | Hall et al. | |
| 2014/0256798 A1 | 9/2014 | Osborn et al. | |
| 2014/0288155 A1 | 9/2014 | Hovnanian et al. | |
| 2014/0341877 A1 | 11/2014 | Kolattukudy | |
| 2015/0038556 A1 | 2/2015 | Heartlein et al. | |
| 2015/0352191 A1 | 12/2015 | South et al. | |
| 2016/0153000 A1 | 6/2016 | Glorioso | |
| 2016/0324934 A1 | 11/2016 | Angel et al. | |
| 2017/0096684 A1 | 4/2017 | Alton et al. | |
| 2017/0290866 A1 | 10/2017 | Krishnan et al. | |
| 2019/0160122 A1 | 5/2019 | Krishnan et al. | |
| 2019/0276845 A1 | 9/2019 | Glorioso et al. | |
| 2019/0328644 A1 | 10/2019 | Krishnan et al. | |
| 2020/0101123 A1 | 4/2020 | Krishnan et al. | |
| 2020/0199618 A1 | 6/2020 | Krisky et al. | |

FOREIGN PATENT DOCUMENTS

| | | |
|---|---|---|
| CN | 102 212 559 | 4/2014 |
| EP | 3377637 | 9/2018 |
| WO | WO 1999/064094 | 12/1999 |
| WO | WO 2000/040734 | 7/2000 |
| WO | WO 2002/064827 | 8/2002 |
| WO | WO 2013/121202 | 8/2013 |
| WO | WO 2015/009952 | 1/2015 |
| WO | WO 2015/117021 | 8/2015 |

(Continued)

OTHER PUBLICATIONS

Manservigi, et al. (2010) "HSV Recombinant Vectors for Gene Therapy", 4: 123-56. (Year: 2010).*
Petermann, et al. (2014) "Entry Mechanisms of Herpes Simplex Virus 1 into Murine Epidermis: Involvement of Nectin-1 and Herpesvirus Entry mediator as Cellular Receptors", Journal of Virology, 89(1): 262-74. (Year: 2014).*
Watanabe (2010) "Medical application of herpes simplex virus", Journal of Dermatological Science, 57: 75-82. (Year: 2010).*
Armstrong, M. "Krystal gets a flying start in epidermolysis bullosa gene therapy" Vantage. Oct. 17, 2018.
Armstrong, M. "Krystal gets more skin in the epidermolysis bullosa game." Vantage. Mar. 5, 2019.

(Continued)

*Primary Examiner* — Robert M Kelly
(74) *Attorney, Agent, or Firm* — Morrison & Foerster LLP

(57) ABSTRACT

The present disclosure provides recombinant nucleic acids comprising one or more polynucleotides encoding a transglutaminase (TGM) polypeptide (e.g., a Transglutaminase-1 (TGM1) polypeptide); viruses comprising the recombinant nucleic acids; compositions comprising the recombinant nucleic acids and/or viruses; methods of their use; and articles of manufacture or kits thereof.

21 Claims, 19 Drawing Sheets

Specification includes a Sequence Listing.

(56) References Cited

FOREIGN PATENT DOCUMENTS

| WO | WO 2017/165806 | 9/2017 |
|---|---|---|
| WO | WO 2017/165813 | 9/2017 |
| WO | WO 2017/176336 | 10/2017 |
| WO | WO 2019/200163 | 10/2019 |
| WO | WO 2021/046131 | 3/2021 |

OTHER PUBLICATIONS

Clinicaltriais.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Ciinicaitrials.gov. NCT04047732: Topical KB105 Gene Therapy for the reatment of TGM1-deficient Autosonnal Recessive Congenital Ichthyosis (ARCI). Aug. 7, 2019.

Clinicaltrials.gov. NCT04214002: The Natural History of Wounds in Patients with Dystrophic Epidermolysis Bullosa (DEB). Dec. 30, 2019.

Goins et al. "Engineering HSV-1 Vectors for Gene Therapy," Methods Mol Biol (2014) 1144: 63-79.

Kopecki et al., "Commentary: New advances in the development of therapies for treating inherited skin fragility disorders," Wound Practice and Research (2015) 23(4): 184.

Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.

Shen et al., "Herpes simplex virus 1 (HSV-1) for cancer treatment," Cancer Gene Therapy (2006) 13: 975-992.

Eming et al., "Gene transfer in tissue repair: status, challenges and future directions," Exp Opin Biol Ther (2004) 4(9):1373-1386.

Freedman et al., "379 KB105: An HSV-based gene therapy vector engineered to deliver functional TGMI to autosomal recessive congenital ichthyosis (ARCI) keratinocytes," J Invest Derm (2019) 139(5):s65 abstract.

Freedman et al., "379 KB105: An HSV-based gene therapy vector engineered to deliver functional TGMI to autosomal recessive congenital ichthyosis (ARCI) keratinocytes," Presentation; Retrieved from https://ir.krystalbio.com/static-files/6e96b265-4cfl-4261-9940-1bcc2aa6f87f, May 2019.

Kohlhapp et al., Molecular Pathways: Mechanism of Action for Talimogene Laherparepvec, a New Oncolytic Virus Immunotherapy, Clinical Cancer Research (2015) 22(5):1048-1054.

Krisky et al., "Development of herpes simplex virus replication-defective multigene vectors for combination gene therapy applications," Gene Ther (1998) 5(110):1517-1530.

Ma et al., "Efficacy of Herpes Simplex Virus Vector Encoding V the Human Preproenkephalin Gene for Treatment of Facial Pain in Mice," J aral Facial Pain Headachce (2016) 30(1):42-50.

Marconi et al., "Replication-defective herpes simplex virus vectors for gene transfer in vivo," Proc Natl Acad Sci USA (1996) 93:11319-11320.

Miyagawa et al., "Herpes simplex viral-vector design for efficient transfuction of nonneuronal cells without cytotoxcity," Proc Natl Acad Sci USA (2015) 112(13):E1632-E1641.

Theopold et al., "A novel replication-defective HSV-1 vector for regulatable gene delivery to wounds," Journal of the American College of Surgeons (2004) 199(3):57-58.

Zhang et al., "383 preclinical safety and pharmacology of KB105, an HSV-based gene therapy vector for the treatment of autosomal recessive congenital ichthyosis (ARCI)," J Invest Derm (2019) 139(5):s66 Abstract.

Zhang et al., "383 preclinical safety and pharmacology of KB105, an HSV-based gene therapy vector for the treatment of autosomal recessive congenital ichthyosis (ARCI)," Presentation; Retrieved from https://ir.krystalbio.com/static-files /e7e6c810-88e9-4702-af94-e5b232e2eb6a, May 2019.

Akiyama et al., "An update on molecular aspects of the non-syndromic ichthyoses," Experimental Dermatology (2008) 17:373-382.

Akiyama et al., "Mutations in lipid transporter ABCA12 in harlequin ichthyosis and functional recovery by corrective gene transfer," J Clin Invest (2005) 115(7):1777-1784.

Akiyama et al., "Updated molecular genetics and pathogenesis of ichthyoses," Nagoya J Med Sci (2011) 73:79-90.

Aldawsari et al., "Progress in Topical siRNA Delivery Approaches for Skin Disorders," Curr Pharm Des. 2015;21 (31):4594-605.

Andtbacka et al., "Talimogene Laherparepvec Improves Durable Response Rate in Patients With Advanced Melanoma," J Clin Oncol. Sep. 1, 2015;33(25):2780-8.

Aufenvenne et al., "Long-term faithful recapitulation of transglutaminase 1-deficient lamellar ichthyosis in a skin-humanized mouse model and insights from proteomic studies," J Invest Dermatol (2012) 132(7):1918.

Aufenvenne et al., "Topical enzyme-replacement therapy restores transglutaminase 1 activity and corrects architecture of transglutaminase-1-deficient skin grafts," The American Journal of Human Genetics (2013) 93:620-630.

Bale et al., "The genetics of ichtyhosis: A primer for epidemiologists," The Journal of Investigative Dermatology (1994) 102(6):49S-50S.

Bastian et al., "Herpes simplex virus type 1 immediate-early protein ICP22 is required for Vice domain formation during productive viral infection." J Viral. Mar. 2010;84(5):2384-94. doi 10.1128/JVI.01686-09. Epub Dec. 23, 2009.

Bubna et al., "A case of lamellar ichthyosis with rickets and carcinoma of the hypopharynx," Indian J Dermatol (2014) 59(6):634.

Burton EA, Fink DJ, Glorioso JC. Gene delivery using herpes simplex virus vectors. DNA Cell Biol. Dec. 2002;21(12):915-36.

Candi et al., "The cornified envelope: A model of cell death in the skin," Nature Review Molecular Cell Biology (2005) 6:328-340.

Casal et al., "A defect in NIPAL4 is associated with autosomal recessive congenital ichtyosis in American bulldogs," PLOS One 12(1) e0170708, year: 2017.

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.

Choate et al., "Corrective gene transfer in the human skin disorder lamellar ichthyosis," Nature Medicine (1996) 2(11):1263-1267.

Choate et al., "Transglutaminase 1 delivery to lamellar ichthyosis keratinocytes," Human Gene Therapy (1996) 7:2247-2253.

Christiano AM. Collagen, type VII, alpha 1 (epidermolysis bullosa, dystrophic, dominant and recessive) [Homo sapiens]. NCBI Reference Sequence: NP_000085.1. Dep. Mar. 19, 1999.

Chung et al., "Expedient treatment of a collodion baby," Case Reports in Dermatological Medicine (2011) vol. 2011, article ID 803782.

Communication pursuant to Article 94(3) EPC for EP 16826873.8, dated Apr. 17, 2019, 7 pages.

Craiglow et al., "Ichthyosis in the newborn," Semin Perinatol (2013) 37(1):26-31.

Credille et al., "Transglutaminase 1-deficient recessive lamellar ichthyosis associated with a LINE-1 insertion in Jack Russell terrier dogs," British Journal of Dermatology (2009) 161:265-272.

Dahlqvist et al., "Congenital ichthyosis: mutations in ichthyin are associated with specifc structural abnormalities in the granular layer of epidermis," J Med Genet (2007) 44:615-620.

Deffenbacher, "Successful experimental treatment of congenital ichthyosis in an infant," BMJ Case Rep (2013) doi:10.1136/bcr-2013-008688.

Deluca et al., "Isolation and Characterization of Deletion Mutants of Herpes Simplex Virus Type 1 in the Gene Encoding Immediate-Early Regulatory Protein ICP4", Journal Of Virology, vol. 56, No. 2, Nov. 1985, pp. 558-570.

Digiovanna et al., "Systemic retinoids in the managemet of of ichthyoses and related skin types," Dermatol Ther (2013) 26(1): doi: 10.1111 /j.1529-2019.2012.01527.x.

Dreyfus et al., "Burden of inherited ichthyosis: A french national survey," Acta Derm Venereol (2015) 95:326-328.

(56) References Cited

OTHER PUBLICATIONS

Dreyfus et al., "Prevalence of inherited ichthyosis in France: a study using capture-recapture method," Orphanet Journal of Rare diseases (2014) 9:1.

Eming SA, Krieg T, Davidson JM. Gene therapy and wound healing. Clin Dermatol. Jan.-Feb 2007;25(1):79-92.

European Medicines Agency, "Public summary of opinion on orphan designation," Published Jun. 18, 2013. 5 pages.

Farasat et al., "Novel transglutaminase-1 mutations and genotype-phenotype investigations of 104 patients with autosomal recessive congenital ichthyosis in the USA," J Med Genet (2009) 46(2):103-111.

Fernandes et al., "Increased Melanocytic Nevi in Patients with Inherited Ichthyoses: Report of a Previously Undescribed Association," Pediatric Dermatology (2010) 27(5):453-458.

Final Office Action received for U.S. Appl. No. 15/393,151, dated Aug. 31, 2017, 13 pages.

Fischer et al., "Cross-linking of SPINK6 by transglutaminases protects from epidermal proteases," Journal of Investigative Dermatology (2013) 133:1170-1177.

Fischer, "Autosomal recessive congenital ichthyosis," Journal of Investigative Dermatology (2009) 129:1319-1321.

Foundation for Ichthyosis & Related Skin Types, Inc, "Autosomal Recessive Congenital Ichthyosis—Lamellar Ichthyosis (ACRI—lamellar) type," Updated Sep. 12, 2016.

Franzke et al., "Epidermal ADAM17 maintains the skin barrier by regulating EGFR ligand-dependent terminal keratinocyte differentiation," J. Exp. Med (2012) 209(6):1105-1119.

Ganemo et al., "Quality of life in adults with congenital ichthyosis," Journal of Advanced nursing (2003) 44(4):412-419.

Georgiadis et al., "Lentiviral Engineered Fibroblasts Expressing Codon—Optimized COL7A1 Restore Anchoring Fibrils in RDEB", Journal of Investigative Dermatology, vol. 136, 2016, pp. 284-292.

Glorioso JC. Herpes simplex viral vectors: late bloomers with big potential. Hum Gene Ther. Feb. 2014;25(2):83-91.

Gorell et al., "Gene therapy for skin diseases," Cold Spring Harb Perspect Med (2014) 4:a015149.

Goto et al., "Fibroblasts Show More Potential as Target Cells than Keratinocytes in COL7A1 Gene Therapy of Dystrophic Epidermolysis Bullosa", Journal of Investigative Dermatology, vol. 126, 2006, pp. 766-772.

Grant, Kyle, "Production and Purification of Highly Replication Defective Hsv-1 Based Gene Therapy Vectors", Doctoral Dissertation, University of Pittsburgh, 2008, 137 pages.

Gurevich I, Agarwal P, Dolorita J, Prisco M, O'Malley M, et al. 759 Successful in vivo COL7A1 gene delivery and correction of recessive dystrophic epidermolysis bullosa (RDEB) skin using an off the shelf HSV-1 vector (KB103). J Invest Derm. vol. 138, Iss. 5 Supp. May 2018, p. S129. Available online Apr. 19, 2018.

Heikkinen et al., "Diremerization of human lysyl hydroxylase 3 (LH3) is mediated by the amino acids 541 547," Matrix Biology (2010) 30(1):27-33.

Hennig et al., HEK293-based production platform for y-retroviral (self-inactivating) vectors: application for safe and efficient transfer of COL7A1 cDNA. Hum Gene Ther Clin Dev. Dec. 2014;25(4):218-28.

Herman et al., "Transglutaminase-1 (TGM1) gene mutations in autosomal recessive congenital ichthyosis: Summary of mutations (including 23 novel) and modeling of TGase-1," Hum Mutat (2009) 30(4):537-547.

Hernandez-Martin et al., "A systematic review of clinical trials of treatments for the congenital ichthyoses, excluding ichthyosis vulgaris," J Am Avad Dermatol (2013) 69:544-549.

Hernandez-Martin et al., "Prevalence of autosomal recessive congenital ichthyosis: A population-based study using the capture-recapture method in Spain," J Am Acad Dermatol (2012) 67:240-244.

Hirsch et al., "Regeneration of the entire human epidermis using transgenic stem cells," Nature (2017) 551:327-332.

International Preliminary Report on Patentability received for PCT Patent Application No. PCT/US2016/068974, dated Oct. 18, 2018, 11 pages.

International Search Report and Written Opinion for PCT/US2019/027079, dated Jul. 26, 2019, 14 pages.

International Search Report and Written Opinion received for PCT Patent Application No. PCT/US2016/068974, dated May 18, 2017, 18 pages.

Invitation to Pay Additional Fee received for PCT Patent Application No. PCT/US2016/068974, mailed on Mar. 27, 2017, 8 pages.

Karanesh et al., "Herpes simplex virus infects most cell types in vitro: clues to its success," Virology Journal (2011) 8:481.

Kim et al., "Microneedles for Drug and Vaccine Delivery", Advanced Drug Delivery Reviews, vol. 64, 2012, pp. 1547-1568.

Kuramoto et al., "Development of ichthyosiform skin compensates for defective permeability barrier function in mice lacking transglutaminase 1," J Clin Invest (2002) 109:243-250.

Lachmann R. Herpes simplex virus-based vectors. Int J Exp Pathol. Oct. 2004;85(4): 177-90.

Laiho et al., "Transglutaminase 1 mutations in autosomla recessive congenital ichthyosis: private and recurrent mutations in an isolated population," Am J Hum Genet (1997) 61:529-538.

Lefevre et al., "Mutations in ichthyin a new gene on chromosome 5q33 in a new form of autosomal recessive congenital ichthyosis," Human Molecular Genetics (2004) 13(20):2473-2482.

Lewin AS, Glazer PM, Milstone LM. Gene therapy for autosomal dominant disorders of keratin. J Investig Dermatol Symp Proc. Oct. 2005;10(1):47-61.

Li et al., "The expression of epidermal lipoxygenases and transglutaminase-1 is perturbed by NIPAL4 mutations: indications of a common metabolic pathway essential for skin barrier homeostasis," Journal of Investigative Dermatology (2012) 132:2368-2375.

Lu, et al., "Topical Application of Viral Vectors for Epidermal Gene Transfer", The Journal of Investigative Dermatology, vol. 108, No. 5, May 1997, pp. 803-808.

Marconi P, Argnani R, Epstein AL, et al. HSV as a Vector in Vaccine Development and Gene Therapy. In: Madame Curie Bioscience Database [Internet], Austin (TX): Landes Bioscience; 2000-2013.

Marukian et al., "Establishing and validating an ichthyosis severity index," Journal of Investigative Dermatology (2017) 137:1834-1841.

Marukian et al., "Recent advances in understanding ichthyosis pathogenesis [version 1; references: 2 approved]," F1000 Research (2016) 5(F1000 Faculty Rev): 1497.

Mashima et al., "The role of lipoxygenases in pathophysiology; new insights and future perspectives," Redox Biology (2015) 6:297-310.

Mayr et al., "Gene Therapy for the COL7A1 Gene", Chapter 23, Intech, 2013, pp. 561-589.

Mazereeuw-Hautier et al., "Management of congenital ichthyoses: European guidelines of care, partone," Br J Dermatol (2019) 180(2):272-281.

Milstone et al., "Incidence of moderate to severe ichthyosis in the United States," Arch Dermatol (2012) 248(9):1080-1081.

Nafeey et al., "Branching of keratin intermediate filaments," Journal of Structural Biology (2016) 194:415-422.

National Organization for Rare Disorders (NORD), "Synonyms of Ichthyosis, Lamellar," (2005) 5 pages.

Natsuga et al., "Malignant skin tumours in patients with inherited ichthyosis," BJD (2011) 165:236-268.

Nemes et al., "A novel function for transglutaminase 1: Attachment of long-chain ω-hydroxyceramides to involucrin by ester bond formation," Proc Natl Acad Sci USA (1999) 96:8402-8407.

Nemes et al., "Involucrin cross-linking by transglutaminase 1," The Journal of Biological Chemistry (1999) 274(16):11013-11021.

Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.

Non-Final Office Action received for U.S. Appl. No. 15/393,151, dated Apr. 14, 2017, 13 pages.

Non-Final Office Action received for U.S. Appl. No. 15/851,488, dated May 14, 2018, 10 pages.

(56) References Cited

OTHER PUBLICATIONS

Non-Final Office Action received for U.S. Appl. No. 16/177,153, dated May 9, 2019, 13 pages.
Non-final Rejection for U.S. Appl. No. 16/381,557, dated Aug. 21, 2019, 9 pages.
Notice of Allowance for U.S. Appl. No. 16/381,557, dated Nov. 15, 2019, 8 pages.
Notice of Allowance received for U.S. Appl. No. 15/393,151, dated Dec. 6, 2017, 11 pages.
Notice of Allowance received for U.S. Appl. No. 15/851,488, dated Oct. 29, 2018, 11 pages.
Notice of Allowance received for U.S. Appl. No. 16/177,153, dated Aug. 30, 2019, 10 pages.
Ortega-Recalde et al., "A novel TGM1 mutation, leading to multiple splicing rearrangments, is associated with autosomal recessive congenital ichthyosis," Clinical and Experimental Dermatology (2015) 40:757-760.
Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.
O'shaughnessy et al., "Interleukin-1 aplpha blockade prevents hyperkeratosis in an in vitro model of lamellar ichthyosis," Human Molecular Genetics (2010) 19(13):2594-2605.
Osman-Ponchet et al., "Pretreatment of skin using an abrasive skin preparation pad, a microneedling device or iontophoresis improves absorption of methyl aminolevulinate in ex vivo human skin," Phtodiagnosis and Photodynamic Therapy (2017) 20:130-136.
Otsuka et al., "Possible new therpeutic strategy to regulate atopic dermatitis through upregulating filaggrin expression," J Allergy Clin Immunol (2014) 133:139-146.
Pavez Lorie et al., "Expression of teinoid-regulated genees in lamellar ichthyosis vs. healthy control epidermis: Changes after oral treatments with liarozole*," Acta Derm Venereol (2009) 89:12-20.
Pearce et al., "Low-dose acitretin is associated with fewer adverse events than high-dose acitretin in the treatment of psoriasis," Arch Dermatol (2006) 142:1000-1004.
Pigg et al., "Spectrum of autosomal recessive congenital ichthyosis in Scandinavia: Clinical characteristics and novel and recurrent mutations in 132 patients*" Acta Derm Venereol (2016) 96:932-937.
Pigg et al., "Strong founder effect for a transglutaminase 1 gene mutation in lamellar ichthyosis and congenital ichthyosiform erythroderma from Norway," European Journal of Human Genetics (1998) 6:589-596.
Raghunath et al., "A novel in situ method for detection of deficient transglutaminase activity in the skin," Arch Dermatol Res (1998) 290:621-627.
Richard, "Autosomal recessive congenital ichthyosis," NCBI Bookshelf. Updated May 18, 2017.
Rodriguez-Pazos et al., "Autosomal recessive congenital ichthyosis," Aetas Dermosifiliogr (2013) 104(4):270-284.
Salmon-Ehr et al., "Implication of Interleukin-4 in Wound Healing", Laboratory Investigation, vol. 80, No. 8, Aug. 2000, pp. 1337-1343.
Samaniego et al., "Persistence and Expression of the Herpes Simplex Virus Genome in the Absence of Immediate-Early Proteins", Journal of Virology, vol. 72, No. 4, Apr. 1998, pp. 3307-3320.
Sandberg, "Lamellar Ichthyosis," Pediatrics in Review (1981) 2(7):213.
Sankar et al., "A novel role for keratin 17 in coordinating oncogenic transformation and cellular adhersion in eqing sarcoma," Molecular and Cellular Biology (2013) 33(22):4448-4460.
Sharma et al., "Collodion Baby with TGMI gene mutation," International Medical Case Reports Journal (2015) 8:205-208.
Silva et al., "Herpes Virus Amplicon Vectors", Viruses, vol. 1, 2009, pp. 594-629.
Siprashvili et al., "Long-term type VII collagen restoration to human epidermolysis bullosa skin tissue," Hum Gene Ther. Oct. 2010;21 (10):1299-310.
Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.
Styperek et al., "Annual direct and indirect health costs of the congenital ichthyoses," Pediatric Dermatology (2010) 27(4):325-336.
Sugimura et al., "Identification of preferred substrate sequences for transglutaminase 1—development of a novel peptide that can efficiently detect cross-linking enzyme activity in the skin," FEBS Journal (2008) 275:5667-5677.
Traupe et al., "Nonsyndromic types of ichthyoses—an update," Jorunal of the Germain Society of Dermotology (2013) 109-121.
U.S. Unpublished U.S. Appl. No. 16/581,150, filed Sep. 24, 2019, titled "Compositions and Methods for the Treatment of Netherton Syndrome" (Copy not submitted herewith pursuant to the waiver of 37 C.F.R. § 1.98(a)(2)(iii)).
U.S. Unpublished U.S. Appl. No. 16/598,982, filed Oct. 10, 2019, titled "Compositions and Methods for the Treatment of Wounds, Disorders, and Diseases of the Skin" (Copy not submitted herewith pursuant to the waiver of 37 C.F.R. § 1.98(a)(2)(iii)).
Uitto et al., "Progress toward Treatment and Cure of Epidermolysis Bullosa: Summary of the Debra International Research Symposium EB2015", Journal of Investigative Dermatology, vol. 136, 2016, pp. 352-358.
Ullah et al., "Novel mutations in the genes TGM1 and ALOXE3 underlying autosomal recessive congenital ichthyosis," Int J Dermatol (2016) 55(5):524.
Vahlquist et al., "Congenital ichthyosis: an overview of crrent and emerging therpies," Acta Derm Venereol (2008) 88:4-14.
Vahlquist et al., "Genotypic and clinical spectrum of self-improving collodio ichthyosis: ALOX12B, ALOXE3, and TGM1 mutations in Scandinavian patients," Journal of Investigative Dermatology (2010) 130:438-443.
Vahlquist et al., "Oral liarozole in the treatment of patients with moderate/severe lamellar ichthyosis: results of a randomized, double-blind, multinational, placebo-controlled phase II/III trial," British Journal of Dermatology (2014) 170:173-181.
Vaigundan et al., "A novel mutation in the transglutaminase-1 gene in an autosomal Yecessive congenital ichthyosis patient," BioMed Research International (2014) Article ID 706827.
Wajid et al., "NIPAL4/Ichthyin is expressed in the granular layer of human epidermis and mutated in two pakistani families with autosomal recessive ichthyosis," Dermatology K2010) 220:8-14.
Wang et al., "Comparative Effectiveness of Antinociceptive Gene Therapies in Animal Models of Diabetic Neuropathic Pain", Gene Therapy, vol. 20, 2013, pp. 742-750.
Watanabe et al., "Properties of a Herpes Simplex Virus Multiple Immediate-early Gene-Deleted Recombinant as a Vaccine Vector", Virology, vol. 357, 2007, pp. 186-198.
Watt et al., "Lysyl Hydroxylase 3 Localizes to Epidermal Basement Membrane and Is Reduced in Patients with Recessive Dystrophic Epidermolysis Bullosa", Plos One, 10(9):e0137639, Year: 2015.
Weiss et al., "The Role of Interleukin 10 in the Pathogenesis and Potential Treatment of Skin Diseases", Journal of the American Academy of Dermatology, vol. 50, No. 5, May 2004, pp. 657-675.
White E, Bienemann A, Megraw L, Bunnun C, Gill S. Evaluation and optimization of the administration of a selectively replicating herpes simplex viral vector to the brain by convection-enhanced delivery. Cancer Gene Ther. May 2011;18(5):358-69. doi: 10.1038/cgt.2011.2. Epub Mar. 4, 2011.
Wolf et al., "ADAM17/EGFR axis promotes transglutaminase-dependent skin barrier formation through phosholipase C γ1 and protein kinase C pathways," Scientific Reports (2016) 6: Article ID: 39780.
Wolfe et al., "Engineering Herpes Simplex Viral Vectors for Therapeutic Gene Transfer", Chapter 6, Gene and Cell Therapy, 2004, pp. 103-129.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.

(56) References Cited

OTHER PUBLICATIONS

Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.

Yamane et al., "Analysis on transglutaminase 1 and its subtrates using specific substrate peptide in cultured kertinocytes," Biochemical and Biophysical Research Communications (2016) 478:343-348.

Yang et al., "Novel mutations of the transglutaminase 1 gene in lamellar ichthyosis," J Invest Dermatol (2001) 117:214-218.

Yu et al., "The lipoxygenase gene ALOXE3 implicated in skin differentiation encodes a hydroperoxide isomerase," PNAS (2003) 100(16):9162-9167.

Zhang et al., "Identification and functional characterization of a novel transflutaminase 1 gene mutation associated with autosomal recessive congenital ichthyosis," International Journal of Dermatology (2016) 55:201-207.

"U.S. Unpublished U.S. Appl. No. 17/639,878, filed Mar. 2, 2022, by Suma et al. titled ""Compositions and Methods for the Treatment of Congenital Ichthyoses (Copy not submitted herewith pursuant to the waiver of 37 C.F. R. § 1 98(a)(2)(iii) issued by the Office on Sep. 21, 2004)."

Boursnell et al., "Disabled infectious single cycle (DISC) herpes simplex virus as a vector for immunotherapy of cancer," Gene Therapy of Cancer (1998) 379-384.

Di et al., "Phase I study protocol for ex vivo lentiviral gene therapy for the inherited skin disease, Netherton syndrome," Hum Gene Ther Clin Dev. (2013) 24(4):182-190.

Goins et al. "Generation of replication-competent and -defective HSV vectors," Cold Spring Harb Protoc. May 1, 2011;2011 (5):pdb.protS6IS.

Krystal Biotech, Inc. "Krystal Biotech Announces Settlement with PeriphaGen, Inc." Mar. 15, 2022, https://ir.krystalbio.com/node/8481/pdf. (Year: 2022).

Mcgowan et al., ""Keratin 17 null mice exhibit age- and strain-dependent alopecia,"" Genes & Dev (2002) 16:1412-1422.

\* cited by examiner

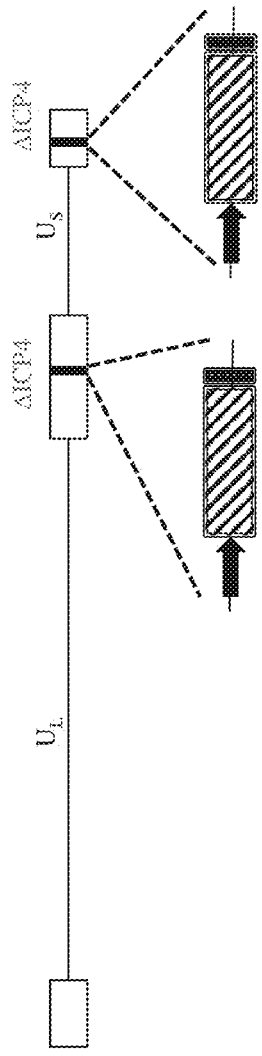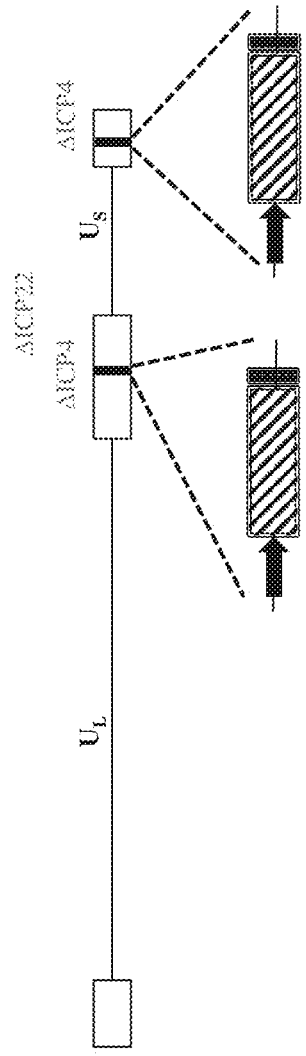

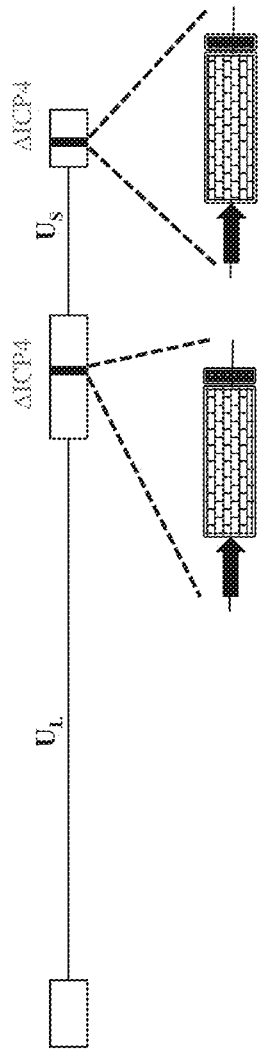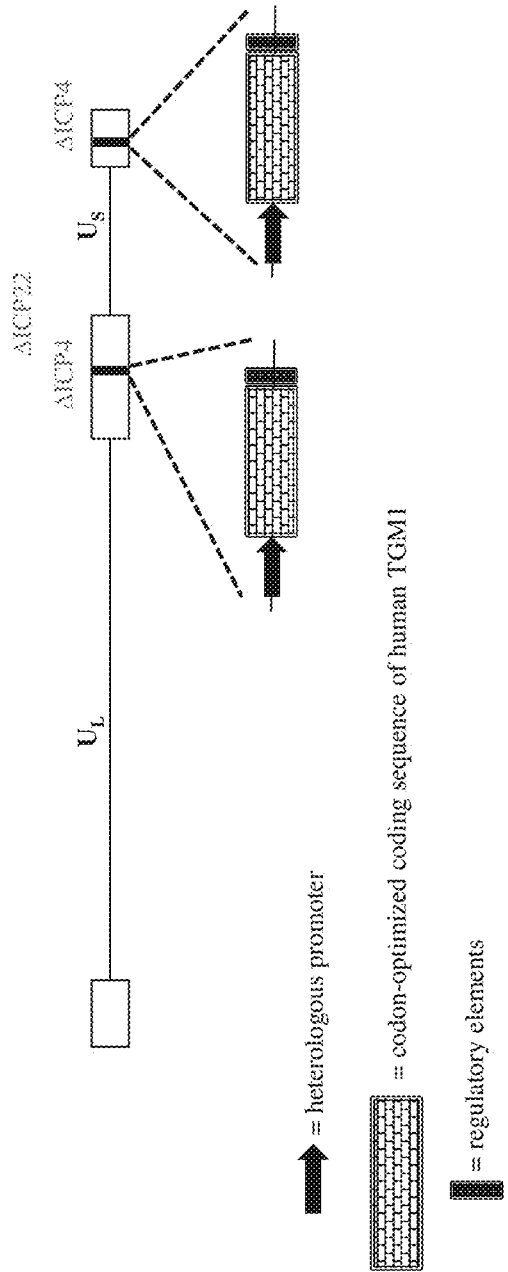

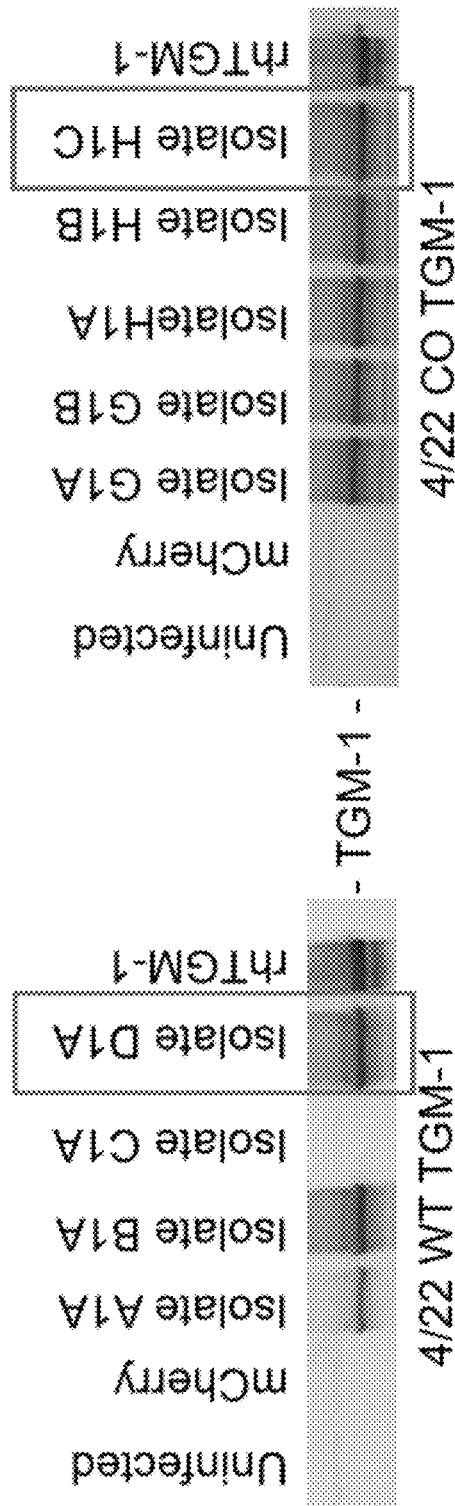
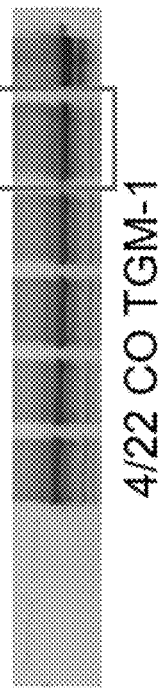
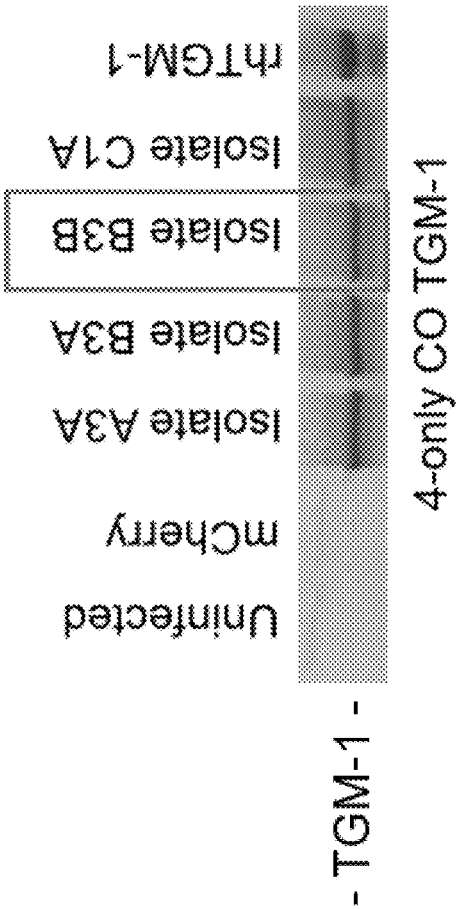
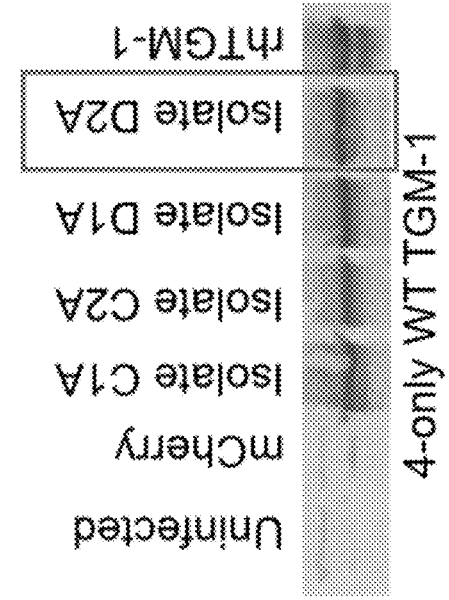
FIG. 2A
FIG. 2B
FIG. 2C
FIG. 2D

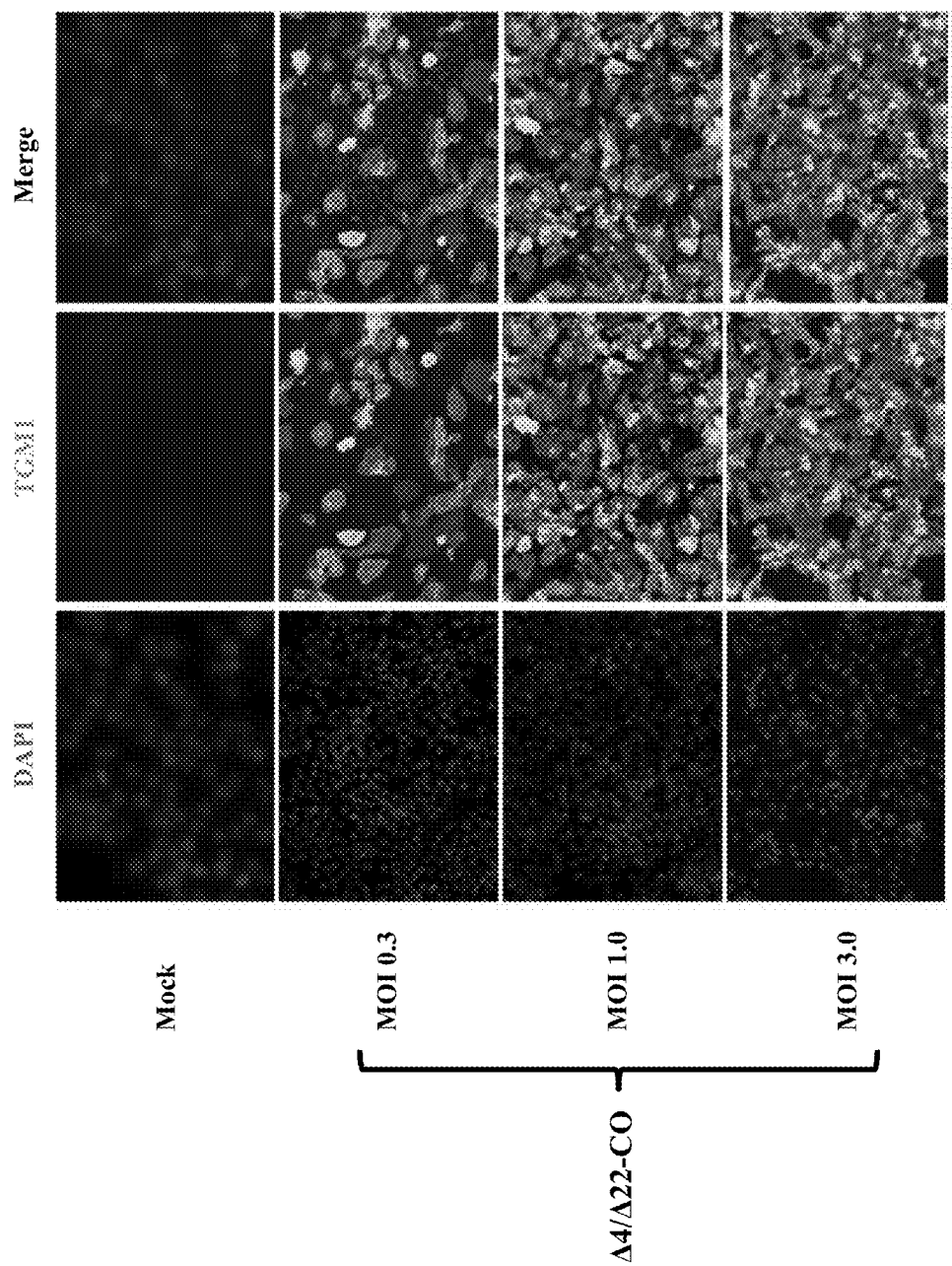

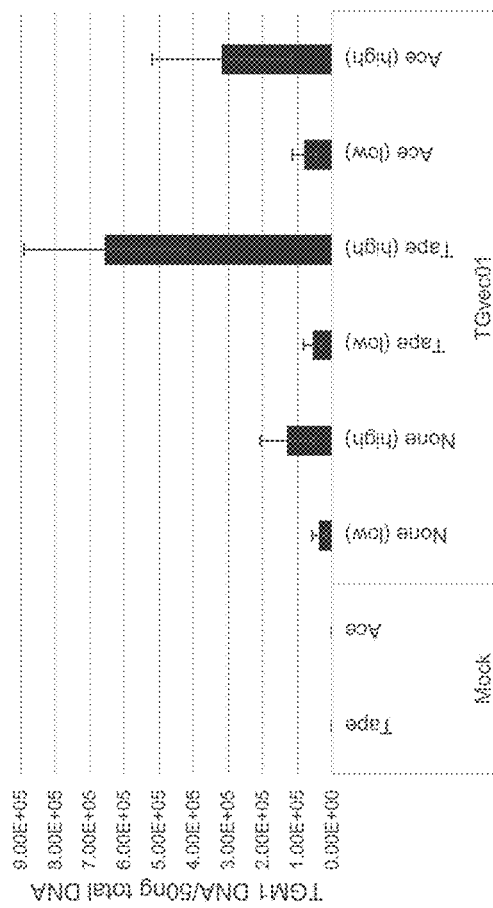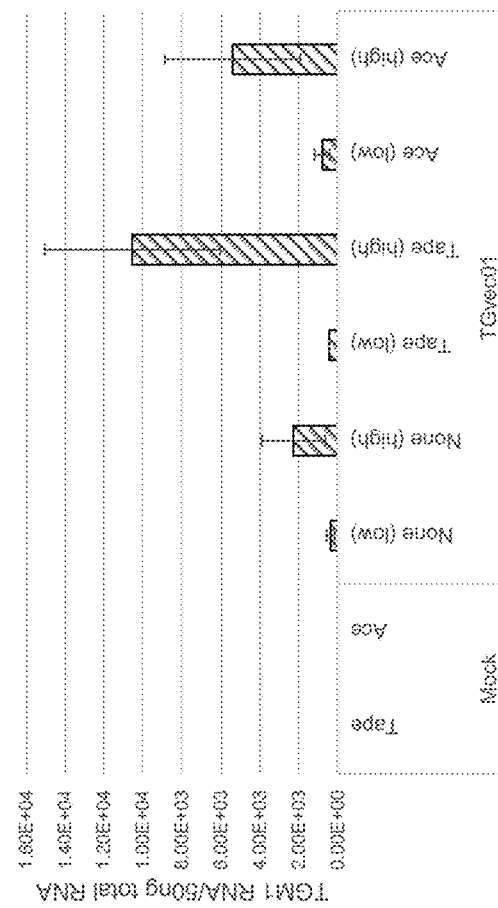

COMPOSITIONS AND METHODS FOR THE TREATMENT OF AUTOSOMAL RECESSIVE CONGENITAL ICHTHYOSIS

CROSS REFERENCE TO RELATED APPLICATIONS

This application is a continuation of U.S. patent application Ser. No. 16/381,557, filed Apr. 11, 2019, now U.S. Pat. No. 10,525,090, which claims the priority benefit of U.S. Provisional Application Ser. No. 62/656,768, filed Apr. 12, 2018, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761342000501SeqList.txt, date recorded: Nov. 11, 2019, size: 50 KB).

FIELD OF THE INVENTION

The present disclosure relates, in part, to recombinant nucleic acids, viruses, pharmaceutical compositions, and methods of their use for treating transglutaminase deficiencies (e.g., Transglutaminase-1 (TGM1) deficiencies) and/or for providing prophylactic, palliative, or therapeutic relief of a wound, disorder, or disease of the skin in a subject having, or at risk of developing, one or more signs or symptoms of autosomal recessive congenital ichthyosis (ARCI), e.g., lamellar ichthyosis (LI) and/or non-bullous congenital ichthyosiform erythroderma (NCIE).

BACKGROUND

Autosomal recessive congenital ichthyosis (ARCI) is a genetically and phenotypically heterogenous group of disorders that includes lamellar ichthyosis (LI) and non-bullous congenital ichthyosiform erythroderma (NCIE). The incidence of ARCI cases has been estimated at approximately 1 in 200,000 births. Infants affected by LI and NCIE are generally born with a shiny, waxy layer of skin (called a collodion membrane) that is typically shed within the first few weeks of life. For LI patients, the skin beneath the collodion membrane is red and scaly, and typically develops into the large, dark, plate-like scales covering the skin which are characteristic of the disease. For NCIE patients, the skin beneath the collodion membrane is red and covered with fine, white scales, and skin abnormalities (such as thickening of the skin on the palms and the soles of the feet) may persist into adulthood.

The management of ARCI is a life-long endeavor, which remains largely symptomatic. At present, disease treatment or management is generally supportive, and commonly focuses on reducing scaling and/or skin lubrication. A first-line therapy typically includes hydration and lubrication of the skin accomplished by creams and ointments containing low concentrations of salt, urea, or glycerol, which may increase water binding capacity of the stratum corneum. Topical or oral retinoid therapy may be recommended for those with severe skin involvement; however, these medications can be associated with undesired long-term adverse effects (including mucocutaneous disorders, musculoskeletal disorders, abnormal lipid profile and transaminase elevation, and teratogenicity), and are therefore generally prescribed with caution. Thus, there exists a clear need for novel treatment options for ARCI. The present disclosure addresses this and other needs.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

BRIEF SUMMARY

LI and NCIE represent a spectrum of disorders caused by mutations in one of at least nine genes; however, mutations in Transglutaminase-1 (TGM1) are most commonly observed in LI patients, and, to a lesser extent, in NCIE patients. The TGM1 gene is located on human chromosome 14q11.2 and has 15 exons. It encodes the polypeptide Transglutaminase-1 (TGM1), also known as ARCI1, ICR2, KTG, LI, LI1, TGK, or the TGase 1 enzyme, which is one of three TGase enzymes found in the epidermis. TGM1 participates in the formation of the cornified envelope, an essential scaffold upon which normal intercellular lipid layer formation occurs in the stratum corneum, by catalyzing calcium-dependent cross-linking of secreted proteins (such as involucrin, loricrin, and proline-rich proteins). TGM1 also catalyzes binding of ω-hydroxyceramides in the outer layer of the cornified envelope with proteins in the inner layer. At least 14 mutations have been identified in TGM1. In patients harboring TGM1 mutations, the cornified cell envelope is missing, and TGM1 activity is reduced or non-existent. Disruption to the cornified cell envelope and/or the intercellular lipid layer in the stratum corneum can lead to defects in barrier function, which in turn may lead to transepithelial water loss and compensatory hyperproliferation, resulting in the clinical manifestation of localized and/or generalized scaling, susceptibility to recurrent infections, and myriad other issues observed in TGM1-deficient patients.

Unfortunately, there are no presently available therapies targeting the molecular causes of ARCI. In some embodiments, the present disclosure addresses the deficiencies in TGM1 observed in this sensitive patient population while avoiding the long-term adverse effects observed using other therapies, e.g., retinoid therapy.

In some embodiments, provided herein are recombinant nucleic acids (e.g., recombinant herpes viral genomes) encoding transglutaminase polypeptides (e.g., TGM1 polypeptides) for use in viruses (e.g., herpes viruses), composition, pharmaceutical formulations, medicaments, and/or methods useful for supplementing or treating transglutaminase deficiencies in a subject in need thereof and/or for providing prophylactic, palliative, or therapeutic relief of a wound, disorder, or disease of the skin in a subject having, or at risk of developing, one or more signs or symptoms of ARCI (e.g., lamellar ichthyosis). The present inventors have shown that healthy keratinocytes, as well as keratinocytes derived from a patient suffering from Lamellar Ichthyosis, were capable of expressing human TGM1 when infected with recombinant virus (see e.g., Examples 2 and 4). Moreover, the present inventors have shown that an engineered HSV encoding human TGM1 was capable of expressing functional TGM1 in otherwise TGM1-deficient LI patient-derived keratinocytes grown in a 3D organotypic system (see e.g., Example 5). Finally, the present inventors have shown that TGM1 was successfully expressed in vivo in the skin of animals infected with an engineered virus disclosed herein after topical or intradermal administration of the virus (see e.g., Examples 3 and 6). Without wishing to be bound by theory, the data described herein provides strong evidence that the recombinant viruses of the present disclosure constitute a novel means for treating ARCI (such as LI).

Certain aspects of the present disclosure relate to a recombinant herpes virus genome comprising one or more polynucleotides encoding a transglutaminase (TGM) polypeptide. In some embodiments, the recombinant herpes virus genome comprises the one or more polynucleotides encoding the TGM polypeptide within one or more viral gene loci. In some embodiments, the recombinant herpes virus genome is replication competent. In some embodiments, the recombinant herpes virus genome is replication defective. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof. In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof.

In some embodiments, the recombinant herpes simplex virus genome is a recombinant type 1 herpes simplex virus (HSV-1) genome. In some embodiments that may be combined with any of the preceding embodiments, the recombinant herpes simplex virus genome comprises an inactivating mutation. In some embodiments that may be combined with any of the preceding embodiments, the inactivating mutation is in a herpes simplex virus gene. In some embodiments, the inactivating mutation is a deletion of the coding sequence of the herpes simplex virus gene. In some embodiments, the herpes simplex virus gene is selected from the group consisting of Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome comprises an inactivating mutation in the Joint region. In some embodiments, the recombinant herpes simplex virus genome comprises a deletion of the Joint region. In some embodiments that may be combined with any of the preceding embodiments, the recombinant herpes simplex virus genome comprises the one or more polynucleotides encoding the TGM polypeptide within one or both of the ICP4 viral gene loci. In some embodiments that may be combined with any of the preceding embodiments, the recombinant herpes simplex virus genome comprises the one or more polynucleotides encoding the TGM polypeptide within the ICP22 viral gene locus. In some embodiments that may be combined with any of the preceding embodiments, the recombinant herpes simplex virus genome comprises the one or more polynucleotides encoding the TGM polypeptide within the UL41 viral gene locus.

In some embodiments that may be combined with any of the preceding embodiments, the TGM polypeptide is selected from the group consisting of a TGM1 polypeptide, a TGM2 polypeptide, a TGM3 polypeptide, a TGM4 polypeptide, a TGM5 polypeptide, a TGM6 polypeptide, and a TGM7 polypeptide. In some embodiments that may be combined with any of the preceding embodiments, the TGM polypeptide is a human TGM polypeptide. In some embodiments that may be combined with any of the preceding embodiments, the TGM polypeptide is a human TGM1 polypeptide. In some embodiments that may be combined with any of the preceding embodiments, the TGM polypeptide has at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5. In some embodiments, the TGM polypeptide comprises the sequence of SEQ ID NO: 5.

In some embodiments that may be combined with any of the preceding embodiments, the recombinant herpes virus genome has reduced cytotoxicity when introduced into a target cell as compared to a corresponding wild-type herpes virus genome. In some embodiments, the target cell is a cell of the epidermis and/or dermis. In some embodiments, the target cell is a human cell.

Other aspects of the present disclosure relate to a herpes virus comprising any of the recombinant herpes virus genomes described herein. In some embodiments, the herpes virus is replication competent. In some embodiments, the herpes virus is replication defective. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, and a Kaposi's sarcoma-associated herpesvirus. In some embodiments that may be combined with any of the preceding embodiments, the herpes virus is a herpes simplex virus. In some embodiments that may be combined with any of the preceding embodiments, the herpes simplex virus is a type 1 herpes simplex virus (HSV-1), a type 2 herpes simplex virus (HSV-2), or any derivatives thereof.

Other aspects of the present disclosure relate to a pharmaceutical composition comprising (a) any of the recombinant herpes virus genomes and/or any of the herpes viruses described herein, and (b) a pharmaceutically acceptable excipient. In some embodiments, the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration. In some embodiments, the pharmaceutical composition is suitable for topical, transdermal, subcutaneous, intradermal, or transmucosal administration. In some embodiments, the pharmaceutical composition is suitable for topical administration.

Other aspects of the present disclosure relate to any of the recombinant herpes virus genomes, herpes viruses, and/or pharmaceutical compositions described herein for use as a medicament.

Other aspects of the present disclosure relate to any of the recombinant herpes virus genomes, herpes viruses, and/or pharmaceutical compositions described herein for use in a therapy.

Other aspects of the present disclosure relate to the use of any of the recombinant herpes virus genomes, herpes viruses, and/or pharmaceutical compositions described herein in the manufacture of a medicament for treating autosomal recessive congenital ichthyosis (ARCI).

Other aspects of the present disclosure relate to a method of enhancing, increasing, augmenting, and/or supplementing the levels of a TGM polypeptide in one or more cells of a subject comprising administering to the subject an effective amount of any of the recombinant herpes virus genomes, herpes viruses, and/or pharmaceutical compositions described herein.

Other aspects of the present disclosure relate to a method of enhancing production of cornified cell envelopes and/or stabilizing the stratum corneum layer of the skin of a subject comprising administering to the subject an effective amount of any of the recombinant herpes virus genomes, herpes viruses, and/or pharmaceutical compositions described herein.

Other aspects of the present disclosure relate to a method of treating a barrier function defect in a subject in need thereof comprising administering to the subject an effective amount of any of the recombinant herpes virus genomes, herpes viruses, and/or pharmaceutical compositions described herein.

Other aspects of the present disclosure relate to a method of providing prophylactic, palliative, or therapeutic relief to one or more signs or symptoms of autosomal recessive congenital ichthyosis (ARCI) in a subject in need thereof comprising administering to the subject an effective amount of any of the recombinant herpes virus genomes, herpes viruses, and/or pharmaceutical compositions described herein. In some embodiments, the one or more signs or symptoms of ARCI are selected from an abnormal stratum corneum, incomplete thickening of the cornified cell envelope, defects in the intercellular lipid layers in the stratum corneum, generalized scaling with variable redness of the skin, formation of large plate-like scales, accelerated epidermal turnover, palmoplantar hyperkeratosis, defective barrier function, recurrent skin infections, exposure keratitis, hypohidrosis, heat intolerance, corneal perforation, rickets, nail abnormalities, dehydration, respiratory problems, ectropion, eclabium, hypoplasia of joint and nasal cartilage, hypotrichosis, scarring alopecia, renal insufficiency, and sepsis.

In some embodiments that may be combined with any of the preceding embodiments, the subject is a human. In some embodiments that may be combined with any of the preceding embodiments, the subject suffers from lamellar ichthyosis (LI) and/or non-bullous congenital ichthyosiform erythroderma (NCIE). In some embodiments that may be combined with any of the preceding embodiments, the subject suffers from lamellar ichthyosis. In some embodiments that may be combined with any of the preceding embodiments, the subject's genome comprises a loss-of-function mutation in a TGM gene. In some embodiments, the subject's genome comprises a loss-of-function mutation in a TGM1 gene.

In some embodiments that may be combined with any of the preceding embodiments, the recombinant herpes virus genome, the herpes virus, and/or the pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, locally, or via inhalation to the subject. In some embodiments that may be combined with any of the preceding embodiments, the recombinant herpes virus genome, the herpes virus, and/or the pharmaceutical composition is administered topically, transdermally, subcutaneously, or intradermally to the subject. In some embodiments that may be combined with any of the preceding embodiments, the recombinant herpes virus genome, the herpes virus, and/or the pharmaceutical composition is administered topically to the subject. In some embodiments that may be combined with any of the preceding embodiments, the skin of the subject is abraded prior to administration of the recombinant herpes virus genome, the herpes virus, and/or the pharmaceutical composition.

Other aspects of the present disclosure relate to a pharmaceutical composition comprising: a) a herpes simplex virus (HSV) comprising a recombinant nucleic acid, wherein the recombinant nucleic acid comprises one or more polynucleotides encoding a Transglutaminase 1 (TGM1) polypeptide; and b) a pharmaceutically acceptable carrier. In some embodiments, the recombinant nucleic acid comprises two or more polynucleotides encoding a TGM1 polypeptide. In some embodiments, the HSV is replication-defective. In some embodiments, the HSV is replication-competent. In some embodiments that may be combined with any of the preceding embodiments, the HSV is a herpes simplex type 1 virus, a herpes simplex type 2 virus, or any derivatives thereof.

In some embodiments that may be combined with any of the preceding embodiments, the recombinant nucleic acid is a herpes simplex virus amplicon. In some embodiments, the herpes simplex virus amplicon is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

In some embodiments that may be combined with any of the preceding embodiments, the recombinant nucleic acid is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in a herpes simplex virus gene. In some embodiments, the herpes simplex virus gene is selected from the group consisting of Infected Cell Protein (ICP) 0, ICP4, ICP22, ICP27, ICP47, thymidine kinase (tk), Long Unique Region (UL) 41, and UL55. In some embodiments, the recombinant herpes simplex virus genome comprises an inactivation mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the inactivating mutation is a deletion of the coding sequence of the gene(s).

In some embodiments that may be combined with any of the preceding embodiments, the recombinant herpes simplex virus genome comprises the one or more polynucleotides within one or more viral gene loci. In some embodiments that may be combined with any of the preceding embodiments, the recombinant herpes simplex virus genome comprises the one or more polynucleotides within one or both of the ICP4 viral gene loci. In some embodiments that may be combined with any of the preceding embodiments, the recombinant herpes simplex virus genome comprises the one or more polynucleotides within the ICP22 viral gene locus. In some embodiments that may be combined with any of the preceding embodiments, the recombinant herpes simplex virus genome comprises the one or more polynucleotides within the UL41 viral gene locus. In some embodiments that may be combined with any of the preceding embodiments, the HSV has reduced cytotoxicity as compared to a wild-type herpes simplex virus.

In some embodiments that may be combined with any of the preceding embodiments, the TGM1 polypeptide is a human TGM1 polypeptide. In some embodiments that may be combined with any of the preceding embodiments, the one or more polynucleotides encoding the TGM1 polypeptide have at least 80%, at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 1 or SEQ ID NO: 2. In some embodiments that may be combined with any of the preceding embodiments, the TGM1 polypeptide has at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5.

In some embodiments that may be combined with any of the preceding embodiments, the pharmaceutically acceptable carrier is adapted for cutaneous (systemic or topical), transdermal, subcutaneous, and/or intradermal administration. In some embodiments that may be combined with any of the preceding embodiments, the pharmaceutically acceptable carrier is adapted for topical administration. In some embodiments that may be combined with any of the preceding embodiments, the pharmaceutically acceptable carrier comprises a hydroxypropyl methylcellulose gel. In some embodiments that may be combined with any of the preceding embodiments, the pharmaceutically acceptable carrier comprises a phosphate buffer. In some embodiments that may be combined with any of the preceding embodiments, the pharmaceutically acceptable carrier comprises glycerol.

Other aspects of the present disclosure relate to a kit comprising any of the pharmaceutical composition described herein and instructions for administering the pharmaceutical composition.

Other aspects of the present disclosure relate to a method of enhancing, increasing, augmenting, and/or supplementing the levels of a TGM1 polypeptide in one or more cells of a subject, comprising administering to the subject an effective amount of any of the pharmaceutical compositions described herein. In some embodiments, the subject is a human. In some embodiments, the subject suffers from lamellar ichthyosis (LI) and/or non-bullous congenital ichthyosiform erythroderma (NCIE). In some embodiments, the subject suffers from lamellar ichthyosis (LI). In some embodiments that may be combined with any of the preceding embodiments, the pharmaceutical composition is administered cutaneously (systemically or topically), transdermally, subcutaneously, or intradermally to the subject. In some embodiments that may be combined with any of the preceding embodiments, the pharmaceutical composition is administered topically to the subject. In some embodiments that may be combined with any of the preceding embodiments, the pharmaceutical composition is administered one, two, three, four, five or more times per day. In some embodiments that may be combined with any of the preceding embodiments, the pharmaceutical composition is administered to one or more affected and/or unaffected areas of the subject. In some embodiments that may be combined with any of the preceding embodiments, the skin of the subject is abraded prior to administration of the pharmaceutical composition.

Other aspects of the present disclosure relate to a method of enhancing production of cornified cell envelopes and/or stabilizing the stratum corneum layer of the skin of a subject, comprising administering to the subject an effective amount of any of the pharmaceutical compositions described herein. In some embodiments, the subject is a human. In some embodiments, the subject suffers from lamellar ichthyosis (LI) and/or non-bullous congenital ichthyosiform erythroderma (NCIE). In some embodiments, the subject suffers from lamellar ichthyosis (LI). In some embodiments that may be combined with any of the preceding embodiments, the pharmaceutical composition is administered cutaneously (systemically or topically), transdermally, subcutaneously, or intradermally to the subject. In some embodiments that may be combined with any of the preceding embodiments, the pharmaceutical composition is administered topically to the subject. In some embodiments that may be combined with any of the preceding embodiments, the pharmaceutical composition is administered one, two, three, four, five or more times per day. In some embodiments that may be combined with any of the preceding embodiments, the pharmaceutical composition is administered to one or more affected and/or unaffected areas of the subject. In some embodiments that may be combined with any of the preceding embodiments, the skin of the subject is abraded prior to administration of the pharmaceutical composition.

Other aspects of the present disclosure relate to a method of treating a barrier function defect in a subject in need thereof, comprising administering to the subject an effective amount of any of the pharmaceutical compositions described herein. In some embodiments, the subject is a human. In some embodiments, the subject suffers from lamellar ichthyosis (LI) and/or non-bullous congenital ichthyosiform erythroderma (NCIE). In some embodiments, the subject suffers from lamellar ichthyosis (LI). In some embodiments that may be combined with any of the preceding embodiments, the pharmaceutical composition is administered cutaneously (systemically or topically), transdermally, subcutaneously, or intradermally to the subject. In some embodiments that may be combined with any of the preceding embodiments, the pharmaceutical composition is administered topically to the subject. In some embodiments that may be combined with any of the preceding embodiments, the pharmaceutical composition is administered one, two, three, four, five or more times per day. In some embodiments that may be combined with any of the preceding embodiments, the pharmaceutical composition is administered to one or more affected and/or unaffected areas of the subject. In some embodiments that may be combined with any of the preceding embodiments, the skin of the subject is abraded prior to administration of the pharmaceutical composition.

Other aspects of the present disclosure relate to a method of providing prophylactic, palliative, or therapeutic relief to one or more signs or symptoms of autosomal recessive congenital ichthyosis (ARCI) in a subject in need thereof, comprising administering to the subject an effective amount of any of the pharmaceutical compositions described herein. In some embodiments, the subject is a human. In some embodiments, the subject suffers from lamellar ichthyosis (LI) and/or non-bullous congenital ichthyosiform erythroderma (NCIE). In some embodiments, the subject suffers from lamellar ichthyosis (LI). In some embodiments that may be combined with any of the preceding embodiments, the pharmaceutical composition is administered cutaneously (systemically or topically), transdermally, subcutaneously, or intradermally to the subject. In some embodiments that may be combined with any of the preceding embodiments, the pharmaceutical composition is administered topically to the subject. In some embodiments that may be combined with any of the preceding embodiments, the pharmaceutical composition is administered one, two, three, four, five or more times per day. In some embodiments that may be combined with any of the preceding embodiments, the pharmaceutical composition is administered to one or more affected and/or unaffected areas of the subject. In some embodiments that may be combined with any of the preceding embodiments, the skin of the subject is abraded prior to administration of the pharmaceutical composition. In some embodiments that may be combined with any of the preceding embodiments, the one or more signs or symptoms of ARCI are selected from an abnormal stratum corneum, incomplete thickening of the cornified cell envelope, defects in the intercellular lipid layers in the stratum corneum, generalized scaling with variable redness of the skin, formation of large plate-like scales, accelerated epidermal turnover, palmoplantar hyperkeratosis, defective barrier function, recurrent skin infections, exposure keratitis, hypohidrosis, heat intolerance, corneal perforation, rickets, nail abnormalities, dehydration, respiratory problems, ectropion, eclabium, hypoplasia of joint and nasal cartilage, hypotrichosis, scarring alopecia, renal insufficiency, and sepsis.

Other aspects of the present disclosure relate to a recombinant nucleic acid comprising one or more polynucleotides encoding a Transglutaminase 1 (TGM1) polypeptide, wherein the recombinant nucleic acid is a recombinant herpes simplex virus genome. In some embodiments, the recombinant herpes simplex virus genome comprises two or more polynucleotides encoding a TGM1 polypeptide. In some embodiments that may be combined with any of the preceding embodiments, the recombinant herpes simplex virus genome is a recombinant HSV-1 genome, a recombinant HSV-2 genome, or any derivatives thereof.

In some embodiments that may be combined with any of the preceding embodiments, the recombinant herpes simplex virus genome comprises an inactivating mutation in a herpes simplex virus gene. In some embodiments, the herpes simplex virus gene is selected from the group consisting of ICP0, ICP4, ICP22, ICP27, ICP47, tk, UL41, and UL55. In some embodiments, the recombinant herpes simplex virus genome comprises an inactivation mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the inactivating mutation is a deletion of the coding sequence of the gene(s).

In some embodiments that may be combined with any of the preceding embodiments, the recombinant herpes simplex virus genome comprises the one or more polynucleotides within one or more viral gene loci. In some embodiments that may be combined with any of the preceding embodiments, the recombinant herpes simplex virus genome comprises the one or more polynucleotides within one or both of the ICP4 viral gene loci. In some embodiments that may be combined with any of the preceding embodiments, the recombinant herpes simplex virus genome comprises the one or more polynucleotides within the ICP22 viral gene locus. In some embodiments that may be combined with any of the preceding embodiments, the recombinant herpes simplex virus genome comprises the one or more polynucleotides within the UL41 viral gene locus.

In some embodiments that may be combined with any of the preceding embodiments, the TGM1 polypeptide is a human TGM1 polypeptide. In some embodiments that may be combined with any of the preceding embodiments, the one or more polynucleotides encoding the TGM1 polypeptide have at least 80%, at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 1 or SEQ ID NO: 2. In some embodiments that may be combined with any of the preceding embodiments, the TGM1 polypeptide has at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5.

Other aspects of the present disclosure relate to a host cell comprising any of the recombinant nucleic acids described herein. In some embodiments, the host cell is a eukaryotic cell. In some embodiments, the host cell is a mammalian cell. In some embodiments, the host cell is a human cell or a non-human primate cell. In some embodiments, the host cell is a Vero cell. In some embodiments, the host cell is a complementing host cell.

Other aspects of the present disclosure relate to a method of collecting a herpes simplex virus comprising: a) contacting a complementing host cell with any of the recombinant nucleic acids described herein, and b) collecting the herpes simplex virus generated by the complementing host cell.

Other aspects of the present disclosure relate to a method of collecting a herpes simplex virus comprising: a) culturing any of the host cells described herein, and b) collecting the herpes simplex virus generated by the host cell.

BRIEF DESCRIPTION OF THE DRAWINGS

FIGS. 1A-E show schematics of wild-type and modified herpes simplex virus genomes. FIG. 1A shows a wild-type herpes simplex virus genome. FIG. 1B shows a modified herpes simplex virus genome comprising deletions of the coding sequence of ICP4 (both copies), with an expression cassette containing a wild-type coding sequence of the human Transglutaminase-1 (TGM1) protein integrated at each of the ICP4 loci. FIG. 1C shows a modified herpes simplex virus genome comprising deletions of the coding sequences of ICP4 (both copies) and ICP22, with an expression cassette containing a wild-type coding sequence of the human Transglutaminase-1 (TGM1) protein integrated at each of the ICP4 loci. FIG. 1D shows a modified herpes simplex virus genome comprising deletions of the coding sequence of ICP4 (both copies), with an expression cassette containing a codon-optimized coding sequence of the human Transglutaminase-1 (TGM1) protein integrated at each of the ICP4 loci. FIG. 1E shows a modified herpes simplex virus genome comprising deletions of the coding sequences of ICP4 (both copies) and ICP22, with an expression cassette containing a codon-optimized coding sequence of the human Transglutaminase-1 (TGM1) protein integrated at each of the ICP4 loci.

FIGS. 2A-D show western blot analyses of wild-type (WT) or codon-optimized (CO) human TGM-1 expression in ICP4-complementing Vero cells infected with various isolates of modified herpes simplex virus 1 (HSV-1). Uninfected cells and cells infected with a corresponding modified HSV-1 isolate encoding mCherry were used as negative controls; recombinant human (rh) TGM1 was used as a positive control. FIG. 2A shows human TGM1 protein levels in Vero cells 48-72 hours after infection with one of four independent isolates (A1A, B1A, C1A, and D1A) of attenuated ΔICP4 (both copies)/ΔICP22-modified HSV-1 (4/22) containing a wild-type (WT) human TGM1 cDNA expression cassette integrated at both ICP4 loci. FIG. 2B shows human TGM1 protein levels in Vero cells 48-72 hours after infection with one of five independent isolates (G1A, G1B, H1A, H1B, and H1C) of attenuated ΔICP4 (both copies)/ΔICP22-modified HSV-1 (4/22) containing a codon-optimized (CO) human TGM1 cDNA expression cassette integrated at both ICP4 loci. FIG. 2C shows human TGM1 protein levels in Vero cells 48-72 hours after infection with one of four independent isolates (C1A, C2A, D1A, and D2A) of attenuated AICP4 (both copies) modified HSV-1 (4-only) containing a wild-type (WT) human TGM1 cDNA expression cassette integrated at both ICP4 loci. FIG. 2D shows human TGM1 protein levels in Vero cells 48-72 hours after infection with one of four independent isolates (A3A, B3A, B3B, and C1A) of attenuated AICP4 (both copies)-modified HSV-1 (4-only) containing a wild-type (WT) human TGM1 cDNA expression cassette integrated at both ICP4 loci. The isolates indicated in the boxes were selected for further analysis.

FIGS. 5A-B show immunofluorescence images of human TGM1 expression in mock infected HaCaT cells, or HaCaT cells infected with the indicated recombinant viruses at an MOI of 0.3, 1.0, or 3.0. FIG. 5A shows immunofluorescent detection of human TGM1 expression in HaCaT cells after mock infection or infection at the indicated MOIs with attenuated ΔICP4/ΔICP22-modified HSV-1 containing codon-optimized human TGM1 cDNA (Δ4/Δ22-CO). FIG. 5B shows immunofluorescent detection of human TGM1 expression in HaCaT cells after mock infection or infection at the indicated MOIs with attenuated 4ICP4-modified HSV-1 containing codon-optimized human TGM1 cDNA (Δ4-CO).

FIG. 7A shows qRT-PCR analysis of human TGM1 transcripts expressed in skin biopsies taken from BALB/c mice 48 hours after intradermal injection of ΔICP4 or ΔICP4/ΔICP22-modified HSV-1 encoding wild-type (WT) human TGM1 (2 mice/strain). FIG. 7B shows qRT-PCR analysis of human TGM1 transcripts expressed in skin biopsies taken from BALB/c mice 48 hours after intradermal injection of ΔICP4 or ΔICP4/ΔICP22-modified HSV-1 encoding codon-optimized (CO) human TGM1 (2 mice/strain).

FIG. 8A shows immunofluorescent detection of human TGM1 expression in skin sections after mock infection, infection with attenuated ΔICP4/ΔICP22-modified HSV-1 encoding codon-optimized human TGM1 (coTGM1-4/22), or infection with attenuated ΔICP4-modified HSV-1 encoding wild-type human TGM1 (wtTGM1-4). DAPI staining was used to visualize nuclei. FIG. 8B shows H&E staining of mouse skin tissue sections after mock infection, infection with attenuated ΔICP4/ΔICP22-modified HSV-1 encoding codon-optimized human TGM1 cDNA (coTGM1-4/22), or infection with attenuated ΔICP4-modified HSV-1 encoding wild-type human TGM1 cDNA (wtTGM1-4).

FIG. 9A shows the levels of TGM1 DNA present in immortalized normal keratinocytes 48 hours after infection with TGvec01 at the indicated MOIs, as determined by qPCR analysis. FIG. 9B shows the levels of TGM1 transcripts present in immortalized normal keratinocytes 48 hours after infection with TGvec01 at the indicated MOIs, as determined by qRT-PCR analysis. FIG. 9C shows the levels of TGM1 DNA present in immortalized LI keratinocytes 48 hours after infection with TGvec01 at the indicated MOIs, as determined by qPCR analysis. FIG. 9D shows the levels TGM1 transcripts present in immortalized LI keratinocytes 48 hours after infection with TGvec01 at the indicated MOIs, as determined by qRT-PCR analysis. FIG. 9E shows western blot analysis of human TGM1 protein expression in immortalized normal keratinocytes 48 hours after infection with TGvec01 at the indicated MOIs. FIG. 9F shows western blot analysis of human TGM1 protein expression in immortalized LI keratinocytes 48 hours after infection with TGvec01 at the indicated MOIs. FIG. 9G shows representative immunofluorescence images of human TGM1 protein expression in immortalized normal keratinocytes 48 hours after infection with TGvec01 at the indicated MOIs. FIG. 9H shows representative immunofluorescence images of human TGM1 protein expression in immortalized LI keratinocytes 48 hours after infection with TGvec01 at the indicated MOIs. For these experiments, uninfected (mock) and HSV-mCherry-infected (mCherry) cells were used as negative controls. For each condition in the qPCR and qRT-PCR analysis, data is presented for two replicates ±SEM. For western blot analysis, recombinant human (rh) TGM1 was used as a positive control, while GAPDH was used as a loading control. For immunofluorescence analysis, DAPI staining was used to visualize nuclei.

FIG. 10A shows western blot analysis of human TGM1 protein expression in primary normal keratinocytes 48 hours after infection with TGvec01 at the indicated MOIs. FIG. 10B shows western blot analysis of human TGM1 protein expression in primary LI keratinocytes 48 hours after infection with TGvec01 at the indicated MOIs. FIG. 10C shows representative immunofluorescence images of human TGM1 protein expression in primary normal keratinocytes 48 hours after infection with TGvec01 at the indicated MOIs. FIG. 10D shows representative immunofluorescence images of human TGM1 protein expression in primary LI keratinocytes 48 hours after infection with TGvec01 at the indicated MOIs. For these experiments, uninfected (mock) and HSV-mCherry-infected (mCherry) cells were used as negative controls. For western blot analysis, recombinant human (rh) TGM1 was used as a positive control, while GAPDH was used as a loading control. For immunofluorescence analysis, DAPI staining was used to visualize nuclei.

FIG. 14A shows the levels of human TGM1 DNA present in representative skin biopsies taken from BALB/c mice topically treated with either TGvec01 or a negative control (mCherry) vector, as assessed by qPCR analysis. FIG. 14B shows the levels of human TGM1 transcripts present in the same representative skin biopsies taken from BALB/c mice topically treated with either TGvec01 or a negative control (mCherry) vector, as assessed by qRT-PCR analysis. For each condition in the qPCR and qRT-PCR analysis, data is presented for two replicates±SEM. FIG. 14C shows representative immunofluorescence images of human TGM1 and mouse loricrin protein expression in skin biopsies taken from BALB/c mice topically treated with either TGvec01 or a negative control (mCherry) vector. DAPI staining was used to visualize nuclei.

FIGS. 15A-B show nucleic acid analyses of skin biopsies taken from BALB/c mice 48 hours post-topical application of vehicle control or TGvec01. FIG. 15A shows the levels of human TGM1 DNA present in skin biopsies taken from BALB/c mice topically treated with vehicle alone (mock) or TGvec01 administered at one of two doses (low, $2\times10^7$ plaque forming units (PFU); high, $1\times10^8$ PFU) to unabraded (None), tape-stripped (Tape), or acetone-treated (Ace) skin, as assessed by qPCR analysis. FIG. 15B shows the levels of human TGM1 transcripts present in skin biopsies taken from BALB/c mice topically treated with vehicle alone (mock) or TGvec01 administered at one of two doses (low, $2\times10^7$ PFU; high, $1\times10^8$ PFU) to unabraded (None), tape-stripped (Tape), or acetone-treated (Ace) skin, as assessed by qRT-PCR analysis. For each condition in the qPCR and qRT-PCR analysis, data is presented as the average signal of two (mock) or four (TGvec01) treatment sites±SEM.

DETAILED DESCRIPTION

Figure 1A:
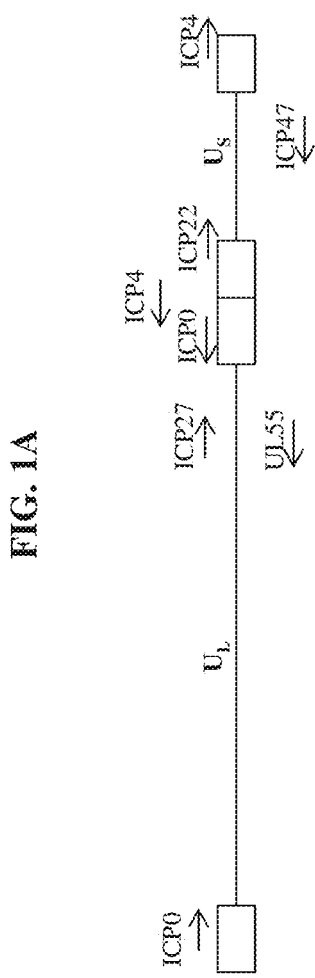

In some embodiments, the present disclosure relates to recombinant nucleic acids (e.g., recombinant herpes viral genomes) encoding TGM1 polypeptides, and/or use of these recombinant nucleic acids (e.g., in a herpes virus) in viruses, compositions, medicaments, and/or methods in order to supplement or treat TGM1 deficiencies. Without wishing to be bound by theory, it is believed that increasing, augmenting, and/or supplementing the levels of a TGM1 in one or more cells of a TGM1-deficient individual by administering one or more of the recombinant nucleic acids, viruses, and/or formulations described herein will allow for increased production of functional TGM1 in the individual. In addition, without wishing to be bound by theory, it is further believed that increasing, augmenting, and/or supplementing the levels of a TGM1 in one or more cells of an individual by administering one or more of the recombinant nucleic acids, viruses, and/or formulations described herein will lead to improved production of cornified cell envelopes and a stabilization of the stratum corneum layer of the subject, allowing for the improvement or treatment of barrier function defects, which are hallmarks of patients suffering from lamellar ichthyosis. Ultimately, without wishing to be bound by theory, it is believed that the recombinant nucleic acids, viruses, compositions, medicaments, and methods described herein will help to treat the existing skin abnormalities in individuals suffering from ARCI (such as individuals suffering from lamellar ichthyosis), as well as prevent or delay reformation of wounds or skin abnormalities in treated subjects.

The following description sets forth exemplary methods, parameters, and the like. It should be recognized, however, that such a description is not intended as a limitation on the scope of the present disclosure but is instead provided as a description of exemplary embodiments.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operatively linked" or "operably linked" means that the DNA or RNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some aspects, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject mammal to provide an effective dose of the active ingredient(s) employed.

As used herein, "cutaneous administration" or "cutaneously administering" refers to the delivery of a composition to a subject by contacting, directly or otherwise, a formulation comprising the composition to all ("systemic") or a portion ("topical") of the skin of a subject. The term encompasses several routes of administration including, but not limited to, topical and transdermal. Topical administration may be used as a means to deliver a composition to the epidermis or dermis of a subject, or to specific strata thereof.

As used herein, an "effective amount" is at least the minimum amount required to affect a measurable improvement or prevention of one or more symptoms of a particular disorder. An "effective amount" may vary according to factors such as the disease state, age, sex, and weight of the patient. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications used to treat symptoms of the disease (e.g., the use of retinoids), delaying the progression of the disease, and/or prolonging survival. An effective amount can be administered in one or more administrations. For purposes of the present disclosure, an effective amount of a recombinant nucleic acid, virus, and/or pharmaceutical composition is an amount sufficient to accomplish prophylactic or therapeutic treatment either directly or indirectly. As is understood in the clinical context, an effective amount of a recombinant nucleic acid, virus, and/or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with ARCI (e.g., lamellar ichthyosis) are mitigated or eliminated, including the reduction or elimination of plate-like scales at a localized site or over the whole body.

As used herein, the term "delaying progression of a disease refers to deferring, hindering, slowing, retarding, stabilizing, and/or postponing development of the disease (e.g., lamellar ichthyosis). This delay can be of varying lengths or time, depending on the history of the disease and/or the individual being treated. As is evident to one of ordinary skill in the art, a sufficient or significant delay can, in effect, encompass prevention, in that the individual does not develop the disease.

III. Recombinant Nucleic Acids

Certain aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding a transglutaminase polypeptide (e.g., a human transglutaminase polypeptide). In some embodiments, present disclosure relates to recombinant nucleic acids (e.g., isolated recombinant nucleic acids) comprising one or more (e.g., one or more, two or more, three or more, four or more, five or more, ten or more, etc.) polynucleotides encoding a transglutaminase 1 (TGM1) polypeptide (e.g., a human TGM1 polypeptide). In some embodiments, the recombinant nucleic acid comprises one polynucleotide encoding a TGM1 polypeptide. In some embodiments, the recombinant nucleic acid comprises two polynucleotides encoding a TGM1 polypeptide.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant nucleic acid is a recombinant herpes simplex virus genome. In some embodiments, the recombinant herpes simplex virus genome is a recombinant type 1 herpes simplex virus (HSV-1) genome.

Polynucleotides Encoding Transglutaminase Polypeptides

In some embodiments, the present disclosure relates to a recombinant nucleic acid comprising one or more polynucleotides comprising the coding sequence of a transglutaminase gene. The coding sequence of any suitable transglutaminase gene (including any isoform thereof) known in the art may be encoded by a polynucleotide of the present disclosure, including, for example, a transglutaminase 1 (TGM1) gene (such as a human TGM1 gene, e.g., as disclosed by NCBI Gene ID: 7051; a mouse TGM1 gene, e.g., as disclosed by NCBI Gene ID: 21816; etc.), a transglutaminase 2 (TGM2) gene (such as a human TGM2 gene, e.g., as disclosed by NCBI Gene ID: 7052; a mouse TGM2 gene, e.g., as disclosed by NCBI Gene ID: 21817; etc.), a transglutaminase 3 (TGM3) gene (such as a human TGM3 gene, e.g., as disclosed by NCBI Gene ID: 7053; a mouse TGM3 gene, e.g., as disclosed by NCBI Gene ID: 21818; etc.), a transglutaminase 4 (TGM4) gene (such as a human TGM4 gene, e.g., as disclosed by NCBI Gene ID: 7047; a mouse TGM4 gene, e.g., as disclosed by NCBI Gene ID: 331046; etc.), a transglutaminase 5 (TGM5) gene (such as a human TGM5 gene, e.g., as disclosed by NCBI Gene ID: 9333; a mouse TGM5 gene, e.g., as disclosed by NCBI Gene ID: 74176), a transglutaminase 6 (TGM6) gene (such as a human TGM6 gene, e.g., as disclosed by NCBI Gene ID: 343641; a mouse TGM6 gene, e.g., as disclosed by NCBI Gene ID: 241636; etc.), a transglutaminase 7 (TGM7) gene (such as a human TGM7 gene, e.g., as disclosed by NCBI Gene ID: 116179; a mouse TGM7 gene, e.g., as disclosed by NCBI Gene ID: 640543; etc.), etc. Methods of identifying transglutaminase gene homologs/orthologs from additional species are known to one of ordinary skill in the art, including, for example, using a nucleic acid sequence alignment program such as the BLAST® blastn suite. In some embodiments, a polynucleotide of the preset disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the transglutaminase genes (and/or coding sequences thereof) described herein or known in the art. In some embodiments, a polynucleotide of the present disclosure comprises the coding sequence of a human transglutaminase gene (e.g., a human TGM1 gene, a human TGM2 gene, a human TGM3 gene, a human TGM4 gene, a human TGM5 gene, a human TGM6 gene, and/or a human TGM7 gene).

In some embodiments, a polynucleotide of the present disclosure comprises a codon-optimized variant of the coding sequence of any of the transglutaminase genes described herein or known in the art. In some embodiments, use a of a codon-optimized variant of the coding sequence of a transglutaminase gene increases stability and/or yield of heterologous expression (RNA and/or protein) of the encoded transglutaminase polypeptide in a target cell, as compared to the stability and/or yield of heterologous expression of a corresponding, non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, the present disclosure relates to one or more polynucleotides comprising the coding sequence of a TGM1 gene. Any suitable TGM1 gene (and/or the coding sequence thereof) known in the art may be encoded by a polynucleotide of the present disclosure, including, for example, a TGM1 gene from a human (see e.g., NCBI Gene ID: 7051; SEQ ID NO: 1), chimpanzee (see e.g., NCBI Gene ID: 452814), mouse (see e.g., NCBI Gene ID: 21816; SEQ ID NO: 3), rat (see e.g., NCBI Gene ID: 60335; SEQ ID NO: 4), dog (see e.g., NCBI Gene ID: 403630), rabbit (see e.g., NCBI Gene ID: 100009118), cow (see e.g., NCBI Gene ID: 407997), rhesus monkey (see e.g., NCBI Gene ID: 715854), hamster (see e.g., NCBI Gene ID: 101839516), etc. Methods of identifying TGM1 gene homologs/orthologs from additional species are known to one of ordinary skill in the art, including, for example, using a nucleic acid sequence alignment program such as the BLAST® blastn suite. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the TGM1 genes (and/or coding sequences thereof) described herein or known in the art.

In some embodiments, a polynucleotide of the present disclosure comprises the coding sequence of the human TGM1 gene.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 1. In some embodiments, a polynucleotide of the present disclosure comprises the sequence of SEQ ID NO: 1.

In some embodiments, a polynucleotide of the present disclosure comprises a 5' truncation, a 3' truncation, or a fragment of the sequence of SEQ ID NO: 1. In some embodiments, the 5' truncation, 3' truncation, or fragment of the sequence of SEQ ID NO: 1 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2100, at least 2200, at least 2300, at least 2400, but fewer than 2454, consecutive nucleotides of SEQ ID NO: 1. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-2451 of SEQ ID NO: 1. In some embodiments, a polynucleotide of the present disclosure comprises the sequence of nucleic acids 1-2451 of SEQ ID NO: 1.

In some embodiments, a polynucleotide of the present disclosure comprises the sequence of a codon-optimized variant of the human TGM1 gene.

In some embodiments, use of a codon-optimized variant increases stability and/or yield of heterologous TGM1 (RNA and/or protein) expressed in a target cell (such as a human keratinocyte), as compared to the stability and/or yield of heterologous expression of a corresponding non-codon-optimized, wild-type TGM1 sequence. Any suitable method known in the art for performing codon-optimization of a sequence for expression in one or more target cells (e.g., one or more human cells) may be used, including, for example, by the methods described by Fath et al. (PLoS One. 2011 Mar. 3; 6(3): e17596).

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 2. In some embodiments, a polynucleotide of the present disclosure comprises the sequence of SEQ ID NO: 2.

In some embodiments, a polynucleotide of the present disclosure comprises a 5' truncation, a 3' truncation, and/or a fragment of the sequence of SEQ ID NO: 2. In some embodiments, the 5' truncation, 3' truncation, and/or fragment of the sequence of SEQ ID NO: 2 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2100, at least 2200, at least 2300, at least 2400, but fewer than 2454, consecutive nucleotides of SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-2451 of SEQ ID NO: 2. In some embodiments, a polynucleotide of the present disclosure comprises the sequence of nucleic acids 1-2451 of SEQ ID NO: 2.

A polynucleotide of the present disclosure encoding a transglutaminase polypeptide may further encode additional coding and non-coding sequences. Examples of additional coding and non-coding sequences may include, but are not limited to, sequences encoding additional polypeptide tags (e.g., encoded in-frame with the transglutaminase polypeptide (e.g., the TGM1 polypeptide) in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance transglutaminase expression in specific cell types (such as human keratinocytes and/or fibroblasts).

In some embodiments, a polynucleotide of the present disclosure encoding a transglutaminase polypeptide is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, HSV chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the β-actin promoter), a ubiquitin promoter (e.g., a ubiquitin C (UbC) promoter), a phosphoglycerate kinase (PGK) promoter, an immunoglobulin promoter, from heat-shock promoters, and the like), promoters from homologous mammalian genes (e.g., native human transglutaminase promoters), synthetic promoters (such as the CAGG promoter, and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure is operably linked to one or more heterologous promoters. In some embodiments, the one or more heterologous promoters are one or more of constitutive promoters, tissue-specific promoters, temporal promoters, spatial promoters, inducible promoters and repressible promoters. In some embodiments, the one or more heterologous promoters are one or more of the human cytomegalovirus (HCMV) immediate early promoter, the human elongation factor-1 (EF1) promoter, the human β-actin promoter, the human UbC promoter, the human PGK promoter, the synthetic CAGG promoter, and any combinations thereof. In some embodiments, a polynucleotide of the present disclosure encoding a transglutaminase polypeptide is operably linked to an HCMV promoter.

In some embodiments, a polynucleotide of the present disclosure does not comprise the coding sequence of (e.g., a transgene encoding) a Collagen alpha-1 (VII) chain polypeptide (COLT). In some embodiments, a polynucleotide of the present disclosure does not comprise the coding sequence of (e.g., a transgene encoding) a Lysyl hydroxylase 3 polypeptide (LH3). In some embodiments, a polynucleotide of the present disclosure does not comprise the coding sequence of (e.g., a transgene encoding) a Keratin type I cytoskeletal 17 polypeptide (KRT17). In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptide thereof.

Transglutaminase Polypeptides

In some embodiments, the present disclosure relates to one or more polynucleotides encoding a full-length transglutaminase polypeptide or any portions thereof. Any suitable transglutaminase polypeptide known in the art may be encoded by a polynucleotide of the present disclosure, including, for example, a transglutaminase 1 (TGM1) polypeptide (such as a human TGM1 polypeptide, e.g., as disclosed by UniProt accession number: P22735; a mouse TGM1 polypeptide, e.g., as disclosed by UniProt accession number: Q9JLF6; etc.), a transglutaminase 2 (TGM2) polypeptide (such as a human TGM2 polypeptide, e.g., as disclosed by UniProt accession number: P21980; a mouse TGM2 polypeptide, e.g., as disclosed by UniProt accession number: P21981; etc.), a transglutaminase 3 (TGM3) polypeptide (such as a human TGM3 polypeptide, e.g., as disclosed by UniProt accession number: Q08188; a mouse TGM3 polypeptide, e.g., as disclosed by UniProt accession number: Q08189; etc.), a transglutaminase 4 (TGM4) polypeptide (such as a human TGM4 polypeptide, e.g., as disclosed by UniProt accession number: P49221; a mouse TGM4 polypeptide, e.g., as disclosed by UniProt accession number Q8BZH1; etc.), a transglutaminase 5 (TGMS) polypeptide (such as a human TGMS polypeptide, e.g., as disclosed by UniProt accession number: O43548; a mouse TGMS polypeptide, e.g., as disclosed by UniProt accession number: Q9D7I9; etc.), a transglutaminase 6 (TGM6) polypeptide (such as a human TGM6 polypeptide, e.g., as disclosed by UniProt accession number: O95932; a mouse TGM6 polypeptide, e.g., as disclosed by UniProt accession number: Q6YCI4; etc.), a transglutaminase 7 (TGM7) polypeptide (such as a human TGM7 polypeptide, e.g., as disclosed by UniProt accession number: Q96PF1; a mouse TGM7 polypeptide, e.g., as disclosed by UniProt accession number A2ART8; etc.), etc. Methods of identifying transglutaminase polypeptide homologs/orthologs from additional species are known to one of ordinary skill in the art, including, for example, using an amino acid sequence alignment program such as the BLAST® blastp suite or OrthoDB. In some embodiments, a transglutaminase polypeptide of the preset disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the transglutaminase polypeptides described herein or known in the art. In some embodiments, a polynucleotide of the present disclosure encodes a human transglutaminase polypeptide (e.g., a human TGM1 polypeptide, a human TGM2 polypeptide, a human TGM3 polypeptide, a human TGM4 polypeptide, a human TGM5 polypeptide, a human TGM6 polypeptide, and/or a human TGM7 polypeptide).

In some embodiments, the present disclosure relates to one or more polynucleotides encoding a TGM1 polypeptide. Any suitable TGM1 polypeptide known in the art may be encoded by a polynucleotide of the present disclosure, including, for example, a TGM1 polypeptide from a human (see e.g., UniProt accession number P22735; SEQ ID NO: 5), chimpanzee (see e.g., UniProt accession number H2Q827; SEQ ID NO: 8), mouse (see e.g., UniProt accession number Q9JLF6; SEQ ID NO: 6), rat (see e.g., UniProt accession number P23606; SEQ ID NO: 7), dog (see e.g., UniProt accession number Q9GLK0; SEQ ID NO: 10), rabbit (see e.g., UniProt accession number P22758; SEQ ID NO: 9), etc. Methods of identifying TGM1 polypeptide homologs/orthologs from additional species are known to one of ordinary skill in the art, including, for example, using an amino acid sequence alignment program such as the BLAST® blastp suite or OrthoDB. In some embodiments, a polynucleotide encoding a TGM1 polypeptide is a polynucleotide that encodes a polypeptide comprising a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the of any of the TGM1 polypeptides described herein or known in the art.

In some embodiments, a polynucleotide of the present disclosure encodes a human TGM1 polypeptide. In some embodiments, a TGM1 polypeptide of the present disclosure is a human TGM1 polypeptide.

In some embodiments, a polynucleotide encoding a TGM1 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 5. In some embodiments, a polynucleotide encoding a human TGM1 polypeptide is a polynucleotide that encodes a polypeptide comprising the amino acid sequence of SEQ ID NO: 5.

In some embodiments, a polynucleotide encoding a TGM1 polypeptide is a polynucleotide that encodes an N-terminal truncation, a C-terminal truncation, or a fragment of the amino acid sequence of SEQ ID NO: 5. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, but fewer than 817, consecutive amino acids of SEQ ID NO: 5.

In some embodiments, a polynucleotide of the present disclosure encoding a transglutaminase polypeptide (e.g., a human TGM1 polypeptide) expresses the transglutaminase polypeptide when the polynucleotide is delivered into one or more target cells of a subject (e.g., one or more cells of the epidermis of the subject). In some embodiments, expression of the transglutaminase polypeptide (e.g., a human TGM1 polypeptide) enhances, increases, augments, and/or supplements the levels, function, and/or activity of the transglutaminase polypeptide in one or more target cells of a subject (e.g., as compared to prior to expression of the transglutaminase polypeptide). In some embodiments, expression of the transglutaminase polypeptide (e.g., a human TGM1 polypeptide) enhances production of cornified cell envelopes and/or stabilized the stratum corneum of the skin of the subject (e.g., as compared to prior to expression of the transglutaminase polypeptide). In some embodiments, expression of the transglutaminase polypeptide (e.g., a human TGM1 polypeptide) treats a barrier function defect in the subject (e.g., as compared to prior to expression of the transglutaminase polypeptide). In some embodiments, expression of the transglutaminase polypeptide (e.g., a human TGM1 polypeptide) provides prophylactic, palliative, or therapeutic relief to one or more signs or symptoms of a transglutaminase deficiency in the subject (e.g., as compared to prior to expression of the transglutaminase polypeptide). In some embodiments, expression of the transglutaminase polypeptide (e.g., a human TGM1 polypeptide) provides prophylactic, palliative, or therapeutic relief of one or more signs or symptoms of autosomal recessive congenital ichthyosis (e.g., LI and/or NCIE) in the subject (e.g., as compared to prior to expression of the transglutaminase polypeptide).

Recombinant Nucleic Acids

In some embodiments, the present disclosure relates to recombinant nucleic acids comprising any one or more of the polynucleotides described herein. In some embodiments, the recombinant nucleic acid is a vector (e.g., an expression vector, a display vector, etc.). In some embodiments, the vector is a DNA vector or an RNA vector. Generally, vectors suitable to maintain, propagate, or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector is cannot integrate into a host DNA (e.g., is episomal). Methods of making vectors containing one or more polynucleotides of interest are well known to one of ordinary skill in the art, including, for example, by chemical synthesis or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". Viruses 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or any derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding, wild-type herpes virus genome). In some embodiments, the recombinant herpes virus genome is replication-competent. In some embodiments, the recombinant herpes virus genome is replication-defective.

In some embodiments, the recombinant nucleic acid is a recombinant herpes simplex (HSV) virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof. In some embodiments, the recombinant herpes simplex virus genome is a recombinant HSV-1 genome. In some embodiments, the recombinant herpes simplex virus genome is replication-competent. In some embodiments, the recombinant herpes simplex virus genome is replication-defective. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 and/or ICP47 herpes simplex virus genes (e.g., to avoid production of an immune-stimulating virus). In some embodiments, the recombinant herpes simplex virus genome does not comprise an inactivating mutation in the ICP34.5 herpes simplex virus gene (one or both copies). In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an initiating mutation in the ICP4 (one or both copies) ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP4 gene (one or both copies), and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0 (one or both copies), ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long (IRL) and internal repeat short (IRS) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP22 gene. In some embodiments, the recombinant herpes simplex virus genome comprises an inactivating mutation in the ICP4 gene (one or both copies), and an inactivating mutation in the ICP22 gene. In some embodiments, the inactivating mutation is a deletion of the coding sequence of the ICP4 (one or both copies) and/or ICP22 genes. In some embodiments, the recombinant herpes simplex virus genome further comprises an inactivating mutation in the ICP0, ICP27, ICP47, and/or UL41 genes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 and/or UL41 genes.

In some embodiments, the recombinant herpes simplex virus genome comprises an inactivating mutation in the ICP0 (one or both copies) gene. In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0 (one or both copies), ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and UL55 herpes simplex viral gene loci. In some embodiments, a recombinant herpes simplex virus genome comprises one or more polynucleotides of the present disclosure within one or both of the viral ICP4 gene loci (e.g., a recombinant virus carrying a polynucleotide encoding a transglutaminase (e.g., human TGM1) in one or both of the ICP4 loci). In some embodiments, a recombinant herpes simplex virus genome comprises one or more polynucleotides of the present disclosure within the viral ICP22 gene locus (e.g., a recombinant virus carrying a polynucleotide encoding a transglutaminase (e.g., human TGM1) in the ICP22 locus). In some embodiments, a recombinant herpes simplex virus genome comprises one or more polynucleotides of the present disclosure within the viral UL41 gene locus (e.g., a recombinant virus carrying a polynucleotide encoding a transglutaminase (e.g., human TGM1) in the UL41 locus). In some embodiments, a recombinant herpes simplex virus genome comprises one or more polynucleotides of the present disclosure within the viral ICP47 gene locus (e.g., a recombinant virus carrying a polynucleotide encoding a transglutaminase (e.g., human TGM1) in the ICP47 locus). In some embodiments, a recombinant herpes simplex virus genome comprises one or more polynucleotides of the present disclosure within one or more of the viral ICP4 gene loci, and one or more polynucleotides of the present disclosure within the viral ICP22 and/or UL41 gene locus (e.g., a recombinant virus carrying a polynucleotide encoding a transglutaminase (e.g., human TGM1) in one or both of the ICP4 loci, and a polynucleotide encoding a transglutaminase (e.g., human TGM1) in the ICP22 and/or UL41 locus).

In some embodiments, the recombinant herpes virus genome (e.g., a recombinant herpes simplex virus genome) has been engineered to decrease or eliminate expression of one or more toxic herpes virus genes (such as one or both copies of the HSV ICP0 gene, one or both copies of the HSV ICP4 gene, and/or the HSV ICP22 gene). In some embodiments, the recombinant herpes virus genome (e.g., a recombinant herpes simplex virus genome) has been engineered to reduce cytotoxicity of the recombinant genome when introduced into a target cell, as compared to a corresponding wild-type herpes virus genome (e.g., a wild-type herpes simplex virus genome). In some embodiments, cytotoxicity (e.g., in human keratinocytes and/or fibroblast cells) of the recombinant herpes virus genome (e.g., a recombinant simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). In some embodiments, cytotoxicity (e.g., in human keratinocytes and/or fibroblast cells) of the recombinant herpes virus genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant herpes virus genome (e.g., a recombinant herpes simplex virus genome) has been engineered to reduce its impact on host cell proliferation after exposure of the target cell to the recombinant genome, as compared to a corresponding wild-type herpes virus genome (e.g., a wild-type herpes simplex virus genome). In some embodiments, the target cell is a human cell. In some embodiments, the target cell is a cell of the epidermis and/or dermis. In some embodiments, the target cell is a keratinocyte. In some embodiments, host cell proliferation (e.g., human keratinocytes and/or fibroblast cells) after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). In some embodiments, host cell proliferation (e.g., human keratinocytes and/or fibroblast cells) after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). Methods of measuring cellular proliferation are known to one of ordinary skill in the art, including, for example, through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, a recombinant nucleic acid of the present disclosure (e.g., a recombinant herpes simplex virus genome) comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide. In some embodiments, the recombinant nucleic acid comprises one or more polynucleotides encoding a TGM1 polypeptide (e.g., a human TGM1 polypeptide). In some embodiments, the vector comprises a single polynucleotide encoding a TGM1 polypeptide. In some embodiments, the recombinant nucleic acid comprises two polynucleotides each encoding a TGM1 polypeptide. In some embodiments, the recombinant nucleic acid comprises three polynucleotides each encoding a TGM1 polypeptide, etc.

IV. Viruses

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human). In some embodiments, the one or more target cells are one or more human cells. In some embodiments, the one or more target cells are one or more cells with a transglutaminase deficiency (e.g., one or more cells comprising a genomic mutation in native TGM1). In some embodiments, the one or more target cells are one or more cells of the skin (e.g., one or more cells of the epidermis, dermis, and/or subcutis). In some embodiments, the one or more cells are selected from keratinocytes, melanocytes, Langerhans cells, Merkel cells, mast cells, fibroblasts, and/or adipocytes. In some embodiments, the one or more cells are keratinocytes. In some embodiments, the one or more cells reside in the stratum corneum, stratum granulosum, stratum spinulosum, stratum basale, and/or basement membrane.

Any suitable virus known in the art may be used, including, for example, adenovirus, adeno-associated virus, retrovirus, lentivirus, sendai virus, herpes virus (e.g., a herpes simplex virus), vaccinia virus, and/or any hybrid virus thereof. In some embodiments, the virus is attenuated. In some embodiments, the virus is replication-defective. In some embodiments, the virus is replication-competent. In some embodiments, the virus has been modified to alter its tissue tropism relative to the tissue tropism of an unmodified, wild-type virus. In some embodiments, the virus has reduced cytotoxicity as compared to a corresponding wild-type virus Methods for producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, and a Kaposi's sarcoma-associated herpesvirus, etc. In some embodiments, the herpes virus is attenuated. In some embodiments, the herpes virus is replication-defective. In some embodiments, the herpes virus is replication-competent. In some embodiments, the herpes virus has reduced cytotoxicity as compared to a corresponding wild-type herpes virus. In some embodiments, the herpes virus is not oncolytic.

In some embodiments, the virus is a herpes simplex virus. Herpes simplex viruses comprising recombinant nucleic acids may be produced by a process disclosed, for example, in WO2015/009952 and/or WO2017/176336. In some embodiments, the herpes simplex virus is attenuated. In some embodiments, the herpes simplex virus is replication-competent. In some embodiments, the herpes simplex virus is replication-defective. In some embodiments, the herpes simplex virus is a herpes simplex type 1 virus (HSV-1), a herpes simplex type 2 virus (HSV-2), of any derivatives thereof. In some embodiments, the herpes simplex virus is a herpes simplex type 1 virus (HSV-1). In some embodiments, the HSV-1 is attenuated. In some embodiments, the HSV-1 has reduced cytotoxicity as compared to a corresponding wild-type HSV-1. In some embodiments, the HSV-1 is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus) for one or more target cells (e.g., one or more human keratinocytes and/or fibroblasts) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more human keratinocytes and/or fibroblasts) is about 85% to about 100%. In some embodiments, the virus is a herpes simplex virus and the transduction efficiency of the virus for one or more target cells (e.g., one or more human keratinocytes and/or fibroblasts) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

V. Pharmaceutical Compositions and Formulations

Certain aspects of the present disclosure relate to pharmaceutical compositions and formulations comprising a recombinant nucleic acid (e.g., a recombinant herpes virus genome) and/or virus (e.g., a herpes virus comprising a recombinant genome) described herein (such as a herpes simplex virus comprising a recombinant herpes simplex virus genome), and a pharmaceutically acceptable excipient or carrier.

In some embodiments, the pharmaceutical composition or formulation comprises any one or more of the viruses (e.g., herpes viruses) as described herein. In some embodiments, the pharmaceutical composition or formulation comprises from about $10^4$ to about $10^{12}$ plaque forming units (PFU)/mL of the virus. For example, the pharmaceutical composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about $10^8$, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the pharmaceutical composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Pharmaceutical compositions and formulations can be prepared by mixing the active ingredient(s) (such as a recombinant nucleic acid or a virus) having the desired degree of purity with one or more pharmaceutically acceptable carriers or excipients. Pharmaceutically acceptable carriers or excipients are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 10% glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); and/or non-ionic surfactants (such as polyethylene glycol (PEG)). A thorough discussion of pharmaceutically acceptable carriers is available in REMINGTON'S PHARMACEUTICAL SCIENCES (Mack Pub. Co., N.J. 1991).

In some embodiments, the pharmaceutical composition or formulation comprises one or more lipid (e.g., cationic lipid) carriers. In some embodiments, the pharmaceutical composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics) for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions described herein may be any type of biocompatible nanoparticle known in the art, including, for example, nanoparticles comprising poly(lactic acid), poly (glycolic acid), PLGA, PLA, PGA, and any combinations thereof (see e.g., Vauthier et al. Adv Drug Del Rev. (2003) 55: 519-48; US2007/0148074; US2007/0092575; US2006/0246139; U.S. Pat. Nos. 5,753,234; 7,081,483; and WO2006/052285).

In some embodiments, the pharmaceutically acceptable carrier or excipient may be adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutically acceptable carrier or excipient is adapted for or suitable for cutaneous, topical, transdermal, subcutaneous, and/or intradermal administration. In some embodiments, the pharmaceutically acceptable carrier or excipient is adapted for or suitable for topical, transdermal, and/or intradermal administration.

Examples of carriers or excipients adapted for or suitable for use in a topical, transdermal, and or intradermal application/administration may include, but are not limited to, ointments, pastes, creams, suspensions, emulsions, fatty ointments, gels, powders, lotions, solutions, sprays, patches, microneedle arrays, and inhalants. In some embodiments, the pharmaceutically acceptable carrier or excipient comprises one or more (e.g., one or more, two or more, three or more, four or more, five or more, etc.) of an ointment, paste, cream, suspension, emulsion, fatty ointment, gel, powder, lotion, solution, spray, and an inhalant. In some embodiments, the pharmaceutical carrier comprises a patch (e.g. a patch that adheres to the skin). In some embodiments, the pharmaceutically acceptable carrier comprises a microneedle array. Methods for making and using microneedle arrays suitable for pharmaceutical composition delivery are generally known in the art (Kim Y. et al. "Microneedles for drug and vaccine delivery". *Advanced Drug Delivery Reviews* 2012, 64 (14): 1547-68).

In some embodiments, the pharmaceutical composition or formulation is adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutical composition or formulation is adapted for or suitable for cutaneous, topical, transdermal, subcutaneous, and/or intradermal administration. In some embodiments, the pharmaceutical composition or formulation is adapted for or suitable for topical, transdermal, and/or intradermal administration.

In some embodiments, the pharmaceutical composition or formulation further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the pharmaceutical composition or formulation comprises a hydroxypropyl methylcellulose gel. In some embodiments, the pharmaceutical composition or formulation comprises a phosphate buffer. In some embodiments, the pharmaceutical composition or formulation comprises glycerol (e.g., at about 1%, about 2%, about 3%, about 4%, about 5%, about 6%, about 7%, about 8%, about 9%, about 10%, about 15%, etc.).

Pharmaceutical compositions and formulations to be used for in vivo administration are generally sterile. Sterility may be readily accomplished, e.g., by filtration through sterile filtration membranes.

In some embodiments, any of the recombinant nucleic acids, viruses, and/or pharmaceutical compositions or formulations described herein may be used to deliver one or more polynucleotides encoding a transglutaminase polypeptide (e.g., a human TGM1 polypeptide) into one or more cells of a subject (e.g., one or more transglutaminase-deficient cells, one or more cells harboring a TGM1 gene mutation, etc.). In some embodiments, any of the recombinant nucleic acids, viruses, and/or pharmaceutical compositions or formulations described herein may be used in a therapy. In some embodiments, any of the recombinant nucleic acids, viruses, and/or pharmaceutical compositions or formulations described herein may be used in the treatment of a disease or condition that would benefit from the expression of a transglutaminase polypeptide (e.g., a disease or condition associated with a transglutaminase deficiency (such as TGM1-deficient ARCI), a disease or condition associated a TGM1 gene mutation, etc.). In some embodiments, any of the recombinant nucleic acids, viruses, and/or pharmaceutical compositions or formulations described herein may be used in the treatment of ARCI (e.g., used in the treatment of LI or NCIE). In some embodiments, any of the recombinant nucleic acids, viruses, and/or pharmaceutical compositions or formulations described herein may be used in the treatment of lamellar ichthyosis.

In some embodiments, any of the recombinant nucleic acids, viruses, and/or pharmaceutical compositions or formulations described herein may be used in the preparation or manufacture of a medicament. In some embodiments, any of the recombinant nucleic acids, viruses, and/or pharmaceutical compositions or formulations described herein may be used in the preparation or manufacture of a medicament useful for delivering one or more polynucleotides encoding a transglutaminase polypeptide (e.g., a human TGM1 polypeptide) into one or more cells of a subject (e.g., one or more transglutaminase-deficient cells, one or more cells harboring a TGM1 gene mutation, etc.). In some embodiments, any of the recombinant nucleic acids, viruses, and/or pharmaceutical compositions or formulations described herein may be used in the preparation or manufacture of a medicament useful for the treatment of a disease or condition that would benefit from the expression of a transglutaminase polypeptide (e.g., a disease or condition associated with a transglutaminase deficiency (such as TGM1-deficient ARCI), a disease or condition associated a TGM1 gene mutation, etc.). In some embodiments, any of the recombinant nucleic acids, viruses, and/or pharmaceutical compositions or formulations described herein may be used in the preparation or manufacture of a medicament useful for the treatment of a TGM1 deficiency and/or ARCI (e.g., useful for the treatment of LI or NCIE). In some embodiments, any of the recombinant nucleic acids, viruses, and/or pharmaceutical compositions or formulations described herein may be used in the preparation or manufacture of a medicament useful for the treatment of lamellar ichthyosis.

VI. Methods

Certain aspects of the present disclosure relate to enhancing, increasing, augmenting, and/or supplementing the levels of a transglutaminase polypeptide (e.g., a human TGM1 polypeptide) in one or more cells of a subject comprising administering to the subject any of the recombinant nucleic acids, viruses, medicaments, and/or pharmaceutical compositions described herein. In some embodiments, the subject is a human. In some embodiments, the subject suffers from autosomal recessive congenital ichthyosis (ARCI). In some embodiments, the subject suffers from lamellar ichthyosis (LI) and/or non-bullous congenital ichthyosiform erythroderma (NCIE). In some embodiments, the subject's genome comprises a mutation (e.g., a loss-of-function mutation) in an endogenous transglutaminase gene (one or both copies), such as a homozygous loss-of-function mutation in the TGM1 gene. In some embodiments, the recombinant nucleic acid, virus, medicament, and/or pharmaceutical composition is administered cutaneously, topically, transdermally, subcutaneously, or intradermally to the subject. In some embodiments, the recombinant nucleic acid, virus, medicament, and/or pharmaceutical composition is administered one, two three, four, five or more times per day. In some embodiments, the recombinant nucleic acid, virus, medicament, and/or pharmaceutical composition is administered to one or more affected and/or unaffected areas of the subject. In some embodiments, one or more portions of the skin of the subject is abraded or made more permeable prior to treatment. Any suitable method of abrading the skin or increasing skin permeability known in the art may be used, including, for example, use of a dermal roller, repeated use of adhesive strips to remove layers of skin cells, scraping with a scalpel or blade, use of sandpaper, use of chemical permeation enhancers or electrical energy, use of sonic or ultrasonic energy, use of light (e.g., laser) energy, use of micron-sized needles or blades with a length suitable to pierce but not completely pass through the epidermis, etc.

In some embodiments, administration of the recombinant nucleic acid, virus, medicament, and/or pharmaceutical composition to the subject increases transglutaminase (e.g., TGM1) levels (transcript or protein levels) by at least about 2-fold in one or more contacted or treated cells of the subject, as compared to the endogenous levels of the transglutaminase in one or more corresponding untreated cells in the subject. For example, administration of the recombinant nucleic acid, virus, medicament, and/or pharmaceutical composition may increase transglutaminase (e.g., TGM1) levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of the transglutaminase in one or more corresponding untreated cells in the subject. In some embodiments, the one or more contacted or treated cells are one or more cells of the epidermis (e.g., a keratinocyte). Methods of measuring transcript or protein levels from a sample are well known to one of ordinary skill in the art, including, for example, but qPCR, western blot, mass spectrometry, etc.

Other aspects of the present disclosure relate to a method of enhancing production of cornified cell envelopes and/or stabilizing the stratum corneum layer of the skin of a subject in need thereof comprising administering to the subject any of the recombinant nucleic acids, viruses, medicaments, and/or pharmaceutical compositions described herein. In some embodiments, the subject is a human. In some embodiments, the subject suffers from autosomal recessive congenital ichthyosis (ARCI). In some embodiments, the subject suffers from lamellar ichthyosis (LI) and/or non-bullous congenital ichthyosiform erythroderma (NCIE). In some embodiments, the subject's genome comprises a mutation (e.g., a loss-of-function mutation) in an endogenous transglutaminase gene (one or both copies), such as a homozygous loss-of-function mutation in the TGM1 gene. In some embodiments, the recombinant nucleic acid, virus, medicament, and/or pharmaceutical composition is administered cutaneously, topically, transdermally, subcutaneously, or intradermally to the subject. In some embodiments, the recombinant nucleic acid, virus, medicament, and/or pharmaceutical composition is administered topically to the subject. In some embodiments, the recombinant nucleic acid, virus, medicament, and/or pharmaceutical composition is administered one, two three, four, five or more times per day. In some embodiments, the recombinant nucleic acid, virus, medicament, and/or pharmaceutical composition is administered to one or more affected and/or unaffected areas of the subject. Methods of monitoring changes/improvements in the production of cornified cell envelopes and/or stabilization of the stratum corneum are known in the art, including, for example, by microscopic evaluation.

Other aspects of the present disclosure relate to a method of treating a barrier function defect in a subject in need thereof comprising administering to the subject any of the recombinant nucleic acids, viruses, medicaments, and/or pharmaceutical compositions described herein. In some embodiments, the barrier function defect is transepidermal water loss (TEWL). In some embodiments, administering ay of the recombinant nucleic acids, viruses, medicaments, and/or pharmaceutical compositions to the subject reduces transepidermal water loss in the subject. In some embodiments, the subject is a human. In some embodiments, the subject suffers from autosomal recessive congenital ichthyosis (ARCI). In some embodiments, the subject suffers from lamellar ichthyosis (LI) and/or non-bullous congenital ichthyosiform erythroderma (NCIE). In some embodiments, the subject's genome comprises a mutation (e.g., a loss-of-function mutation) in an endogenous transglutaminase gene (one or both copies), such as a homozygous loss-of-function mutation in the TGM1 gene. In some embodiments, the recombinant nucleic acid, virus, medicament, and/or pharmaceutical composition is administered cutaneously, topically, transdermally, subcutaneously, or intradermally to the subject. In some embodiments, the recombinant nucleic acid, virus, medicament, and/or pharmaceutical composition is administered topically to the subject. In some embodiments, the recombinant nucleic acid, virus, medicament, and/or pharmaceutical composition is administered one, two three, four, five or more times per day. In some embodiments, the recombinant nucleic acid, virus, medicament, and/or pharmaceutical composition is administered to one or more affected and/or unaffected areas of the subject. Methods of measuring barrier function, including TEWL, are known in the art, including, for example, by any of the methods described by Antonov et al. (Curr Probl Dermatol. 2016; 49:61-70).

Other aspects of the present disclosure relate to a method of providing prophylactic, palliative, or therapeutic relief to one or more signs or symptoms of autosomal recessive congenital ichthyosis (ARCI) in a subject in need thereof comprising administering to the subject any of the recombinant nucleic acids, viruses, medicaments, and/or pharmaceutical compositions described herein. In some embodiments, the subject is a human. In some embodiments, the subject suffers from lamellar ichthyosis (LI) and/or non-bullous congenital ichthyosiform erythroderma (NCIE). In some embodiments, the subject's genome comprises a mutation (e.g., a loss-of-function mutation) in an endogenous transglutaminase gene (one or both copies), such as a homozygous loss-of-function mutation in the TGM1 gene. In some embodiments, the recombinant nucleic acid, virus, medicament, and/or pharmaceutical composition is administered cutaneously, topically, transdermally, subcutaneously, or intradermally to the subject. In some embodiments, the recombinant nucleic acid, virus, medicament, and/r pharmaceutical composition is administered topically to the subject. In some embodiments, the recombinant nucleic acid, virus, medicament, and/or pharmaceutical composition is administered one, two three, four, five or more times per day. In some embodiments, the recombinant nucleic acid, virus, medicament, and/or pharmaceutical composition is administered to one or more affected and/or unaffected areas of the subject. In some embodiments, the methods of the present disclosure lead to one or more positive outcomes in a subject suffering from ARCI. Any method known in the art for measuring positive outcomes in a subject suffering from ARCI may be used, including, for example, by measuring: a reduction (e.g., a 50% reduction, a 75% reduction, etc.) in Ichthyosis Area Severity Index (IASI); a change in IASI-E and/or IASI-S; a reduction (e.g., a 2-point reduction) in Congenital Ichthyosis Severity Index (CISI) for skin redness, erythema, hyperkeratosis, and/or scaling; a reduction in Bodemer score; a reduction (e.g., a 3-point reduction) in subject-reported itch and/or pain; a reduction in Dermatology Life Quality Index (DLQI); a reduction in the iQoL-32 index; an improvement in the 5-D itch score; and/or a reduction in TEWL.

In some embodiments, the recombinant nucleic acids, viruses, medicaments, and/or pharmaceutical compositions or formulations described herein may be used to treat or alleviate one or more signs or symptoms of ARCI. Signs and/or symptoms of ARCI may include, but are not limited to an abnormal stratum corneum, incomplete thickening of the cornified cell envelope, defects in the intercellular lipid layers in the stratum corneum, generalized scaling with variable redness of the skin, formation of large plate-like scales, accelerated epidermal turnover, palmoplantar hyperkeratosis, defective barrier function, recurrent skin infections, exposure keratitis, hypohidrosis, heat intolerance, corneal perforation, rickets, nail abnormalities, dehydration, respiratory problems, ectropion, eclabium, hypoplasia of joint and nasal cartilage, and/or scarring alopecia.

The recombinant nucleic acids, viruses, medicaments, and/or pharmaceutical compositions or formulations described herein may be administered by any suitable method or route known in the art, including, without limitation, by oral administration, sublingual administration, buccal administration, topical administration, rectal administration, via inhalation, transdermal administration, subcutaneous injection, intradermal injection, intravenous (IV) injection, intra-arterial injection, intramuscular injection, intracardiac injection, intraosseous injection, intraperitoneal injection, transmucosal administration, vaginal administration, intravitreal administration, intraorbital administration, subretinal administration, intra-articular administration, peri-articular administration, local administration, epicutaneous administration, or any combinations thereof. The present disclosure thus encompasses methods of delivering any of the recombinant nucleic acids, viruses, medicaments, and/or pharmaceutical compositions or formulations described herein to an individual (e.g., an individual having, or at risk of developing, one or more signs or symptoms of lamellar ichthyosis).

In some embodiments, the recombinant nucleic acids, viruses, medicaments, and/or pharmaceutical compositions are administered intradermally and/or subcutaneously. In some embodiments, the recombinant nucleic acids, viruses, medicaments, and/or pharmaceutical compositions are administered topically and/or transdermally. In some embodiments, the recombinant nucleic acids, viruses, medicaments, and/or pharmaceutical compositions are administered one, two, three, four, five or more times per day. In some embodiments, the recombinant nucleic acids, viruses, medicaments, and/or pharmaceutical compositions are administered to one or more affected areas of an individual. In some embodiments, the recombinant nucleic acids, viruses, medicaments, and/or pharmaceutical compositions are administered to one or more unaffected areas of the individual.

In some embodiments, the polynucleotide encoding a TGM1 polypeptide expresses the TGM1 polypeptide when the polynucleotide is delivered into one or more target cells of a subject. In some embodiments, expression of the TGM1 polypeptide enhances, increases, augments, and/or supplements the levels of TGM1 polypeptide in one or more target cells. In some embodiments, expression of the TGM1 polypeptide enhances, increases, augments, and/or supplements the function of endogenous TGM1 polypeptide in one or more target cells. In some embodiments, expression of the TGM1 polypeptide enhances, increases, augments, and/or supplements the activity of a TGM1 polypeptide in one or more target cells. In some embodiments, expression of the TGM1 polypeptide enhances, increases, augments, and/or supplements the production of cornified cell envelopes in the subject. In some embodiments, expression of the TGM1 polypeptide stabilizes the stratum corneum layer of the skin of a subject. In some embodiments, expression of the TGM1 polypeptide enhances, increases, augments, and/or supplements the integrity and/or protective barrier function of the skin of the subject.

VII. Host Cells

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), Serratia (e.g., *S. marcescans*), and Shigella, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NS0 and Sp2/0. In some embodiments, the host cell is a human or non-human primate cell. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1 hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in WO2015/009952 and/or WO2017/176336.

VIII. Articles of Manufacture or Kits

Certain aspects of the present disclosure relate to an article of manufacture or a kit comprising any of the recombinant nucleic acids, viruses, medicaments, and/or pharmaceutical compositions or formulations described herein. In some embodiments, the article of manufacture or kit comprises a package insert comprising instructions for administering the recombinant nucleic acid, virus, medicament, and/or pharmaceutical composition or formulation to treat a transglutaminase deficiency (e.g., in a subject harboring a homozygous TGM1 loss-of-function mutation) and/or to provide prophylactic, palliative, or therapeutic relief to one or more signs or symptoms of ARCI (e.g., LI or NCIE).

Suitable containers for the recombinant nucleic acids, viruses, medicaments, and/or pharmaceutical compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, needles, syringes, package inserts, and the like.

IX. Enumerated Embodiments

Embodiment 1: A pharmaceutical composition comprising: (a) a herpes simplex virus (HSV) comprising a recombinant nucleic acid, wherein the recombinant nucleic acid comprises on or more polynucleotides encoding a Transglutaminase 1 (TGM) polypeptide; and (b) a pharmaceutically acceptable carrier.

Embodiment 2: The pharmaceutical composition of embodiment 1, wherein the recombinant nucleic acid comprises two or more polynucleotides encoding a TGM1 polypeptide.

Embodiment 3: The pharmaceutical composition of embodiment 1 or embodiment 2, wherein the HSV is replication-defective.

Embodiment 4: The pharmaceutical composition of embodiment 1 or embodiment 2, wherein the HSV is replication-competent.

Embodiment 5: The pharmaceutical composition of any one of embodiments 1-4, wherein the HSV is a herpes simplex type 1 virus, a herpes simplex type 2 virus, or any derivatives thereof.

Embodiment 6: The pharmaceutical composition of any one of embodiments 1-5, wherein the recombinant nucleic acid is a herpes simplex virus amplicon.

Embodiment 7: The pharmaceutical composition of embodiment 6, wherein the herpes simplex virus amplicon is an HSV-1 amplicon or an HSV-1 hybrid amplicon.

Embodiment 8: The pharmaceutical composition of embodiment 7, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 9: The pharmaceutical composition of any one of embodiments 1-5, wherein the recombinant nucleic acid is a recombinant herpes simplex virus genome.

Embodiment 10: The pharmaceutical composition of embodiment 9, wherein the recombinant herpes simplex virus genome is a recombinant HSV-1 genome, a recombinant HSV-2 genome, or any derivatives thereof.

Embodiment 11: The pharmaceutical composition of embodiment 9 or embodiment 10, wherein the recombinant herpes simplex virus genome comprises an inactivating mutation in a herpes simplex virus gene.

Embodiment 12: The pharmaceutical composition of embodiment 11, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 13: The pharmaceutical composition of embodiment 12, wherein the recombinant herpes simplex virus genome comprises an inactivation mutation in one or both copies of the ICP4 gene.

Embodiment 14: The pharmaceutical composition of embodiment 12 or embodiment 13, wherein the recombinant herpes simplex virus genome comprises an inactivating mutation in the ICP22 gene.

Embodiment 15: The pharmaceutical composition of any one of embodiments 12-14, wherein the recombinant herpes simplex virus genome comprises an inactivating mutation in the UL41 gene.

Embodiment 16: The pharmaceutical composition of any one of embodiments 12-15, wherein the recombinant herpes simplex virus genome comprises an inactivating mutation in the ICP0 gene.

Embodiment 17: The pharmaceutical composition of any one of embodiments 12-16, wherein the recombinant herpes simplex virus genome comprises an inactivating mutation in the ICP27 gene.

Embodiment 18: The pharmaceutical composition of any one of embodiments 11-17, wherein the inactivating mutation is a deletion of the coding sequence of the gene(s).

Embodiment 19: The pharmaceutical composition of any one of embodiments 9-18, wherein the recombinant herpes simplex virus genome comprises the one or more polynucleotides within one or more viral gene loci.

Embodiment 20: The pharmaceutical composition of any one of embodiments 9-19, wherein the recombinant herpes simplex virus genome comprises the one or more polynucleotides within one or both of the ICP4 viral gene loci.

Embodiment 21: The pharmaceutical composition of any one of embodiments 9-20, wherein the recombinant herpes simplex virus genome comprises the one or more polynucleotides within the ICP22 viral gene locus.

Embodiment 22: The pharmaceutical composition of any one of embodiments 9-21, wherein the recombinant herpes simplex virus genome comprises the one or more polynucleotides within the UL41 viral gene locus.

Embodiment 23: The pharmaceutical composition of any one of embodiments 1-22, wherein the HSV has reduced cytotoxicity as compared to a wild-type herpes simplex virus.

Embodiment 24: The pharmaceutical composition of any one of embodiments 1-23, wherein the TGM1 polypeptide is a human TGM1 polypeptide.

Embodiment 25: The pharmaceutical composition of any one of embodiments 1-24, wherein the one or more polynucleotides encoding the TGM1 polypeptide have at least 80%, at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 1 or SEQ ID NO: 2.

Embodiment 26: The pharmaceutical composition of any one of embodiments 1-25, wherein the TGM1 polypeptide has at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5.

Embodiment 27: The pharmaceutical composition of any one of embodiments 1-26, wherein the pharmaceutically acceptable carrier is adapted for cutaneous (systemic or topical), transdermal, subcutaneous, and/or intradermal administration.

Embodiment 28: The pharmaceutical composition of any one of embodiments 1-27, wherein the pharmaceutically acceptable carrier is adapted for topical administration.

Embodiment 29: The pharmaceutical composition of any one of embodiments 1-28, wherein the pharmaceutically acceptable carrier comprises a hydroxypropyl methylcellulose gel.

Embodiment 30: The pharmaceutical composition of any one of embodiments 1-29, wherein the pharmaceutically acceptable carrier comprises a phosphate buffer.

Embodiment 31: The pharmaceutical composition of any one of embodiments 1-30, wherein the pharmaceutically acceptable carrier comprises glycerol.

Embodiment 32: A kit comprising: (a) the pharmaceutical composition of any one of embodiments 1-31; and (b) instructions for administering the pharmaceutical composition.

Embodiment 33: A method of enhancing, increasing, augmenting, and/or supplementing the levels of a TGM1 polypeptide in one or more cells of a subject, the method comprising administering to the subject an effective amount of the pharmaceutical composition of any one of embodiments 1-31.

Embodiment 34: A method of enhancing production of cornified cell envelopes and/or stabilizing the stratum corneum layer of the skin of a subject, the method comprising administering to the subject an effective amount of the pharmaceutical composition of any one of embodiments 1-31.

Embodiment 35: A method of treating a barrier function defect in a subject in need thereof, the method comprising administering to the subject an effective amount of the pharmaceutical composition of any one of embodiments 1-31.

Embodiments 36: A method of providing prophylactic, palliative, or therapeutic relief to one or more signs or symptoms of autosomal recessive congenital ichthyosis (ARCI) in a subject in need thereof, the method comprising administering to the subject an effective amount of the pharmaceutical composition of any one of embodiments 1-31.

Embodiment 37: The method of any one of embodiments 33-36, wherein the subject is a human.

Embodiment 38: The method of any one of embodiments 33-37, wherein the subject suffers from lamellar ichthyosis (LI) and/or non-bullous congenital ichthyosiform erythroderma (NCIE).

Embodiment 39: The method of any one of embodiments 33-38, wherein the subject suffers from lamellar ichthyosis (LI).

Embodiment 40: The method of any one of embodiments 33-39, wherein the pharmaceutical composition is administered cutaneously (systemically or topically), transdermally, subcutaneously, or intradermally to the subject.

Embodiment 41: The method of any one of embodiments 33-40, wherein the pharmaceutical composition is administered topically to the subject.

Embodiment 42: The method of any one of embodiments 33-41, wherein the pharmaceutical composition is administered one, two, three, four, five or more times per day.

Embodiment 43: The method of any one of embodiments 33-42, wherein the pharmaceutical composition is administered to one or more affected and/or unaffected areas of the subject.

Embodiment 44: The method of any one of embodiments 33-43, wherein the skin of the subject is abraded prior to administration.

Embodiment 45: The method of any one of embodiments 36-44, wherein the one or more signs or symptoms of ARCI are selected from an abnormal stratum corneum, incomplete thickening of the cornified cell envelope, defects in the intercellular lipid layers in the stratum corneum, generalized scaling with variable redness of the skin, formation of large plate-like scales, accelerated epidermal turnover, palmoplantar hyperkeratosis, defective barrier function, recurrent skin infections, exposure keratitis, hypohidrosis, heat intolerance, corneal perforation, rickets, nail abnormalities, dehydration, respiratory problems, ectropion, eclabium, hypoplasia of joint and nasal cartilage, hypotrichosis, scarring alopecia, renal insufficiency, and sepsis.

Embodiment 46: A recombinant nucleic acid comprising one or more polynucleotides encoding a Transglutaminase 1 (TGM1) polypeptide, wherein the recombinant nucleic acid is a recombinant herpes simplex virus genome.

Embodiment 47: The recombinant nucleic acid of embodiment 46, wherein the recombinant herpes simplex virus genome comprises two or more polynucleotides encoding a TGM1 polypeptide.

Embodiment 48: The recombinant nucleic acid of embodiment 46 or embodiment 47, wherein the recombinant herpes simplex virus genome is a recombinant HSV-1 genome, a recombinant HSV-2 genome, or any derivatives thereof Embodiment 49: The recombinant nucleic acid of any one of embodiments 46-48, wherein the recombinant herpes simplex virus genome comprises an inactivating mutation in a herpes simplex virus gene.

Embodiment 50: The recombinant nucleic acid of embodiment 49, wherein the herpes simplex virus gene is selected from the group consisting of ICP0, ICP4, ICP22, ICP27, ICP47, tk, UL41, and UL55.

Embodiment 51: The recombinant nucleic acid of embodiment 50, wherein the recombinant herpes simplex virus genome comprises an inactivation mutation in one or both copies of the ICP4 gene.

Embodiment 52: The recombinant nucleic acid of embodiment 50 or embodiment 51, wherein the recombinant herpes simplex virus genome comprises an inactivating mutation in the ICP22 gene.

Embodiment 53: The recombinant nucleic acid of any one of embodiments 50-52, wherein the recombinant herpes simplex virus genome comprises an inactivating mutation in the ICP22 gene.

Embodiment 54: The recombinant nucleic acid of any one of embodiments 50-53, wherein the recombinant herpes simplex virus genome comprises an inactivating mutation in the UL41 gene.

Embodiment 55: The recombinant nucleic acid of any one of embodiments 50-54, wherein the recombinant herpes simplex virus genome comprises an inactivating mutation in the ICP0 gene.

Embodiment 56: The recombinant nucleic acid of any one of embodiments 50-55, wherein the recombinant herpes simplex virus genome comprises an inactivating mutation in the ICP27 gene.

Embodiment 57: The recombinant nucleic acid of any one of embodiments 49-56, wherein the inactivating mutation is a deletion of the coding sequence of the gene(s).

Embodiment 58: The recombinant nucleic acid of any one of embodiments 46-57, wherein the recombinant herpes simplex virus genome comprises the one or more polynucleotides within one or more viral gene loci.

Embodiment 59: The recombinant nucleic acid of any one of embodiments 46-58, wherein the recombinant herpes simplex virus genome comprises the one or more polynucleotides within one or both of the ICP4 viral gene loci.

Embodiment 60: The recombinant nucleic acid of any one of embodiments 46-59, wherein the recombinant herpes simplex virus genome comprises the one or more polynucleotides within the ICP22 viral gene locus.

Embodiment 61: The recombinant nucleic acid of any of any one of embodiments 46-60, wherein the recombinant herpes simplex virus genome comprises the one or more polynucleotides within the UL41 viral gene locus.

Embodiment 62: The recombinant nucleic acid of any one of embodiments 46-61, wherein the TGM1 polypeptide is a human TGM1 polypeptide.

Embodiment 63: The recombinant nucleic acid of any one of embodiments 46-62, wherein the one or more polynucleotides encoding the TGM1 polypeptide have at least 80%, at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 1 or SEQ ID NO: 2.

Embodiment 64: The recombinant nucleic acid of any one of embodiments 46-63, wherein the TGM1 polypeptide has at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5.

Embodiment 65: A host cell comprising the recombinant nucleic acid of any one of embodiments 46-64.

Embodiment 66: The host cell of embodiment 65, wherein the host cell is a eukaryotic cell.

Embodiment 67: The host cell of embodiment 65 or embodiment 66, wherein the host cell is a mammalian cell.

Embodiment 68: The host cell of any one of embodiments 65-67, wherein the host cell is a human cell or a non-human primate cell.

Embodiment 69: The host cell of any one of embodiments 65-68, wherein the host cell is a Vero cell.

Embodiment 70: The host cell of any one of embodiments 65-69, wherein the host cell is a complementing host cell.

Embodiment 71: A method of collecting a herpes simplex virus, the method comprising: (a) contacting a complementing host cell with the recombinant nucleic acid of any one of embodiments 46-64; and (b) collecting the herpes simplex virus generated by the complementing host cell.

Embodiment 72: A method of collecting a herpes simplex virus, the method comprising: (a) culturing the host cell of any one of embodiments 65-70; and (b) collecting the herpes simplex virus generated by the host cell.

Embodiment 73: A recombinant herpes virus genome comprising one or more polynucleotides encoding a transglutaminase polypeptide.

Embodiment 74: The recombinant herpes virus genome of embodiment 73, wherein the recombinant herpes virus genome comprises the one or more polynucleotides encoding the TGM polypeptide within one or more viral gene loci.

Embodiment 75: The recombinant herpes virus genome of embodiment 73 or 74, wherein the recombinant herpes virus genome is replication competent.

Embodiment 76: The recombinant herpes virus genome of embodiment 73 or 74, wherein the recombinant herpes virus genome is replication defective.

Embodiment 77: The recombinant herpes virus genome of any one of embodiments 73-76, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

Embodiment 78: The recombinant herpes virus genome of any one of embodiments 73-77, wherein the recombinant herpes virus genome is a recombinant herpes simplex virus genome.

Embodiment 79: The recombinant herpes virus genome of embodiment 78, wherein the recombinant herpes simplex virus genome is a recombinant type 1 herpes simplex virus (HSV-1) genome, a recombinant type 2 herpes simplex virus (HSV-2) genome, or any derivatives thereof.

Embodiment 80: The recombinant herpes virus genome of embodiment 78 or 79, wherein the recombinant herpes simplex virus genome is a recombinant type 1 herpes simplex virus (HSV-1) genome.

Embodiment 81: The recombinant herpes virus genome of any one of embodiments 77-80, wherein the recombinant herpes simplex virus genome comprises an inactivating mutation.

Embodiment 82: The recombinant herpes virus genome of embodiment 81, wherein the inactivating mutation is in a herpes simplex virus gene.

Embodiment 83: The recombinant herpes virus genome of embodiment 82, wherein the inactivating mutation is a deletion of the coding sequence of the herpes simplex virus gene.

Embodiment 84, The recombinant herpes virus genome of embodiment 82 or 83, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 85: The recombinant herpes virus genome of embodiment 84, wherein the recombinant herpes simplex virus genome comprises an inactivating mutation in one or both copies of the ICP4 gene.

Embodiment 86: The recombinant herpes virus genome of embodiment 84 or 85, wherein the recombinant herpes simplex virus genome comprises an inactivating mutation in the ICP22 gene.

Embodiment 87: The recombinant herpes virus genome of any one of embodiments 84-86, wherein the recombinant herpes simplex virus genome comprises an inactivating mutation in the UL41 gene.

Embodiment 88: The recombinant herpes virus genome of any one of embodiments 84-87, wherein the recombinant herpes simplex virus genome comprises an inactivating mutation in one or both copies of the ICP0 gene.

Embodiment 89: The recombinant herpes virus genome of any one of embodiments 84-88, wherein the recombinant herpes simplex virus genome comprises an inactivating mutation in the ICP27 gene.

Embodiment 90: The recombinant herpes virus genome of any one of embodiments 78-89, wherein the recombinant herpes simplex virus genome comprises the one or more polynucleotides encoding the TGM polypeptide within one or both of the ICP4 viral gene loci.

Embodiment 91: The recombinant herpes virus genome of any one of embodiments 78-90, wherein the recombinant herpes simplex virus genome comprises the one or more polynucleotides encoding the TGM polypeptide within the ICP22 viral gene locus.

Embodiment 92: The recombinant herpes virus genome of any one of embodiments 78-91, wherein the recombinant herpes simplex virus genome comprises the one or more polynucleotides encoding the TGM polypeptide within the UL41 viral gene locus.

Embodiment 93: The recombinant herpes virus genome of any one of embodiments 73-92, wherein the TGM polypeptide is selected from the group consisting of a TGM1 polypeptide, a TGM2 polypeptide, a TGM3 polypeptide, a TGM4 polypeptide, a TGMS polypeptide, a TGM6 polypeptide, and a TGM7 polypeptide.

Embodiment 94: The recombinant herpes virus genome of any one of embodiments 72-93, wherein the TGM polypeptide is a human TGM polypeptide.

Embodiment 95: The recombinant herpes virus genome of any one of embodiments 73-94, wherein the TGM polypeptide is a human TGM1 polypeptide.

Embodiment 96: The recombinant herpes virus genome of any one of embodiments 73-95, wherein the TGM polypeptide has at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5.

Embodiment 97: The recombinant herpes virus genome of any one of embodiments 73-96, wherein the recombinant herpes virus genome has reduced cytotoxicity when introduced into a target cell as compared to a corresponding wild-type herpes virus genome.

Embodiment 98: The recombinant herpes virus genome of embodiment 97, wherein the target cell is a cell of the epidermis and/or dermis.

Embodiment 99: The recombinant herpes virus genome of embodiment 97 or 98, wherein the target cell is a human cell.

Embodiment 100: A herpes virus comprising the recombinant herpes virus genome of any one of embodiments 73-99.

Embodiment 101: The herpes virus of embodiment 100, wherein the herpes virus is replication competent.

Embodiment 102: The herpes virus of embodiment 100, wherein the herpes virus is replication defective.

Embodiment 103: The herpes virus of any one of embodiments 100-102, wherein the herpes virus has reduced cytotoxicity as compared to a corresponding wild-type herpes virus.

Embodiment 104: The herpes virus of any one of embodiments 100-103, wherein the herpes virus is selected from the group consisting of a herpes simplex virus, a varicella zoster virus, a human cytomegalovirus, a herpesvirus 6A, a herpesvirus 6B, a herpesvirus 7, and a Kaposi's sarcoma-associated herpesvirus.

Embodiment 105: The herpes virus of any one of embodiments 100-104, wherein the herpes virus is a herpes simplex virus.

Embodiment 106: The herpes virus of any one of embodiments 100-105, wherein the herpes simplex virus is a type 1 herpes simplex virus (HSV-1), a type 2 herpes simplex virus (HSV-2), or any derivatives thereof.

Embodiment 107: A pharmaceutical composition comprising the recombinant herpes virus genome of any one of embodiments 73-99 or the herpes virus of any one of embodiments 100-106 and a pharmaceutically acceptable excipient.

Embodiment 108: The pharmaceutical composition of embodiment 107, wherein the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 109: The pharmaceutical composition of embodiment 107 or 108, wherein the pharmaceutical composition is suitable for topical, transdermal, subcutaneous, intradermal, or transmucosal administration.

Embodiment 110: The pharmaceutical composition of any one of embodiments 107-109, wherein the pharmaceutical composition is suitable for topical administration.

Embodiment 111: The herpes virus of any one of embodiments 100-106 or the pharmaceutical composition of any one of embodiments 107-110 for use as a medicament.

Embodiment 112: The herpes virus of any one of embodiments 100-106 or the pharmaceutical composition of any one of embodiments 107-110 for use in a therapy.

Embodiment 113: Use of the herpes virus of any one of embodiments 100-106 or the pharmaceutical composition of any one of embodiments 107-110 in the manufacture of a medicament for treating autosomal recessive congenital ichthyosis (ARCI).

Embodiment 114: A method of enhancing, increasing, augmenting, and/or supplementing the levels of a TGM polypeptide in one or more cells of a subject, the method comprising administering to the subject an effective amount of the herpes virus of any one of embodiments 100-106 or the pharmaceutical composition of any one of embodiments 107-110.

Embodiment 115: A method of enhancing production of cornified cell envelopes and/or stabilizing the stratum corneum layer of the skin of a subject, the method comprising administering to the subject an effective amount of the herpes virus of any one of embodiments 100-106 or the pharmaceutical composition of any one of embodiments 107-110.

Embodiment 116: A method of treating a barrier function defect in a subject in need thereof, the method comprising administering to the subject an effective amount of the herpes virus of any one of embodiments 100-106 or the pharmaceutical composition of any one of embodiments 107-110.

Embodiment 117: A method of providing prophylactic, palliative, or therapeutic relief to one or more signs or symptoms of autosomal recessive congenital ichthyosis (ARCI) in a subject in need thereof, the method comprising administering to the subject an effective amount of the herpes virus of any one of embodiments 100-106 or the pharmaceutical composition of any one of embodiments 107-110.

Embodiment 118: The method of embodiment 117, wherein the one or more signs or symptoms of ARCI are selected from an abnormal stratum corneum, incomplete thickening of the cornified cell envelope, defects in the intercellular lipid layers in the stratum corneum, generalized scaling with variable redness of the skin, formation of large plate-like scales, accelerated epidermal turnover, palmoplantar hyperkeratosis, defective barrier function, recurrent skin infections, exposure keratitis, hypohidrosis, heat intolerance, corneal perforation, rickets, nail abnormalities, dehydration, respiratory problems, ectropion, eclabium, hypoplasia of joint and nasal cartilage, hypotrichosis, scarring alopecia, renal insufficiency, and sepsis.

Embodiment 119: The method of any one of embodiments 114-118, wherein the subject is a human.

Embodiment 120: The method of any one of embodiments 114-119, wherein the subject suffers from lamellar ichthyosis (LI) and/or non-bullous congenital ichthyosiform erythroderma (NCIE).

Embodiment 121: The method of any one of embodiments 114-120, wherein the subject suffers from lamellar ichthyosis.

Embodiment 122: The method of any one of embodiments 114-121, wherein the subject's genome comprises a loss-of-function mutation in a TGM gene.

Embodiment 123: The method of any one of embodiments 114-122, wherein the herpes virus or pharmaceutical composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, peri-articularly, locally, or via inhalation to the subject.

Embodiment 124: The method of any one of embodiments 114-123, wherein the herpes virus or pharmaceutical composition is administered topically, transdermally, subcutaneously, or intradermally to the subject.

Embodiment 125: The method of any one of embodiments 114-124, wherein the herpes virus or pharmaceutical composition is administered topically to the subject.

Embodiment 126: The method of any one of embodiments 114-125, wherein the skin of the subject is abraded prior to administration.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art, and are to be included within the spirit and purview of this application and scope of the appended claims.

Example 1: Generation of Modified Herpes Simplex Virus Vectors Encoding Human TGM1

The following example describes the construction of recombinant herpes simplex type-1 viruses modified to express wild-type or codon-optimized human TGM1.

Wild-type herpes simplex virus genomes (FIG. 1A) were first modified by deleting the coding sequence of both copies of the viral ICP4 gene alone (4-only), or by deleting the coding sequence of both copies of the viral ICP4 gene as well as the single copy ICP22 gene (4/22). The 4-only and 4/22 viral genomes were also engineered to contain an mCherry expression cassette in each of the ICP4 loci. These viral genomes were then further modified to encode wild-type or codon-optimized human TGM1. Briefly, plasmids containing wild-type or codon-optimized human TGM1 (under control of the hCMV promoter) and flanked by the upstream (US) and downstream (DS) regions of ICP4 were transfected into Vero cells modified to express the herpes virus ICP4 gene. These transfected cells were then infected with the modified mCherry-expressing viruses described above. The US and DS ICP4 regions flanking TGM1 allowed for a double crossover and replacement of each of the mCherry loci. Visual screening for the absence of mCherry fluorescence was then used to identify cells containing recombined virus. Four variants of these attenuated recombinant viral constructs were created with this method: 1) a recombinant ΔICP4-modified HSV-1 genome comprising expression cassettes containing wild-type human TGM1 cDNA (SEQ ID NO: 1) under the control of a heterologous promoter integrated at each ICP4 locus (FIG. 1B); 2) a recombinant ΔICP4/ΔICP22-modified HSV-1 genome comprising expression cassettes containing wild-type human TGM1 cDNA (SEQ ID NO: 1) under the control of a heterologous promoter integrated at each ICP4 locus (FIG. 1C); 3) a recombinant ΔICP4-modified HSV-1 genome comprising expression cassettes containing codon-optimized human TGM1 cDNA (SEQ ID NO: 2) under the control of a heterologous promoter integrated at each ICP4 locus (FIG. 1D); and 4) a recombinant ΔICP4/ΔICP22- modified HSV-1 genome comprising expression cassettes containing codon-optimized human TGM1 cDNA (SEQ ID NO: 2) under the control of a heterologous promoter integrated at each ICP4 locus (FIG. 1E). Multiple isolates of each of the modified viruses were collected for further validation.

To test whether the isolates were capable of expressing human TGM1, ICP4-complementing Vero cells were plated in 6-well plates and were mock infected, infected with a corresponding modified HSV encoding mCherry, or infected with untitered viral isolates of the ΔICP4 or ΔICP4/ΔICP22 viruses encoding wild-type or codon-optimized human TGM1 for 48 or 72 hours (until the completion of infection). After infection, the cells were collected by gentle scraping, centrifuged to collect cell pellets, culture medium was aspirated, and the cell pellets were washed once with PBS. Following washing, each cell pellet was resuspended in 200 μL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. A lane of the polyacrylamide gel was loaded with recombinant human TGM1 (R&D Systems, cat. no. 7765-TG-050) as a positive control. After electrophoresis, the protein was transferred to a PVDF membrane, and the membrane was blocked for 30 minutes in 5% milk/TBS. Primary rabbit anti-TGM1 polyclonal antisera (Abcam, cat. no. ab103814) was then added to the PVDF membrane at 1:1000 dilution in 5% milk/TBS and incubated overnight at RT° C. (~16 hours). The blots were then washed 3× for 5 minutes each with TBS, and then stained with an AP-conjugated goat anti-rabbit IgG antibody (Sigma, cat. no. A3687) in 5% milk/TB S for 1 hour at RT° C. The membranes were then washed 3× for 5 minutes each with TBS, BCIP/NBT was added, and the blots were developed for ~10 minutes at RT° C.

3/4 isolates of the ΔICP4/ΔICP22-modified HSV-1 comprising expression cassettes containing wild-type human TGM1 cDNA were capable of expressing human TGM1 protein at detectable levels (FIG. 2A); 5/5 isolates of the AICP4/AICP22-modified HSV-1 comprising expression cassettes containing codon-optimized human TGM1 cDNA were capable of expressing human TGM1 protein at detectable levels (FIG. 2B); and 4/4 isolates of the ΔICP4-modified HSV-1 comprising expression cassettes containing wild-type human TGM1 cDNA (FIG. 2C) or codon-optimized human TGM1 cDNA (FIG. 2D) were capable of expressing human TGM1 protein at detectable levels. Taken together, the data indicated that both wild-type and codon-optimized human TGM1 could be successfully expressed from various configurations of modified HSV1 at a success rate of 75%-100%. One isolate of each strain was then selected for in vitro and in vivo analysis described in the following examples.

Example 2: In Vitro Analysis of HSV Candidates Encoding Human TGM1

The following example describes in vitro experiments showing that the recombinant viruses constructed in Example 1 were capable of expressing human TGM1 protein in a normal keratinocyte cell line, as well as in immortalized cells generated from primary human keratinocytes isolated from a patient suffering from lamellar ichthyosis (LI).

To test the ability of the recombinant viruses to express their encoded human TGM1 cassettes in non-complementing human cells, HaCaT immortalized keratinocytes were plated in 6-well plates and were mock infected, infected with a modified HSV encoding a reporter gene, or infected with purified, titered test virus for 48 hours at an MOI of 1. Following the 48-hour incubation, the cells were collected by gentle scraping, centrifuged to collect cell pellets, culture medium was aspirated, and the cell pellets were washed once with PBS. Following washing, each cell pellet was resuspended in 2004, RIPA buffer containing protease inhibitors, and the resuspensions were incubated at 4° C. for 20 minutes with gentile agitation every 5 minutes. The protein concentration of each lysate was then determined by micro-BCA assay. After determining total protein concentration, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading 22.5 µg protein/sample on a 4-20% Tris-Glycine polyacrylamide gel. A lane of the polyacrylamide gel was loaded with recombinant human TGM1 (R&D Systems, cat. no. 7765-TG-050) as a positive control. After electrophoresis, the protein was transferred to a PVDF membrane, and the membrane was blocked for 30 minutes in 5% milk/TBS. Primary rabbit anti-TGM1 polyclonal antisera (Abcam, cat. no. ab103814) was then added to the PVDF membrane at 1:1000 dilution in 5% milk/TBS and incubated overnight at RT° C. (~16 hours). The blots were then washed 3× for 5 minutes each with TBS, and then stained with an AP-conjugated goat anti-rabbit IgG antibody (Sigma, cat. no. A3687) in 5% milk/TBS for 1 hour at RT° C. The membranes were then washed 3× for 5 minutes each with TBS, BCIP/NBT was added, and the blots were developed for ~10 minutes at RT° C.

Figure 3:
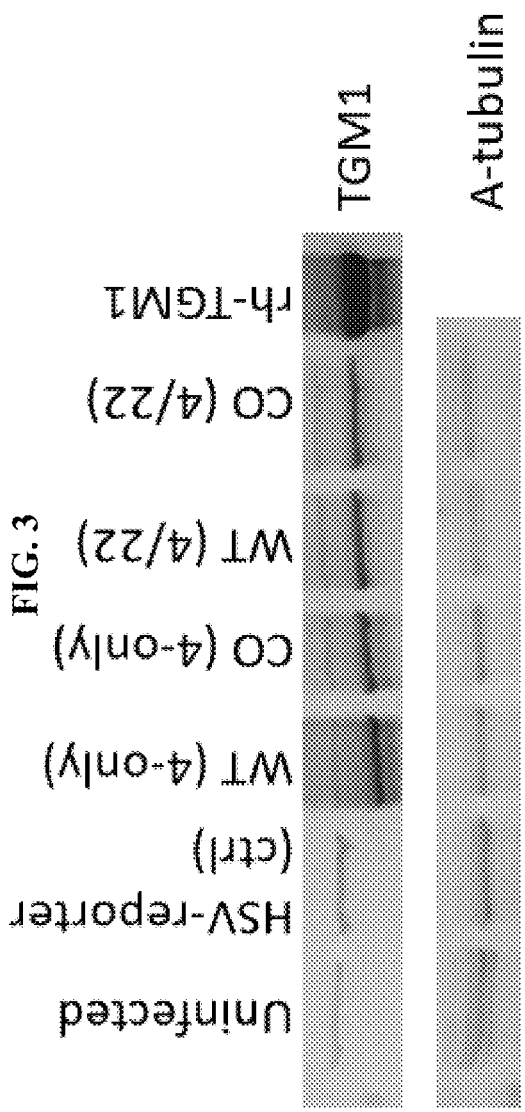
FIG. 3 shows western blot analysis of wild-type (WT) or codon-optimized (CO) human TGM1 expression in human HaCaT immortalized keratinocytes 48 hours after infection with the indicated modified HSV-1 strains at a multiplicity of infection (MOI) of 1. Uninfected cells and cells infected with an HSV-reporter strain were used as negative controls; recombinant human (rh) TGM1 was used as a positive control; human α-tubulin was used as a loading control.

In agreement with the data provided from Vero cells, all four versions of the recombinant virus showed suitable expression of human TGM1 in HaCaT cells (FIG. 3).

Figure 4:
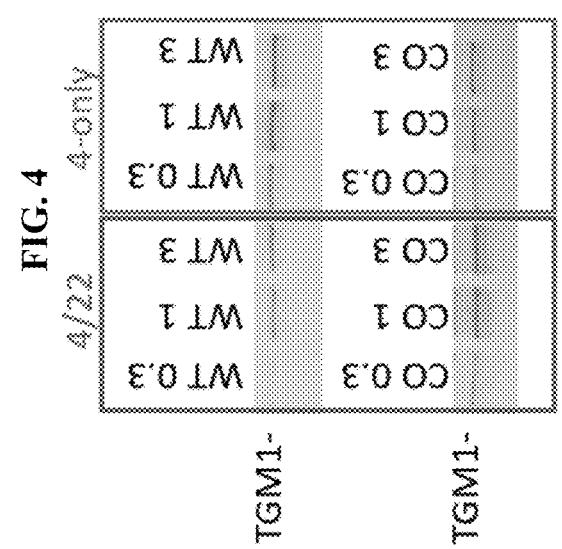
FIG. 4 shows western blot analysis of wild-type (WT) or codon-optimized (CO) human TGM1 expression in human HaCaT immortalized keratinocytes 48 hours after infection with the indicated HSV-1 strains at an MOI of 0.3, 1, or 3.

The ability of the recombinant viruses to express TGM1 when used at varying MOIs was next tested. HaCaT cells were plated in 6-well plates and infected with the purified, titered virus for 48 hours at an MOI of 0.3, 1.0, or 3.0. Protein samples were processed, and western blots were conducted, as described above. A good dose response was observed using all 4 versions of the recombinant virus (FIG. 4).

Figure 5B:
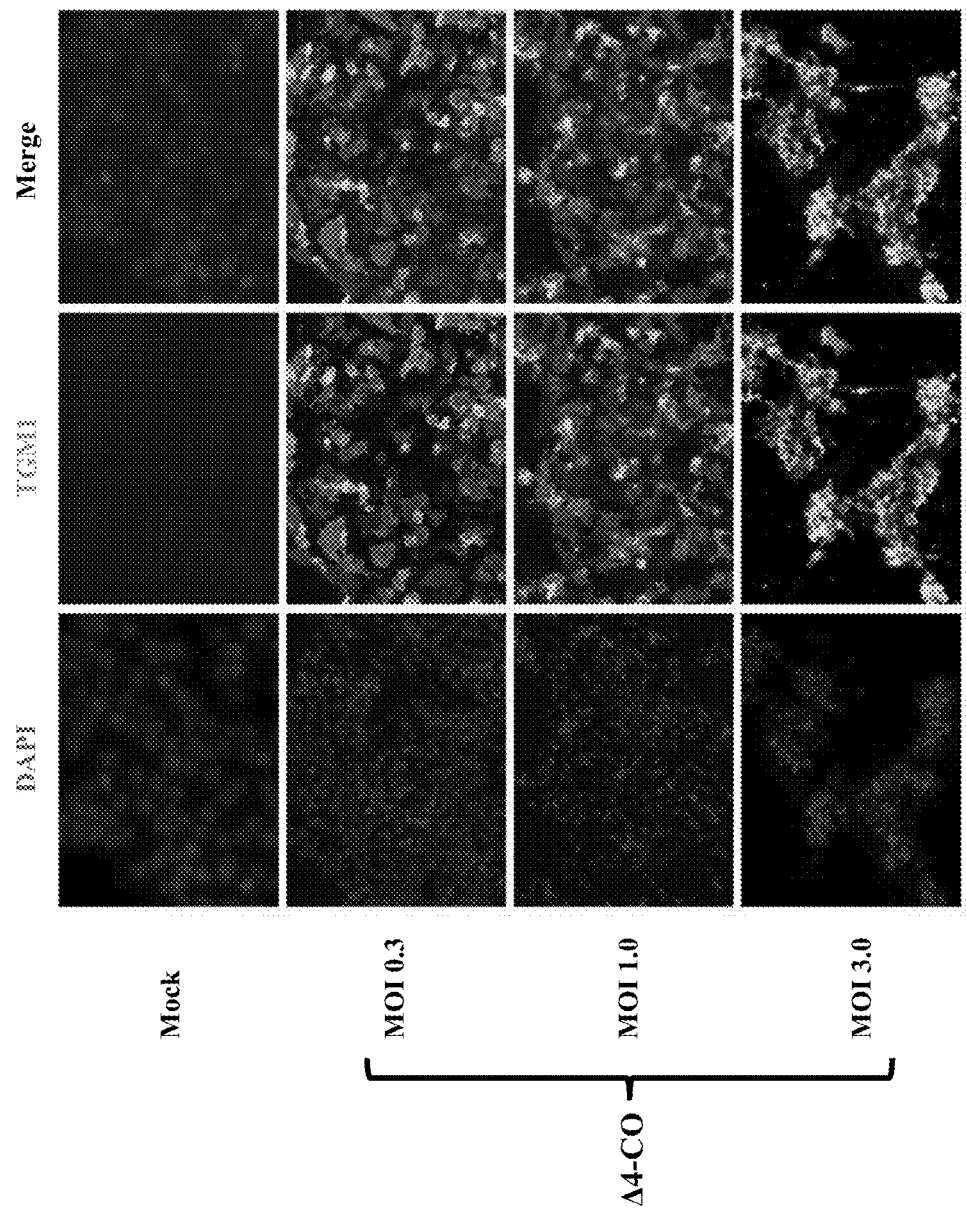

Immunofluorescence experiments were also conducted to visualize TGM1 expression in HaCaT cells after infection with the recombinant HSVs at various MOIs. HaCaT immortalized keratinocytes were plated in 8-chamber slides and were mock infected or infected with the recombinant HSVs at an MOI of 0.3, 1.0, or 3.0 as described above. After infection, the slides were fixed with methanol at −20° C. for 20 minutes, were blocked with Power Block (BioGenex, cat. no. HK083-50K) at RT° C. for 30 minutes, and were incubated with primary antibody (rabbit anti-TGM1 polyclonal antisera (Abcam, cat. no. ab103814)) diluted 1:200 in Antibody Diluent (ThermoFisher, cat. no. 003118) at 4° C. overnight. Following 3 washes in PBS, the samples were then stained with a 1:200 dilution of goat anti-rabbit IgG Alexa Fluor® 488 secondary antibody (ThermoFisher, cat. no. 11034) at RT° C. for 1 hour. After 3 additional washes in PBS, samples were incubated with VECTASHIELD HardSet Antifade Mounting Medium with DAPI (Vector Laboratories, cat. no. H-1500), and TGM1 expression was assessed on a Revolve R4 fluorescent microscope (Echo). All images were captured after setting the basic signal strength as the signal from cells infected at an MOI of 1.0 with the ΔICP4/ΔICP22 codon-optimized variant. Human TGM1 expression was observed in HaCaT cells, as measured by immunofluorescence, using wild-type TGM1-encoding (data not shown) and codon-optimized TGM1-encoding (FIGS. 5A-B) versions of the recombinant viruses at all MOIs, in agreement with the western blots shown in FIGS. 3-4.

Figure 6:
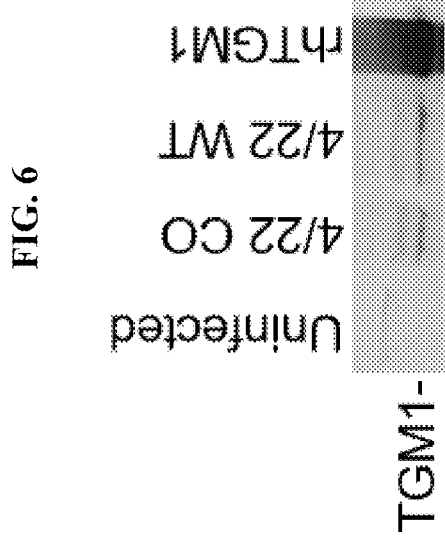
FIG. 6 shows western blot analysis of wild-type (WT) or codon-optimized (CO) human TGM1 expression in immortalized lamellar ichthyosis (LI) keratinocytes 48 hours after infection with attenuated ΔICP4/ΔICP22-modified HSV-1 encoding either wild-type (4/22 WT) or codon-optimized (4/22 CO) human TGM1 at an MOI of 1. Uninfected LI keratinocytes were used as a negative control; recombinant human (rh) TGM1 was used as a positive control.
Figures 7A, 7B:
FIGS. 7A-B show qRT-PCR analyses of wild-type (WT) or codon-optimized (CO) human TGM1 transcripts expressed in skin biopsies taken from BALB/c mice 48 hours after intradermal injection of either vehicle control (CTRL) or the indicated TGM1-encoding modified HSV-1 strains. 10 ng/μL of total RNA was used in each reaction.
Figure 8A:
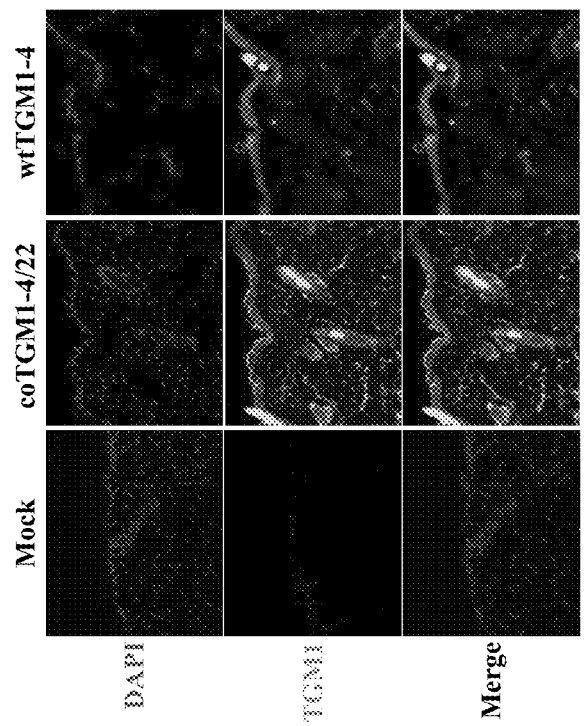
FIGS. 8A-B show representative immunofluorescence and hematoxylin and eosin (H&E) staining images of skin biopsies taken from BALB/c mice 48 hours after intradermal injection of either vehicle control (mock) or the indicated TGM1-encoding modified HSV-1 strains.
Figure 8B:
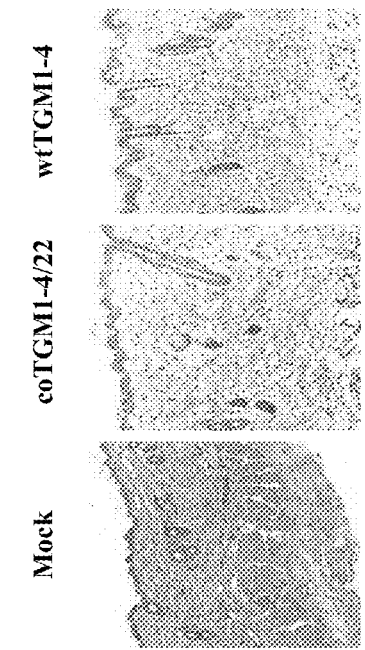

It is known that patients suffering from lamellar ichthyosis (LI) often harbor mutations in endogenous TGM1. Thus, it was important to determine whether the recombinant viruses were capable of rescuing TGM1 expression in cells isolated from a patient suffering from LI. To this end, immortalized cells derived from primary human keratinocytes isolated from an LI patient (harboring a TGM1 mutation) were obtained. These LI cells were plated in 6-well plates, and were mock infected, or infected with the ΔICP4/ΔICP22 HSV variant containing wild-type (WT) or codon-optimized (CO) human TGM1 expression cassettes. A well of LI cells were also infected in parallel with an mCherry-expressing virus as a second negative control, to ensure that any differences observed in the western blots were not due to non-specific protein induction after HSV infection (data not shown). The LI cells were infected with purified, titered virus at an MOI of 1 for 48 hours. Protein samples were processed, and western blots were conducted, as described above. Importantly, it was shown that western blot-detectable levels of TGM1 were expressed in LI cells infected with either the WT or CO variants of the ΔICP4/ΔICP22 virus (FIG. 6).

Taken together, the data presented in this example indicated that both wild-type and codon-optimized human TGM1 could be successfully expressed from the modified HSVs in both normal and LI human cells.

Example 3: In Vivo Analysis of HSV Candidates Encoding Human TGM1

The following example describes experiments showing that the recombinant viruses constructed in Example 1 and validated in vitro in human cells in Example 2 were capable of expressing human TGM1 in vivo.

An in vivo study was initiated to determine whether the recombinant viruses could express human TGM1 in infected mice. For this study, 4 BALB/c male mice were used. Animals were shaved prior to administration, and the mice were injected at four sites with 1004, prepared virus/injection site. 48 hours after injection, skin biopsies were collected using an 8 mm punch. The biopsies were bisected, with one half being snap-frozen in liquid nitrogen and stored at −80° C., while the other half was prepared for sectioning. Table 1 below provides a synopsis of the experimental design.

TABLE 1 study design and test article administration

| Group No. | Test Article | Route of Administration | Location, No. of Sites | Termination |
|---|---|---|---|---|
| 1 | HSV-wtTGM1_ΔICP4/ΔICP22 | ID | Flank, 4 | 48 hours |
| 2 | HSV-coTGM1_ΔICP4/ΔICP22 | ID | Flank, 4 | 48 hours |
| 3 | HSV-wtTGM1_ΔICP4 | ID | Flank, 4 | 48 hours |
| 4 | HSV-coTGM1_ΔICP4 | ID | Flank, 4 | 48 hours |

ID = intradermal qRT-PCR analysis of the skin biopsies was performed for 2 mice each receiving the modified HSV containing the wild-type human TGM1 expression cassettes (FIG. 7A) or codon-optimized human TGM1 expression cassettes (FIG. 7B). Briefly, skin biopsies were lysed in Buffer RLT (AllPrep DNA/RNA Mini Kit, Qiagen, cat. no. 80204) with DTT (G-Biosciences, cat. no. 3483-12-3) using sonication with a QSONICA sonicator (125W, 20 Hz) at an amplitude of 25%. Following sonication, high speed centrifugation was used to pellet any insoluble material. RNA was then isolated with the AllPrep DNA/RNA Mini Kit as described by the manufacturer. The qRT-PCR assay was performed using Quantabio 1-step RT-qPCR ToughMix (Quantabio, cat. no. 95134-500) using wild-type and codon-optimized TGM1 PCR primer assays. All four viruses were shown to successfully express TGM1 transcripts in vivo.

TGM1 expression in skin samples harvested from the injected animals was also assessed by immunofluorescence. OCT frozen tissue was sectioned at 5 μm and left to air dry for up to 1 hour. The slides were dipped in 100% methanol (MeOH) for 10 minutes at −20° C. and left to air dry. The methanol-fixed sections were rehydrated through 3 washes in PBS (5 minutes each) at room temperature. The sections were incubated with 3% $H_2O_2$ followed by incubating with a blocking solution (Power Block) for 5 minutes at room temperature in a humid chamber. The excess blocking solution was removed and a drop of primary antibody (rabbit anti-human TGM1, Abcam cat. no. Ab103814) solution prepared in antibody diluent buffer (1:200 dilution) was applied to each section (30-50 μL/section). The sections were incubated with the primary antibody for 16 hours at 4° C., washed 3 times in PBS for 5 minutes each at room temperature, and secondary antibody (Alexa Fluor® 488-conjugated goat anti-rabbit, Invitrogen cat. no. A11034) was applied at a 1:400 dilution in PBS for 30 minutes at room temperature in a humid chamber. A PBS wash was repeated three times, and the stained sections were mounted with mounting media (Fluoromount G, Southern Biotech 0100-01) and covered with a coverslip. The sections were imaged after dehydration (approximately 24 hours) using an ECHO Fluorescence Microscope. Robust human TGM1 expression was observed in the skin of animals treated intradermally with attenuated viruses expressing either a wild-type or codon-optimized variant of the transgene (FIG. 8A). Histological examination of the skin was also conducted to determine whether infection with the engineered viruses caused any damage (FIG. 8B). No significant inflammation or gross changes in tissue architecture were observed after infection with either the ΔICP4 or ΔICP4/ΔICP22 viruses, suggesting that these engineered viruses induce little to no cytotoxicity or necrosis.

Taken together, the studies presented in this example demonstrated that both ΔICP4 and ΔICP4/ΔICP22 engineered viruses encoding either wild-type or codon-optimized variants of human TGM1 were capable of safely and effectively expressing high levels of a human transglutaminase in vivo, at both the RNA and protein levels. One of these viruses, termed TGvec01, was subsequently selected for additional in vitro and in vivo analyses.

Example 4: In Vitro Characterization of TGvec01 in Immortalized and Primary Patient Cells The following example describes in vitro experiments establishing relevant 2D cell culture model systems of both immortalized and primary normal and LI patient keratinocytes in order to characterize TGvec01 (from Example 3) before moving to 3D organotypic culture and in vivo studies.

Materials and Methods

Cells and Cell Culture

Normal and lamellar ichthyosis (LI) patient cells were previously isolated from skin biopsies as part of routine surgical or diagnostic procedures. Informed written consent was obtained from each patient, or in the case of children, from the parent or legal guardian. A population of these primary normal and LI keratinocytes were immortalized. The LI patient keratinocytes were homozygous for a c.877-2A>G splice-site mutation, the most commonly reported TGM1 mutation in humans (~34% of all TGM1 mutated alleles identified in ARCI patients and reported to date carry this mutation).

All cells were cultured at 37° C. in 5% $CO_2$. For immortalized LI and normal keratinocytes, as well as primary LI keratinocytes, the cells were cultured in EpiLife® cell culture medium (Gibco). For primary normal keratinocytes, the cells were culture in a 50/50 mix of Defined Keratinocyte serum free medium (Gibco) and Medium 154 (Gibco) supplemented with Human Keratinocyte Growth Supplement (Gibco) and antibiotic/antimycotic solution (Corning). Cells were grown in 6-well plates for qPCR/qRT-PCR analyses and western blotting. Cells were grown in 8 chamber slides for immunofluorescence.

Viral Infections

Viral aliquots were removed from the −80° C. freezer and were left to defrost under the tissue culture laminar flow hood. Multiplicity of infection was calculated from the virus titer and target cell number, the appropriate volume of virus stock was diluted in cell culture medium to a final volume of 100 μL, and the prepared virus was incubated with the target cells for 1 hour at 37° C. After the hour-long infection, 2 mL of the appropriate cell culture medium was added to well of the 6-well plate, or in the case of 8 chamber slides, 400 μL of medium was added.

qPCR/qRT-PCR Analysis

Immortalized keratinocytes were plated in 6-well plates at $7 \times 10^5$ (normal keratinocytes) or $3.6 \times 10^5$ (LI keratinocytes) cells/well to achieve 85-90% confluence the following day. 48 hours after mock infection or infection with TGvec01 (or an mCherry-expressing control HSV-1), cells were resuspended in 350₄, RLT buffer containing DTT and homogenized by passing through a QiaShredder column according to the manufacturer's protocol. DNA and RNA were isolated using an AllPrep DNA/RNA Mini kit (Qiagen) according to the manufacturer's protocol. For qPCR/qRT-PCR analysis, 50 ng of DNA or RNA were used per reaction in a total reaction volume of 25 μL. DNA quantification was determined by qPCR analysis using a Taqman® Fast Advanced Master Mix (Applied Biosystems); RNA quantification was determined by qRT-PCR analysis using Quantabio 1-Step RT-qPCR ToughMix. All samples were run in duplicate.

Western Blots

Immortalized and primary keratinocytes were plated in 6-well plates at $7 \times 10^5$ (normal keratinocytes) or $3.6 \times 10^5$ (LI keratinocytes) cells/well to achieve 85-90% confluence the following day. 48 hours after infection, cells were lysed with RIPA buffer and incubated with intermittent agitation every 5 minutes for 20 minutes. Next, benzonase (10U) was added to each lysate for 10 minutes at room temperature. Lysates were centrifuged for 5 minutes at 4° C., and total protein concentration in the cleared lysates was determined using a Pierce MicroBCA assay (ThermoFisher). Lysates were then mixed with 4×LDS sample buffer (Invitrogen) containing 5% 2-mercaptoethanol. Prior to loading, samples were first boiled for five minutes at 95° C., allowed to cool to room temperature, and then briefly centrifuged. 22.5 μg of lysate/well was run on a 4-20% Tris-Glycine gel and then transferred onto PVDF (Millipore). PVDF blots were blocked for 30 minutes in 5% milk/Tris-buffered saline. Primary antibodies (rabbit anti-human TGM1, Abcam cat. no. ab103814; rabbit anti-GAPDH, Abcam cat. no. ab9485) were incubated with the blocked blots overnight at room temperature. Blots were then incubated with secondary antibody (goat anti-rabbit IgG-AP conjugated, Sigma) for 1 hour at room temperature, the blots were washed three times with TBS for five minutes each, and the washed blots were then incubated with Novex AP Chromogenic substrate (Invitrogen) to allow for development of the bands.

Immunofluorescence

Immortalized and primary keratinocytes were plated in 8 chamber slides at $1.2 \times 10^5$ (normal keratinocytes) or $7 \times 10^4$ (LI keratinocytes) to achieve 85-90% confluence the following day. 48 hours after infection, the slides were removed from the incubator, aspirated, and cold methanol (−20° C.) was added to each chamber. Methanol treated slides were incubated at −20° C. for twenty minutes. The slides were then washed three times with room temperature PBS, and the chamber apparatus was removed from the slides. The slides were blocked with 5% BSA for 30 minutes at room temperature, at which time the slides were stained with primary antibody (rabbit anti-human TGM1, Abcam cat. no. ab103814) for two hours at room temperature. Slides were washed with PBS three times for 5 minutes each, counterstained with secondary antibody (Alexa Fluor® 488-conjugated goat anti-rabbit, Invitrogen cat. no. A11034) for one hour at room temperature, and again washed with PBS three times for 5 minutes each. Coverslips were mounted after VectaShield HardSet with DAPI, and the samples were visualized on an Echo Revolve microscope.

TGM1 In Situ Activity Assay

Immortalized LI keratinocytes were plated in 8 chamber slides at $7 \times 10^4$ cells/well to achieve 85-90% confluence the following day. 48 hours after infection, media was removed from each well of the slides and the slides were fixed at −20° C. in cold acetone for 10 minutes. The fixed slides were then washed 3× with PBS, and were blocked with 1% BSA in 100 mM Tris-HCl (pH 7.5) for 30 minutes. The slides were next rinsed with PBS, blocked with Avidin-Biotin-Block solution according to the manufacturer's protocol (Life Technologies), and again washed 3× with PBS. Next, TG2 inhibitor (Z-DON, 100 nM, Zedira) was incubated on the slides for 30 minutes at 37° C. in 100 mM Tris-HCl (pH 7.5) with 5 mM $CaCl_2$. Inhibitor was removed, and TG substrate (Keratinocyte transglutaminase (TG1)-substrate-peptide K5, 0.1 mM, Zedira) was incubated with the slides for 2 hours at 37° C. After the incubation, 25 mM EDTA was added to the slides for 5 minutes to inhibit the reaction. Slides were washed 3× with PBS, and streptavidin avidin-Alexa Fluor® 488 (1:50 dilution, Life Technologies) was added to the slides for 30 minutes at room temperature (RT). Slides were again washed 3× with PBS, and background autofluorescence was darkened by treatment with 0.1% Sudan Black for 15 minutes at room temperature. Slides were then mounted with HardSet Mounting Media with DAPI (VectaShield), and imaged on a Revolve Echo fluorescence microscope.

Results

A dose-ranging study was conducted to determine the efficacy of TGvec01-mediated delivery of its encoded human cargo in both immortalized normal and LI keratinocytes. The immortalized cells were infected for 48 hours at various multiplicities of infection (MOI) ranging from 0.3 to 3, and human TGM1 expression was quantitatively and qualitatively measured via multiple assays.

Figure 9A:
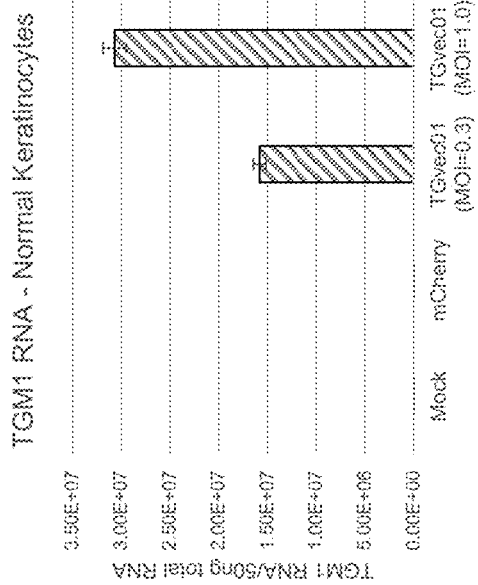
FIGS. 9A-H show human TGM1 nucleic acid and protein analyses of immortalized normal or LI keratinocytes infected with TGvec01.
Figure 9C:
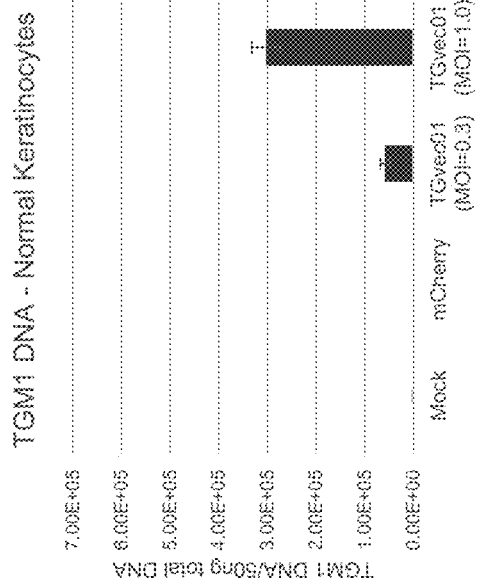
Figure 9B:
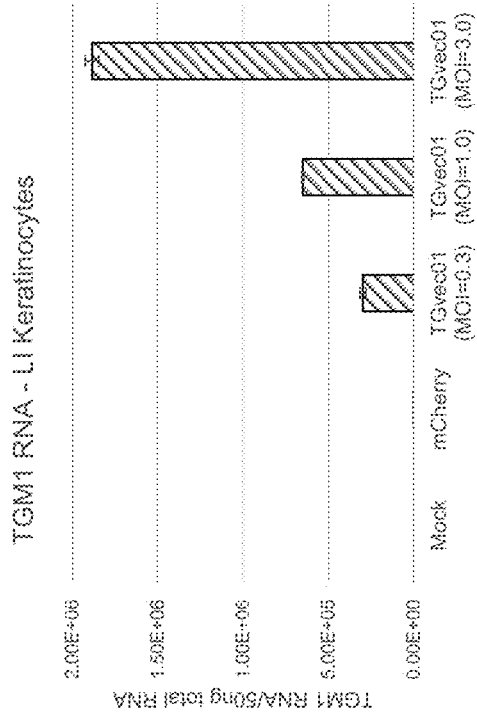
Figure 9D:
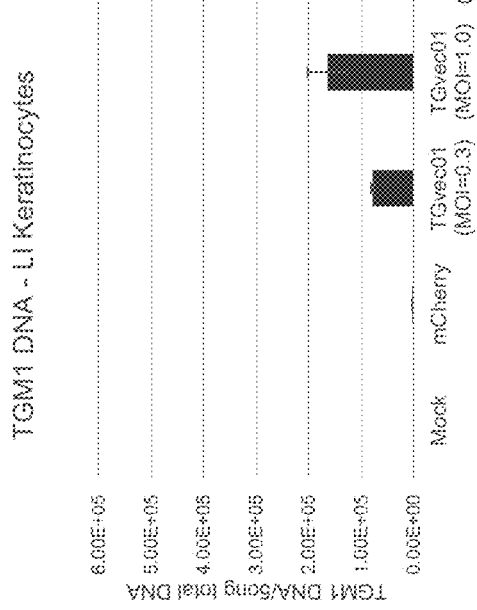

Dose-dependent increases in both effector DNA and transcript levels were observed by qPCR (FIG. 9A) and qRT-PCR (FIG. 9B), respectively, in immortalized normal human keratinocytes. Similar dose-dependent increases between MOIs 0.3 and 3 were observed in immortalized TGM1-deficient LI patient keratinocytes at both the DNA (FIG. 9C) and transcript (FIG. 9D) levels. Mock infected cells, and cells infected with a virus containing the same HSV-1 backbone as TGvec01 but instead encoding an mCherry effector, were used as negative controls.

Figure 9E:
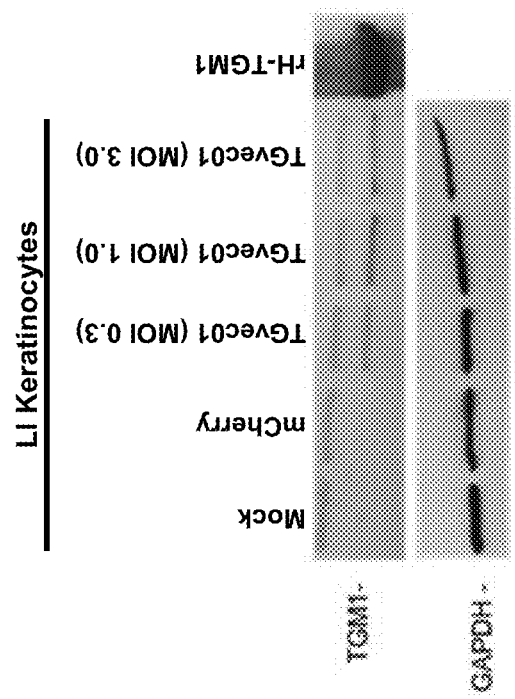
Figure 9F:
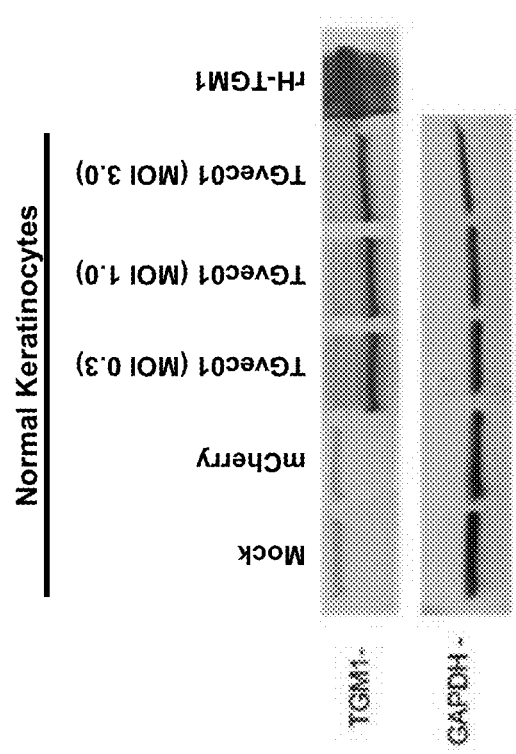

Paralleling these results, a dose-dependent increase in TGM1 protein expression after TGvec01 infection was observed by western blot analysis in immortalized normal (FIG. 9E) and LI (FIG. 9F) keratinocytes. While TGM1 protein expression increased in TGvec01-exposed cells between an MOI of 0.3 and 1, a further increase in TGM1 protein expression was not observed between an MOI of 1 and 3, suggesting that TGM1 may undergo regulation at the post-transcriptional/translational level in these cells. Importantly, no significant effect on cell morphology or viability was observed in immortalized normal or LI keratinocytes infected with TGvec01, even at high doses.

Figure 9H:
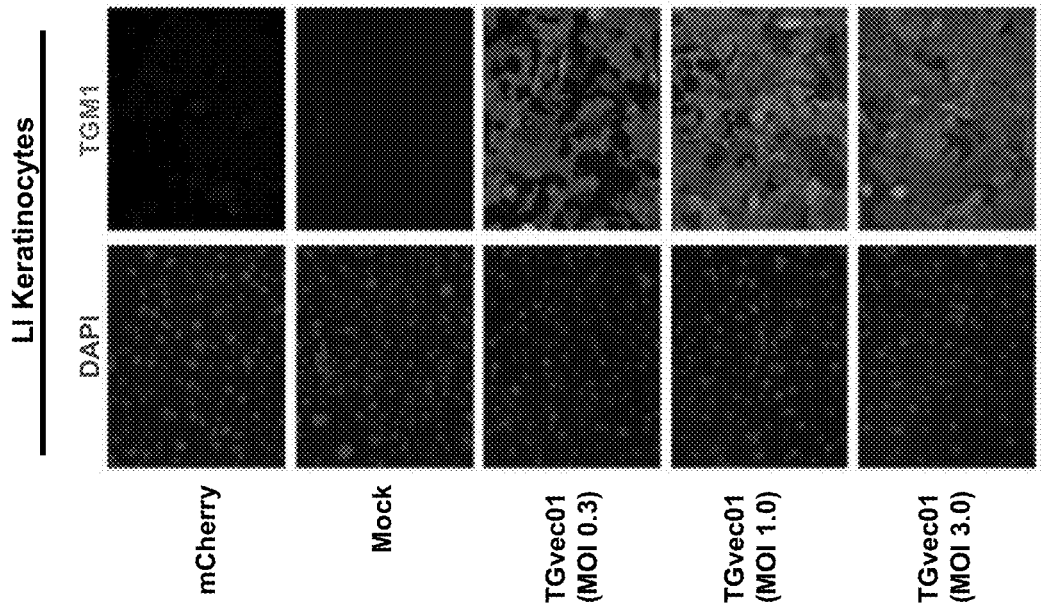
Figure 9G:
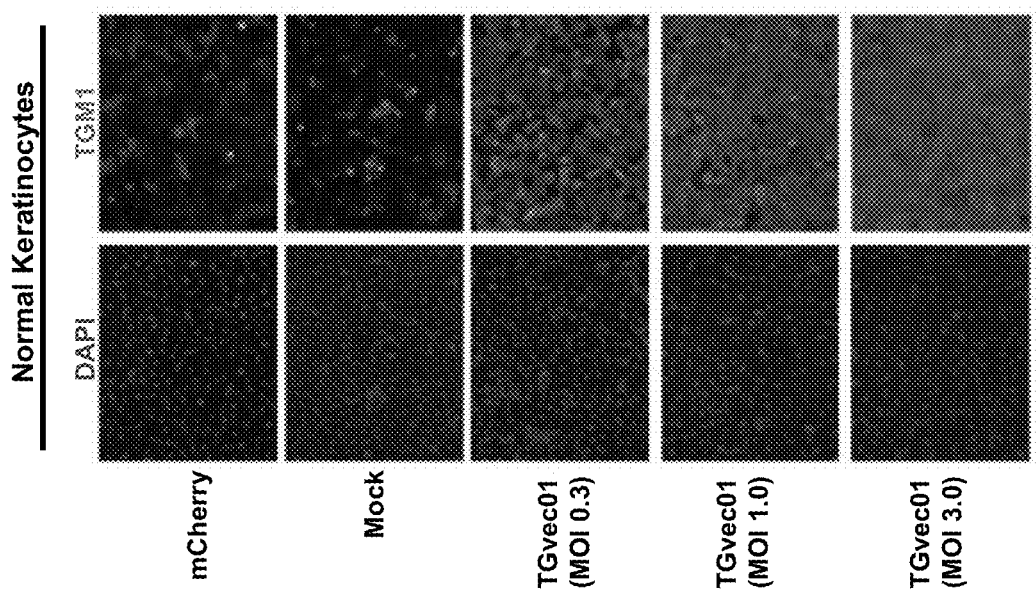

In agreement with the western blow data, a similar trend in dose-dependent increases in TGM1 protein after TGvec01 infection were observed in immortalized normal (FIG. 9G) and LI (FIG. 9H) keratinocytes, as assessed by immunofluorescence. While the immortalized normal keratinocytes expressed human TGM1 prior to infection (as expected), a significant increase in TGM1 expression was observed after infection with TGvec01, even at a low dose. Little-to-no detectable endogenous TGM1 was observed in the uninfected immortalized LI keratinocytes, confirming that these cells were isolated from a patient harboring a natural TGM1 deficiency.

Figure 10A:
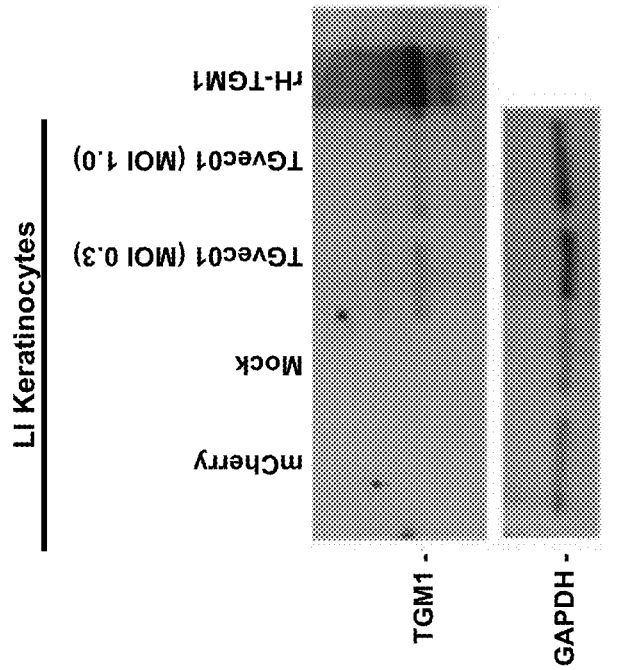
FIGS. 10A-D show human TGM1 protein expression in primary normal and LI keratinocytes infected with TGvec01.
Figure 10B:
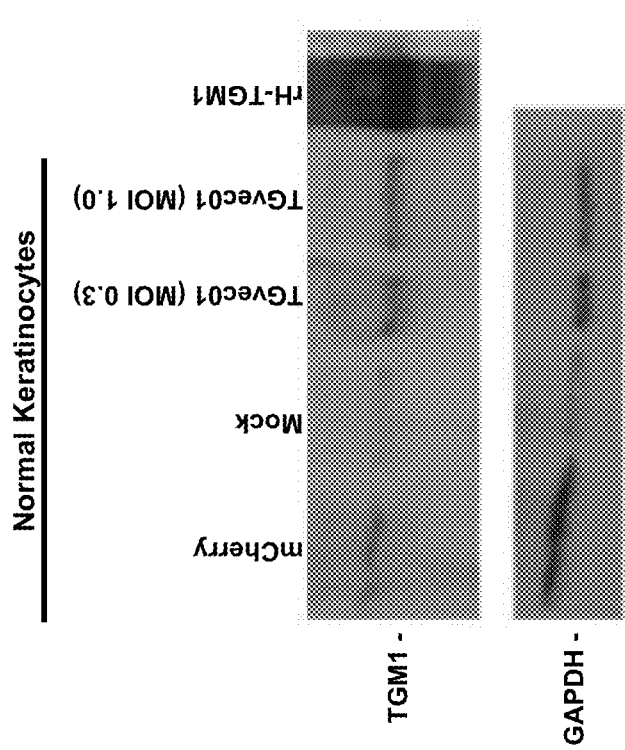

Next, the ability of TGvec01 to transduce primary cells and effectively deliver and express its encoded human TGM1 transgene was evaluated. Primary normal and LI keratinocytes were infected for 48 hours with TGvec01 at different multiplicities of infection ranging from 0-1, and TGM1 expression was determined by western blotting and immunofluorescence. A TGvec01 dose-dependent increase in TGM1 protein level was observed by western blot in primary normal (FIG. 10A) and LI (FIG. 10B) keratinocyte cell lysates. As expected, western blotting indicated that TGM1 was detectable in uninfected primary normal keratinocytes, while no endogenous TGM1 was observed in the negative control primary LI keratinocytes, confirming their status as natural TGM1 mutants.

Figure 10C:
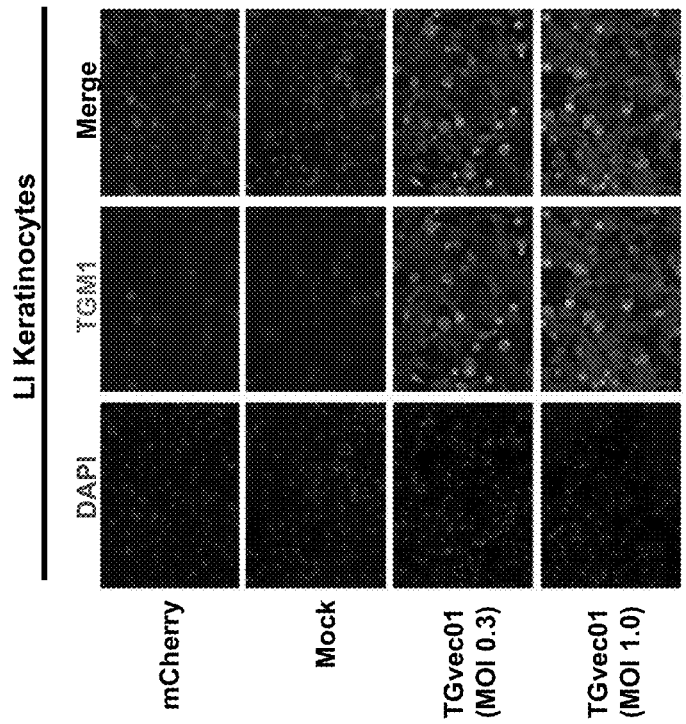
Figure 10D:
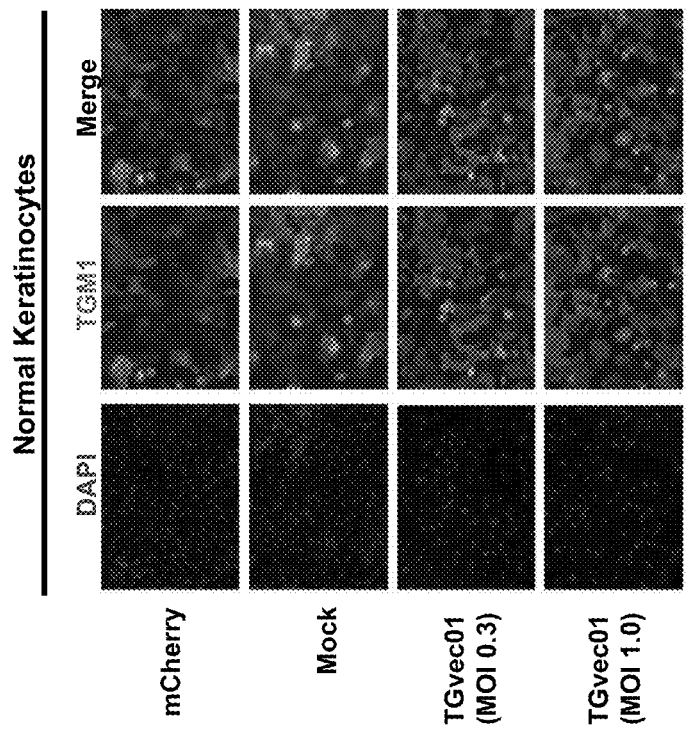

A dose-dependent increase in TGM1 protein was also observed by immunofluorescence between an MOI of 0.3 and 1.0 in primary normal (FIG. 10C) and LI (FIG. 10D) keratinocytes infected with TGvec01. As such, the data indicated that TGvec01 was capable of rescuing TGM1 expression in vitro in otherwise TGM1-deficient primary cells isolated from a patient suffering from lamellar ichthyosis.

Figure 11:
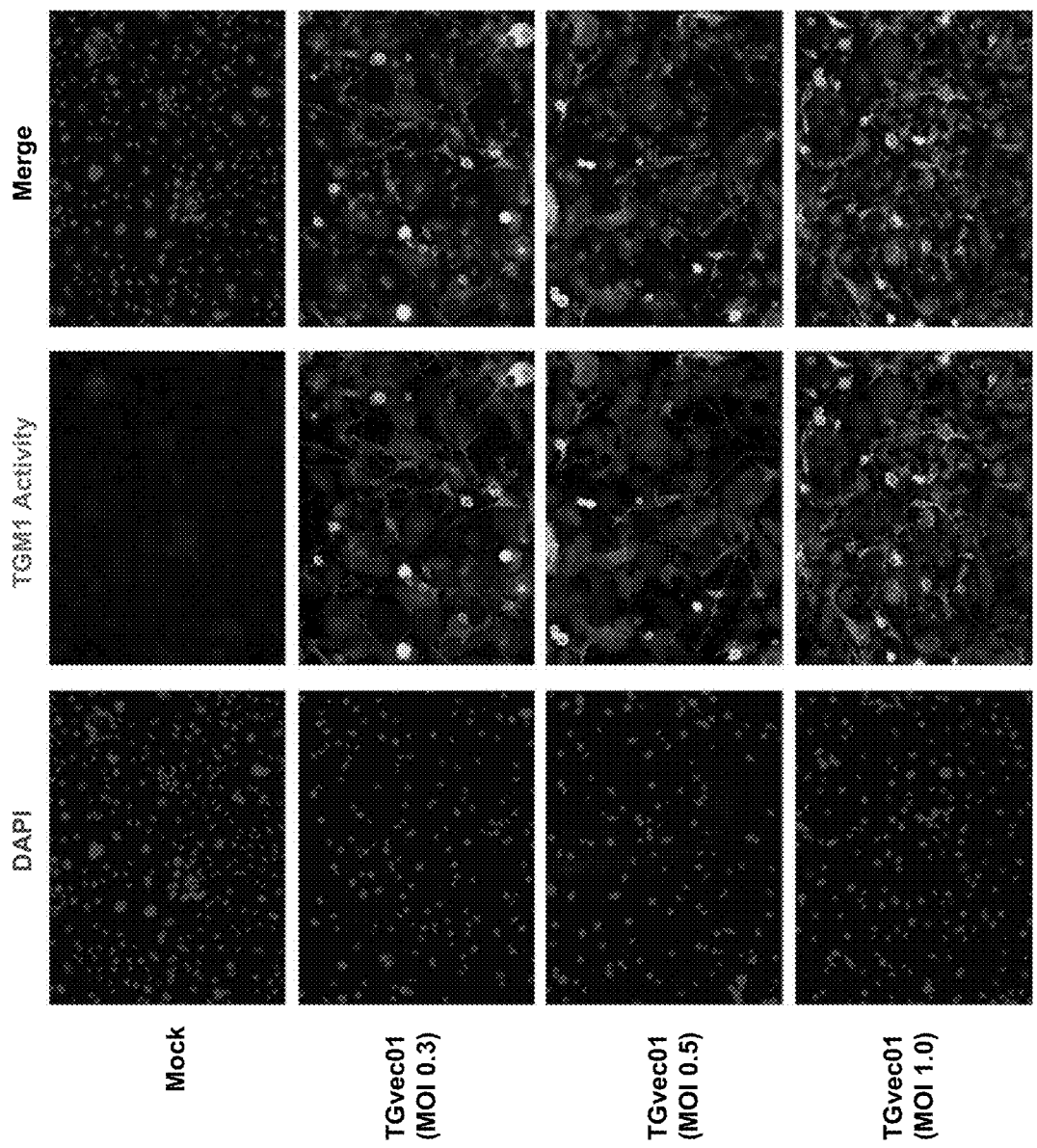
FIG. 11 shows representative immunofluorescence images of TGM1 enzymatic activity in uninfected (mock) immortalized LI patient keratinocytes, or immortalized LI keratinocytes infected with TGvec01 at the indicated MOIs, as assessed by a fluorescent reporter assay measuring cross-linking of a transglutaminase-isoform-specific synthetic peptide. DAPI staining was used to visualize nuclei.

Finally, to show that the TGvec01-expressed TGM1 protein was functional, and in situ activity assay was performed using the immortalized LI patient keratinocytes. Here, a synthetic transglutaminase-isoenzyme specific glutamine donor substrate was used to measure TGM1 activity in the absence and presence of increasing MOIs of TGvec01 in these TGM1-deficient cells after 48 hours of infection. A dose-dependent increase in TGM1 enzymatic activity was observed in these cells by immunofluorescence (FIG. 11), indicating that the HSV-encoded human TGM1 was indeed functional.

Taken together, the data presented in this example demonstrate that an engineered herpes simplex virus can efficiently transduce both immortalized and primary normal and LI patient keratinocytes and produce high levels of exogenous TGM1 after transduction. Importantly, while TGvec01 was capable of rescuing TGM1 expression in patient cells, the vector did not induce any major toxicity in either of the 2D cell culture studies. In addition, the data presented herein indicates that TGvec01 is capable of restoring TGM1 function and enzymatic activity in otherwise TGM1-deficient human cells.

Example 5: Characterization of TGvec01 in 3D Organotypic Cultures

Regenerated human skin equivalents from cultured keratinocytes generated through 3D organotypic culture is a widely used model to monitor the efficacy of therapeutic candidates. The following example describes in vitro experiments establishing a 3D organotypic skin graft model suitable for the study of TGvec01-mediated TGM1 protein expression and enzymatic activity in immortalized LI patient keratinocytes grown on devitalized human dermis.

Materials and Methods

All experiments were conducted as described above unless noted otherwise.

Processing of Human Dermis

Cryopreserved skin grafts were obtained commercially, and the intact package was freeze-thawed three times immediately after shipment by alternately placing in liquid nitrogen and then transferring to, and incubating in, a 37° C. water bath until no bubbles were observed. Following freeze/thaw, the package was moved to a biosafety cabinet, and the skin was removed with sterile forceps and placed in a sterile bottle of 500 mL DPBS+2% antimycotic-antibiotic (2% aa) solution. After incubation for one week in a humidified incubator set at 37° C., the epidermis was separated from the dermis, and the dermis was preserved at 4° C. in fresh DPBS+2% aa. 1 cm$^2$ sections of devitalized dermis were dissected and used for the graft studies.

Seeding Keratinocytes on Human Dermis 1 cm$^2$ sections of dermis were transferred to 12-well transwell cell culture inserts (Millipore Sigma) with the epidermal side facing up. 100 μL of immortalized LI patient keratinocyte cell suspension was then placed in the center of the human dermis, incubated for 15 minutes at room temperature, and then moved to a humidified 37° C. incubator for 30 minutes. After incubation, medium was added to both the inner and outer chambers without disturbing the cells, and the transwells were incubated at 37° C. for another 24 hours.

Virus Infections

Prepared virus was formulated at the desired MOI (as described in the examples above). Medium was removed from the transwell chambers, and the formulated virus was added to each transwell and incubated for 1 hour at 37° C. After incubation, cell culture medium was added to the inner and outer chambers of the transwell without disturbing the cells, and the plate was placed in a humidified 37° C. incubator. After a 48-hour incubation, the skin grafts were introduced to the air-liquid interface to allow for stratification. The cell culture medium in the outer chamber was replaced every other day until completion of the experiment.

TGM1 Immunofluorescence

5 μm slides were dried at 56° C. for 30 minutes followed by fixation with acetone at −20° C. for 10 minutes. 3% hydrogen peroxide was used to block endogenous peroxidase activity. After washing the peroxide treated samples 3× with PBS, Powerblock universal blocking buffer (Biogenex) was applied for 5 minutes at room temperature. Anti-human TGM1 antibody (Abcam, cat. no. ab103814) was diluted 1:200 in Antibody Diluent (ThermoFisher), and diluted antibody was incubated on the slides overnight at 4° C. The following day, slides were washed 3× with TBS+0.025% Triton-100 and stained for 1 hour at room temperature with a 1:200 dilution of Alexa Fluor® 488-conjugated secondary antibody. After thoroughly washing the counterstained slides, the slides were mounted with DAPI-containing mounting medium.

TGM1 In Situ Activity Assays

10 μm slides were dried at 37° C. for 1 hour followed by fixation with acetone at −20° C. for 10 minutes. Sections were blocked with 1% BSA in 01M Tris-HCl for 30 minutes, rinsed once in PBS, then treated with Avidin-Biotin-Block solution (ThermoFisher) per the manufacturer's protocol. Sections were then incubated for 2 hours in the presence of 0.1 mM biotinylated TG-isoform-specific peptide (Zedira) in 0.1M Tris-HCl buffer containing 5 mM $CaCl_2$. Control sections were incubated in the absence of the synthetic peptide. Reactions were stopped with 25 mM EDTA/PBS. Slides were then washed 3× with PBS, and incorporation of biotinylated peptides was visualized by incubation for 30 minutes at room temperature with streptavidin-avidin fluorescein isothiocyanate (ThermoFisher). Nuclei were visualized using DAPI, and background autofluorescence was reduced by treatment with 0.1% Sudan Black for 15 minutes at room temperature.

Results

To establish an in vitro keratinocyte skin grafting model, immortalized LI and normal keratinocytes were seeded onto the dermis of processed human skin samples. Samples were harvested, cryoembedded, and H&E stained 24- and 48-hours post-seeding to evaluate whether a monolayer of keratinocytes had been formed on the human dermis (data not shown). While limited keratinocyte seeding was observed at 24 and 48 hours using both LI and normal keratinocytes, sufficient cell seeding was detected from the LI patient-derived keratinocyte-treated samples in order to perform a 3D organotypic assessment of TGM1 activity after treatment with TGvec01.

Figure 12:
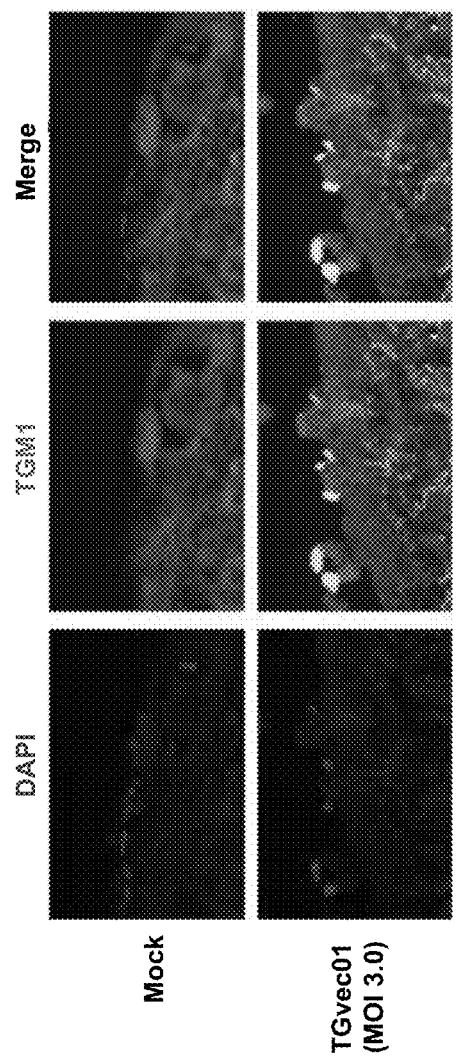
FIG. 12 shows representative immunofluorescence images of human TGM1 protein expression in immortalized LI patient keratinocytes seeded on devitalized human dermis and infected with TGvec01 at an MOI of 3.0. Uninfected (mock) LI patient keratinocytes seeded on human dermis served as a negative control. DAPI staining was used to visualize nuclei.
Figure 13:
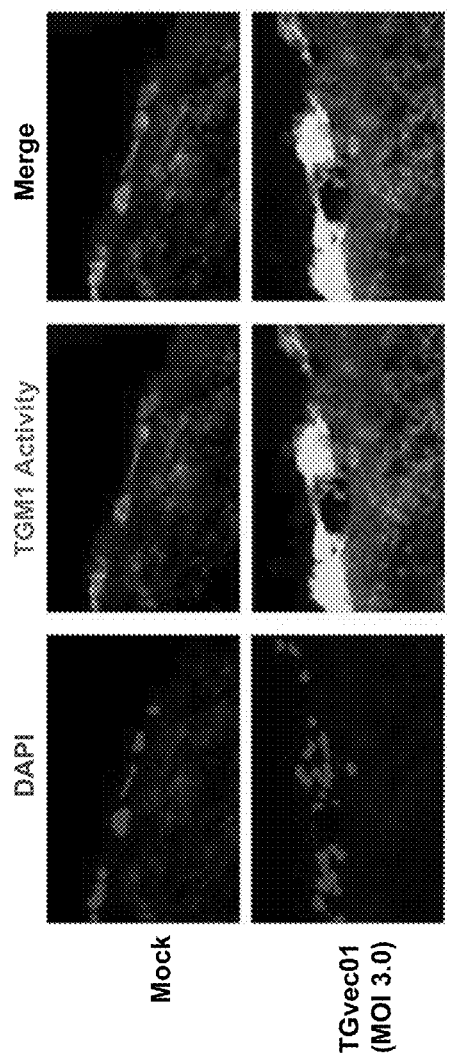
FIG. 13 shows representative immunofluorescence images of TGM1 enzymatic activity in uninfected (mock) immortalized LI patient keratinocytes seeded on devitalized human dermis, or immortalized LI keratinocytes seeded on devitalized human dermis and infected with TGvec01 at an MOI of 3.0, as assessed by a fluorescent reporter assay measuring cross-linking of a transglutaminase-isoform-specific synthetic peptide. DAPI staining was used to visualize nuclei.

Using this 3D system, human TGM1 expression and enzymatic activity in untreated and TGvec01-transduced samples were assessed 6 days post-infection and 5 days after lifting the grafts to the air-liquid interface. Although a confluent monolayer was not observed in the grafts at 5 days post exposure to the air-liquid interface, robust TGM1 protein expression was clearly observed in grafts that were infected with TGvec01, but not in grafts that were mock infected (FIG. 12). Importantly, not only could TGvec01 rescue TGM1 expression in otherwise TGM1-deficient LI patient cells in this skin graft model, but the exogenously expressed TGM1 was determined to be functional. Specifically, a TGvec01-dependent increase in TGM1 enzymatic activity, as determined by cross-linking of a synthetic TG-isoform-specific peptide, was observed by immunofluorescence (FIG. 13). While a dim signal was observed in mock-infected wells, likely due to cross-reactivity of the substrate with TGM2 (a transglutaminase with no underlying genetic lesion in these patient cells), the signal was clearly stronger in the TGvec01-infected wells than in the control wells.

Taken together, the data presented in this example demonstrate that (1) TGvec01 can efficiently transduce LI patient-derived keratinocytes grown on human dermis, and (2) the TGM1 expressed from this vector retains its enzymatic/functional activity. Without wishing to be bound by theory, it is believed that successful use of TGvec01 in this 3D organotypic system lends support to the supposition that TGvec01 would be capable of functionally correcting TGM1 deficiency in ARCI patient skin.

Example 6: In Vivo Characterization of Topically Administered TGvec01

The following example describes in vivo experiments establishing multiple methods of topically administering TGvec01 in healthy immunocompetent animals. These studies were conducted in BALB/c mice since homozygous deletion of mouse TGM1 is neonatal-lethal.

Materials and Methods

All experiments were conducted as described above unless noted otherwise.

All procedures conducted in this example were in compliance with applicable animal welfare acts and were approved by the local Institutional Animal Care and Use Committee (IACUC).

Topical Application of TGvec01

The backs of mice were shaved, and hair follicles were removed with a hair removal product before further manipulations. Tape stripping (using Tegaderm™) and acetone treatment were carried our as described previously (Ekanayake-Mudiyanselage et al. J Invest Dermatol (1998), 111(3): 517-23). To contain the topical formulation at the treatment site, sterile plastic wells covered by a transparent adhesive dressing were adhered to the skin of the animals using surgical glue. TGvec01 (or a corresponding mCherry-expressing virus used as a negative control where indicated) formulated in a methylcellulose gel carrier was then applied to the treatment sites via injection through the transparent adhesive dressing. After infection and the subsequent recovery period, the animals were euthanized, and the treatment sites were removed using an 8 mm punch biopsy. One half of each biopsy was quick-frozen in liquid nitrogen for qPCR/qRT-PCR analysis, while the other half was processed for immunofluorescence analysis.

Tissue samples were processed for nucleic acid and protein analysis as described in Example 3. For TGM1 immunofluorescence staining, a mouse anti-human TGM1 primary antibody (Zedira, clone XTG31) and an Alexa Fluor® 488-conjugated goat anti-mouse secondary antibody (Thermo Fisher, cat. no. A-11029) were used. For loricrin immunofluorescence staining, a rabbit anti-mouse loricrin primary antibody (Abcam, cat. no. ab85679) and an Alexa Fluor® 594-conjugated goat anti-rabbit secondary antibody (Abcam, cat. no. ab150080) were used.

Results

First, a short-term in vivo pharmacokinetic study was conducted to evaluate TGvec01-mediated expression of human TGM1 in immunocompetent mice upon topical administration of the vector. A total of five male BALB/c mice were used for this PK study. The back of each mouse was first shaved and then treated with a chemical agent to remove the hair follicles. Next, the exposed skin was tape-stripped nine times to remove the stratum corneum, and $3.45 \times 10^6$ plaque forming units (PFU) TGvec01 (or mCherry-expressing negative control virus) formulated in a gel carrier was topically administered to two regions of the tape-stripped skin on each mouse. One mouse was sacrificed immediately after being tape-stripped, and before receiving a viral formulation, in order to evaluate efficacy of the tape-stripping. Efficient removal of the stratum corneum via the tape-stripping method was confirmed by histological analysis. Table 2 below provides a synopsis of the experimental design.

TABLE 2 study design and test article administration

| Group No. | N | Test Article | Tape-stripping (day) | Route of Administration | Location, No. of Sites | Termination (day) |
|---|---|---|---|---|---|---|
| 1 | 1 | — | 1 | — | Back or flank, 4 | 1 |
| 2 | 1 | mCherry | 1 | Topical | Back, 2 | 3 |
| 3 | 3 | TGvec01 | 1 | Topical | Back, 2 | 3 |

Figure 14A:
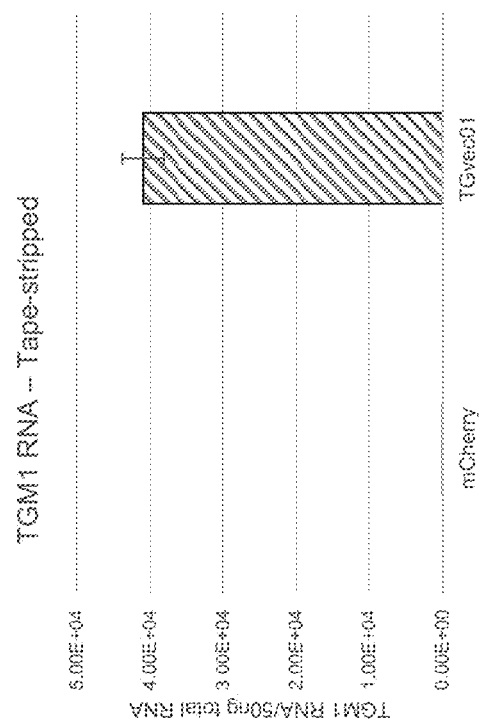
FIGS. 14A-C show nucleic acid and protein analyses of skin biopsies taken from control- or TGvec01-treated BALB/c mice 48 hours after topical application.
Figure 14B:
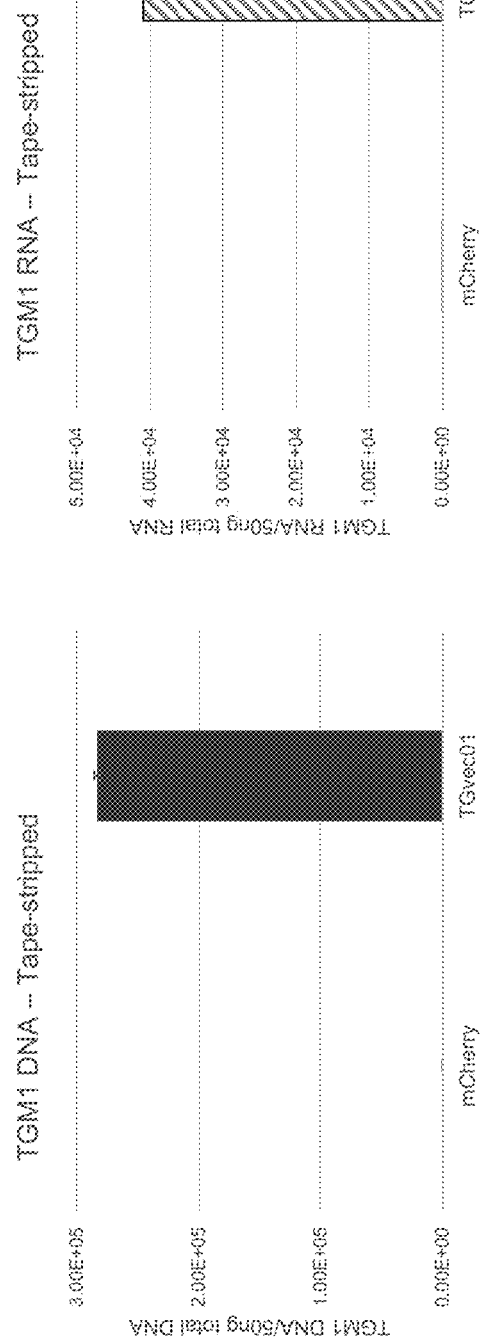

48 hours after topical administration of test or control article, 8 mm skin biopsies were harvested and processed for nucleic acid and protein analysis. qPCR analysis of the topically treated, tape-stripped skin indicated that the engineered HSV genomes encoding the human TGM1 transgene efficiently transduced disrupted skin of immunocompetent animals (FIG. 14A). Not only did the genomes efficiently enter the targeted tissues, but the recombinant human TGM1 was robustly expressed after infection, as assessed by qRT-PCR analysis (FIG. 14B). No TGM1 DNA or RNA was detected in the mCherry-infected tissues, indicating specificity of the assay for the TGvec01 test article.

Figure 14C:
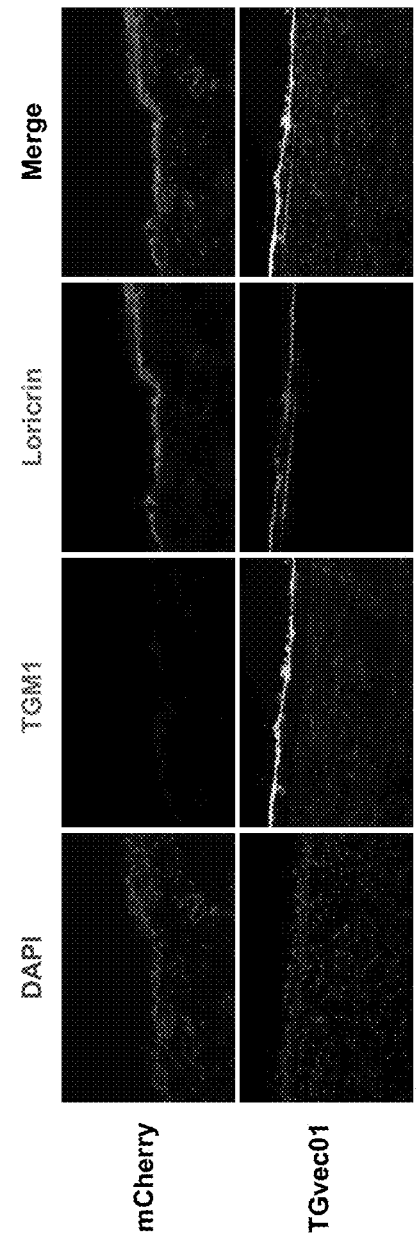

Human TGM1 protein expression and localization in skin samples harvested from topically treated animals were also assessed by immunofluorescence. Human TGM1 protein expression was detected in mouse epidermis upon topical application of TGvec01 (FIG. 14C). It was also important to show that the TGM1 expressed from TGvec01 was correctly localized to the appropriate tissue where endogenous TGM1 would be expected to be both expressed and functionally active (the stratum granulosum). As such, tissue samples were counterstained for mouse loricrin, a known substrate of TGM1, to determine the localization of the TGvec01-expressed transgene (FIG. 14C). Mouse loricrin was detected in the same locale as the human TGM1, suggesting that TGvec01 successfully transduced the targeted epidermal layer. Histological examination of the skin determined that infection with the engineered virus caused no gross damage to the underlying tissue.

The qRT-PCR and immunofluorescence data demonstrate strong TGM1 expression at both the transcript and protein level after topical application of TGvec01 to the disrupted skin of healthy, immunocompetent animals. Furthermore, the immunofluorescence data indicates that the exogenously expressed human transgene co-localizes with a native TGM1 substrate, loricrin, in the mouse epidermis.

Next, an additional in vivo study was conducted to determine whether TGvec01 was capable of delivering its encoded payload after topical delivery to non-abraded skin, or skin disrupted using a method other than tape-stripping. Furthermore, this study was carried out, in part, to determine if a dose-response could be observed in vivo when treating with two different amounts (low vs. high) of TGvec01, as was seen in in vitro experiments employing multiple dosages of this vector in both normal and LI patient-derived cells. A total of 14 male BALB/c mice were used for this study. The back of each mouse was first shaved and then treated with a chemical agent to remove the hair follicles. Next, the exposed skin was left unabraded, or was tape-stripped nine times to remove the stratum corneum or rubbed gently with a cotton swab soaked in acetone to permeabilize the skin. Then, either $1.55 \times 10^7$ (low dose) or $7.73 \times 10^7$ (high dose) PFU of TGvec01 formulated in a gel carrier was topically administered to two regions of the prepared skin on each mouse. Table 3 below provides a synopsis of the experimental design.

TABLE 3 study design and test article administration

| Group No. | N | Test Article | Skin Treatment (day) | Route of Administration | Location, No. of Sites | Termination (day) |
|---|---|---|---|---|---|---|
| 1 | 1 | Vehicle | 1 (Tape-stripped) | Topical | Back, 2 | 3 |
| 2 | 1 | Vehicle | 1 (Acetone) | Topical | Back, 2 | 3 |
| 3 | 2 | TGvec01 (high dose) | 1 (No abrasion) | Topical | Back, 2 | 3 |
| 4 | 2 | TGvec01 (low dose) | 1 (No abrasion) | Topical | Back, 2 | 3 |
| 5 | 2 | TGvec01 (high dose) | 1 (Tape-stripped) | Topical | Back, 2 | 3 |
| 6 | 2 | TGvec01 (low dose) | 1 (Tape-stripped) | Topical | Back, 2 | 3 |
| 7 | 2 | TGvec01 (high dose) | 1 (Acetone) | Topical | Back, 2 | 3 |
| 8 | 2 | TGvec01 (low dose) | 1 (Acetone) | Topical | Back, 2 | 3 |

48 hours after treatment, skin biopsies were harvested and processed for nucleic acid analysis. qPCR data indicated that while TGvec01 most efficiently transduced the tape-stripped skin, the virus was also capable of infecting acetone-treated skin (and, to a lesser extent, unabraded skin) after topical administration (FIG. 15A). Paralleling the qPCR data, the highest concentration of TGM1 transcripts were observed in the high-dose, tape-stripped skin by qRT-PCR; however, TGM1 transcripts were also observed in acetone-treated and non-disrupted skin at both low and high doses (FIG. 15B). This data indicated that TGvec01 could efficiently deliver the human transglutaminase when administered topically to skin in various states of disruption.

Without wishing to be bound by theory, the data presented thus far supports the use of TGvec01 as a safe topical gene therapy for administering human TGM1 to the epidermis of disrupted and non-disrupted skin.

Finally, a repeat-dose GLP toxicology and biodistribution study was conducted in healthy, immunocompetent male and female mice. Five weekly topical doses of TGvec01 was found to be well tolerated after long-term follow up, and further, the vector remained localized to the application site with little to no systemic exposure (data not shown).

Without wishing to be bound by theory, it is believed that the data from the 2D, 3D, and in vivo models presented in these examples supports the use of engineered HSV vectors for delivering and expressing functional transglutaminase enzymes (e.g., to transglutaminase-deficient cells), and in particular, supports the use of an engineered HSV-1 vector encoding human TGM1 as a gene therapy useful for the treatment of ARCI (e.g., when administered intradermally and/or topically).

What is claimed is:

1. A pharmaceutical composition comprising:
   (a) a replication defective herpes simplex virus type 1 (HSV-1) comprising a recombinant HSV-1 genome, wherein the recombinant HSV-1 genome comprises one or more polynucleotides encoding a transglutaminase (TGM) polypeptide; and
   (b) a pharmaceutically acceptable excipient.

2. The pharmaceutical composition of claim 1, wherein the TGM polypeptide is selected from the group consisting of a TGM1 polypeptide, a TGM2 polypeptide, a TGM3 polypeptide, a TGM4 polypeptide, a TGM5 polypeptide, a TGM6 polypeptide, and a TGM7 polypeptide.

3. The pharmaceutical composition of claim 1, wherein the TGM polypeptide is a human TGM polypeptide.

4. The pharmaceutical composition of claim 1, wherein the pharmaceutical composition is suitable for topical, transdermal, subcutaneous, intradermal, or transmucosal administration.

5. The pharmaceutical composition of claim 1, wherein the pharmaceutical composition is suitable for topical administration.

6. The pharmaceutical composition of claim 1, wherein the recombinant HSV-1 genome further comprises one or more polynucleotides encoding a glycoprotein H (gH) polypeptide.

7. The pharmaceutical composition of claim 6, wherein the gH polypeptide is a wild-type gH polypeptide.

8. The pharmaceutical composition of claim 1, wherein the recombinant HSV-1 genome further comprises an inactivating mutation in an essential immediate early gene.

9. The pharmaceutical composition of claim 8, wherein the essential immediate early gene is one or both copies of an infected Cell Protein (ICP) 4 gene.

10. The pharmaceutical composition of claim 8, wherein the essential immediate early gene is an ICP27 gene.

11. A method of delivering one or more polynucleotides encoding a transglutaminase polypeptide into one or more cells of a subject, the method comprising administering to the subject an effective amount of a pharmaceutical composition comprising:
   (a) a replication defective herpes simplex virus type 1 (HSV-1) comprising a recombinant HSV-1 genome, wherein the recombinant HSV-1 genome comprises the one or more polynucleotides encoding a human transglutaminase (TGM) polypeptide; and
   (b) a pharmaceutically acceptable excipient.

12. The method of claim 11, wherein the subject is a human.

13. The method of claim 11, wherein the pharmaceutical composition is administered topically, transdermally, subcutaneously, intradermally, or transmucosally to the subject.

14. The method of claim 11, wherein the pharmaceutical composition is administered topically to the subject.

15. The method of claim 11, wherein the human TGM polypeptide is selected from the group consisting of a human TGM1 polypeptide, a human TGM2 polypeptide, a human TGM3 polypeptide, a human TGM4 polypeptide, a human TGM5 polypeptide, a human TGM6 polypeptide, and a human TGM7 polypeptide.

16. The method of claim 11, wherein the one or more cells are one or more cells of the skin.

17. The method of claim 11, wherein the recombinant HSV-1 genome further comprises one or more polynucleotides encoding a gH polypeptide.

18. The method of claim 17, wherein the gH polypeptide is a wild-type gH polypeptide.

19. The method of claim 11, wherein the recombinant HSV-1 genome further comprises an inactivating mutation in an essential immediate early gene.

20. The method of claim 19, wherein the essential immediate early gene is one or both copies of an ICP4 gene.

21. The method of claim 19, wherein the essential immediate early gene is an ICP27 gene.

* * * * *

SEQUENCE LISTING

<160> NUMBER OF SEQ ID NOS: 10

<210> SEQ ID NO 1
<211> LENGTH: 2454
<212> TYPE: DNA
<213> ORGANISM: Homo sapiens

<400> SEQUENCE: 1

```
atgatggatg ggccacgttc cgatgtgggc cgttggggtg caaccccctt gcagcccct      60 accacgccat ctccagagcc agagccagag ccagacggac gctctcgcag aggaggaggc     120
cgttccttct gggctcgctg ctgtggctgc tgttcatgcc gaaatgcggc agatgacgac     180 tgggacctg aaccctctga ctccagggt cgagggtcca gctctggcac tcgaagacct      240
ggctcccggg gctcagactc ccgccggcct gtatcccggg gcagcggtgt caatgcagct     300
ggagatggca ccatccgaga gggcatgcta gtagtgaacg tgtggactt gctgagctcg      360 cgctcggacc agaaccgccg agagcaccac acagacgagt atgagtacga cgagctgata     420
gtgcgccgcg ggcagccttt ccatatgctc ctcctcctgt cccggaccta tgaatcctct      480
gatcgcatca cccttgagtt actcatcgga aacaaccccg aggtgggcaa gggcacgcac     540
gtgatcatcc cagtgggcaa gggggggcagt ggaggctgga aagcccaggt ggtcaaggcc    600
agtgggcaga atctgaacct gcgggtccac acttccccca acgccatcat cggcaagttt     660
cagttcacag tccgcacaca atcagacgct ggggagttcc agttgccctt tgaccccgc     720 aatgagatct acatcctctt caaccccctgg tgcccagagg acattgtgta cgtggaccat     780
gaggattggc ggcaggagta tgttcttaat gagtctggga gaatttacta cgggaccgaa     840
gcacagattg gtgagcggac ctggaactac ggccagtttg accacggggt gctggatgcc     900
tgcttataca tcctggaccg gcgggggatg ccatatggag gccgtggaga cccagtcaat     960
gtctcccggg tcatctctgc catggtgaac tccctggatg acaatggagt cctgattggg    1020
aactggtctg tgattactc ccgaggcacc aacccatcag cgtgggtggg cagcgtggag    1080
atcctgctta gctacctacg cacgggatat tccgtcccct atggccagtg ctgggtcttt   1140
gctggcgtga ccaccacagt gctgcgctgc ctgggtctgg ccacccgtac tgtcaccaac    1200
ttcaactccg cccacgacac agacacatcc cttaccatgg acatctactt cgacgagaac    1260
atgaagcccc tggagcacct gaaccatgat tctgtctgga acttccatgt gtggaacgac    1320
tgctggatga agaggccgga tctgcccctcg ggctttgatg gtggcaggt ggtggatgcc    1380 acacccccaag agactagcag tggcatcttc tgctgcggcc cctgctctgt ggagtccatc    1440
aagaatggcc tggtctacat gaagtacgac acgcctttca ttttgctga ggtgaatagt     1500 gacaaggtgt actggcagcg gcaggatgat ggcagcttca gattgttta tgtggaggag    1560 aaggccatcg gcacactcat tgtcacaaag gccatcagct ccaacatgcg ggaggacatc    1620
acctacctct ataagcaccc agaaggctca gacgcagagc ggaaggcagt agagacagca    1680
```

-continued

```
gcagcccacg gcagcaaacc caatgtgtat gccaaccggg gctcagcgga ggatgtggcc      1740
atgcaggtgg aggcacagga cgcggtgatg gggcaggatc tgatggtctc tgtgatgctg      1800
atcaatcaca gcagcagccg ccgcacagtg aaactgcacc tctacctctc agtcactttc      1860
tatactggtg tcagtggtac catcttcaag gagaccaaga aggaagtgga gctggcacca      1920
ggggcctcgg accgtgtgac catgccagtg gcctacaagg aataccggcc ccatcttgtg      1980 gaccagggg ccatgctgct caatgtctca ggccacgtca aggagagcgg gcaggtgctg       2040
gccaagcagc acaccttccg tctgcgcacc ccagacctct ccctcacgtt actgggagca      2100
gcagtggttg gccaggagtg tgaagtacag attgtcttca agaacccct tcccgtcacc       2160 ctcaccaatg tcgtcttccg gctcgaaggc tctgggttac agaggcccaa gatcctcaac      2220
gttggggaca ttggaggcaa tgaaacagtg acactgcgcc agtcgtttgt gcctgtgcga      2280 ccaggcccc gccagctcat tgccagcttg acagcccac agctctccca ggtgcacggt        2340
gtcatccagg tggatgtggc cccagcccct ggggatgggg gcttcttctc agacgctgga      2400
ggtgacagtc acttaggaga gaccatccct atggcatctc gaggtggagc ttag            2454
```

<210> SEQ ID NO 2
<211> LENGTH: 2454
<212> TYPE: DNA
<213> ORGANISM: Artifical Sequence
<220> FEATURE:
<223> OTHER INFORMATION: Synthetic Construct

<400> SEQUENCE: 2

```
atgatggacg ccctagatc cgatgttggc agatggggcg gaaaccctct gcagcctcct       60
accacacctt ctccagagcc tgaacctgag cctgacggca gatctagaag aggcggcgga     120
agatccttct gggccagatg ctgtggctgc tgcagctgta gaaacgccgc cgacgatgat     180
tggggccctg agccttctga tagcagaggc agaggctcta gcagcggcac aagaaggcct    240
ggctctagag gcagcgatag cagacggcct gtgtccagag gttctggcgt gaacgctgct    300
ggcgacggca caatcagaga aggcatgctg gtggtcaacg gcgtggacct gctgagcagc    360
agaagcgacc agaacagaag agagcaccac accgacgagt acgagtatga cgagctgatc    420
gtgcggagag gccagccttt tcacatgttg ctgctgctga gccggaccta cgagagcagc    480
gacagaatca ccctggaact gctgatcggc aacaaccccg aagtcggcaa gggcacccac    540
gtgatcatcc ctgttggcaa aggtggcagc ggaggatgga agcccaggt ggtcaaagcc      600 agcggccaga tctgaatct gcgggtgcac acaagcccca cgccatcat cggcaagttc     660 cagtttaccg tgcggaccca gtctgacgcc ggcgaatttc agctgcctt cgatccccgg     720 aacgagatct acatcctgtt caacccttgg tgccccgagg catcgtgta cgtggaccac     780 gaggattggc ggcaagagta cgtgctgaac gagagcggca ggatctacta cggaacagag    840
gcccagatcg cgagcggac atggaattac ggccagttcg atcacggcgt gctggacgcc     900
tgtctgtaca tcctggatag acgcggcatg ccctatggcg aagaggcga tcctgtgaat     960 gtgtctagag tgatcagcgc catggtcaac agcctggacg acaatggcgt gctgattggc    1020
aattggagcg cgactacag caggggcaca aatccatctg cctgggtcgg aagcgtggaa     1080
atcctgctgt cctacctgag aaccggctac agcgtgccct acggacagtg ttgggttttc    1140
gctggcgtga ccaccaccgt gctgagatgt ctgggactcg ccaccagaac cgtgaccaac    1200
ttcaacagcg cccacgacac cgataccagc ctgaccatgg acatctactt cgacgagaac    1260
atgaagcccc tggaacacct gaaccacgac agcgtgtgga acttccacgt gtggaatgac    1320
```

```
tgctggatga agcggcccga tctgccctct ggattcgatg gatggcaggt cgtggacgcc    1380
acacctcaag agacaagctc cggcatcttc tgctgtggcc cttgcagcgt ggaatccatc    1440
aagaacggac tggtgtacat gaagtacgac acgcccttca tcttcgccga agtgaacagc    1500
gacaaggtgt actggcagag acaggacgac ggcagcttca agattgtgta tgtggaagag    1560
aaggccatcg gcaccctgat cgtgaccaag gccatcagct ccaacatgag agaggacatc    1620
acctacctgt acaagcaccc cgagggctcc gatgccgaga aaaagctgt ggaaacagct    1680 gccgctcacg gcagcaagcc taacgtgtac gccaatagag ctccgccga ggacgtggcc    1740 atgcaggttg aagctcagga tgccgtgatg gccaagacc tgatggtgtc cgtgatgctg    1800
atcaaccaca gcagctccag acggaccgtg aagctgcacc tgtacctgtc cgtgaccttc    1860
tacacaggcg tgtccggcac catcttcaaa gaaacaaaga agaggtcga gctggcccca    1920 ggcgccagcg atagagttac aatgcccgtg cctacaaag agtacagacc ccacctggtg    1980
gatcagggcg ctatgctgct gaatgtctcc ggccacgtga agaaagcgg acaggtgctg    2040 gccaagcagc acaccttcag actgagaacc cctgatctgt ctctgaccct gctgggagcc    2100
gctgttgtgg acaagagtg cgaggtgcag atcgtgttca agaatcccct gcctgtgaca    2160
ctgaccaacg tggtgttcag actggaaggc tctggcctgc agcggcctaa gatcctgaat    2220
gtgggagaca tcggcggcaa cgagacagtg accctgagac agagctttgt gcctgtgcgg    2280
cctggaccta gacagctgat tgccagcctg gatagcccac agctgtctca agtgcacggc    2340
gtgatccagg tggacgttgc accagctcca ggcgacggcg gctttttttc tgatgccggc    2400
ggagattctc acctgggcga gacaattccc atggccagta gaggcggagc ttga          2454
```

<210> SEQ ID NO 3
<211> LENGTH: 2448
<212> TYPE: DNA
<213> ORGANISM: Mus musculus

<400> SEQUENCE: 3

```
atggaaggtc ctcgctcaga cgtgggccgc tggggcagga gcccctggca gcccccctaca    60 acaccgtcac cggagccaga gccggtgccg agccagaca gacgctcgcg ctcccgccga    120
ggaggaggcc gctccttctg ggctcgttgt tgtggctgct gctcatgtgg aacagaggg    180 gacgatgact ggggacctga accttctggc tccagaagca gagggaccag ctcccggggt    240
agggactctc ggggtggccg aagacccgag tctcggggca gtggtgtaaa tgcagctgga    300
gatggcacca tccgagaggg aatgctggtt gtgactggtg tggatctgct gtgctcacga    360
tcagaccaga accgccgaga gcaccacacg gatgagtttg aatatgatga gctgattgtg    420
cgccgtgggc agcccttcca catgatcctt ttcttgaacc gggaatatga gtcctctgat    480
cgcattgccc ttgagctcct cattggaagc aatccggagg tgggcaaggg cacccacgtg    540
atcatcccag tgggtaaggg aggcagtggt ggctggaagg cccaagtgac taagaacaac    600
ggacacaacc taaacctacg cgtccacacc tcccccaatg ccatcattgg caagtttcag    660
ttcactgtcc gcaccgcttc tgaagctgga gagttccagt tgccctttga cccccgcaat    720
gagatctaca tcctctttca atccctggtgc ccagaggaca tagtgtatgt ggaccatgag    780
gactggcggc aagaatatgt gcttaatgag tctggaagaa tctactatgg aacagaagca    840
cagattggcg aacgaacctg gaactatggt cagtttgacc atggggtgct ggatgcctgc    900
ctgtacatcc tggatcggag ggggatgcca tatggaggtc gtggggaccc agtcagtgtc    960
```

```
tctcggggttg tctctgccat ggtgaactcc ctggatgaca atggagttct gattgggaac      1020
tggaccggtg actactctcg aggcaccaac ccctcagcgt gggtgggcag tgtggagatc      1080
ctgctcagct acctacgcac cggctattcc gtccctacg gccaatgctg ggtcttttgcc     1140
ggtgtgacca ccacagtgct ccgatgtctg ggcttcgcta cccgtaccgt caccaacttc      1200
aactctgcac acgacacaga cacctccctc actatggaca tctactttga tgagaacatg      1260
aagccacttg aacatctgaa ccatgattct gttttggaact tccacgtgtg aacgactgc      1320
tggatgaaga ggccagatct gccctcaggc tttgatgggt ggcaggttgt ggatgccaca      1380
ccccaggaga ccagcagtgg catcttctgc tgtggcccct gttctgtgga gtccgtcaag      1440
aatggcttag tctacatgaa gtatgacaca ccttttcattt ttgctgaggt aaatagcgat    1500
aaggtatact ggcagcggca ggatgatggc agctttaaga tagtgtacgt ggaagagaaa     1560
gccattggca cactcattgt cacaaaggcg atccactcca caatcgaga ggacatcacc      1620
cacatctata agcacccaga aggctcagaa gcagagcgga gggctgtgga aaggcggca      1680
gcccatggca gcaaacctaa tgtgtatgcc acccgggact ccgctgagga tgtggcaatg     1740
caggtggagg cgcaggacgc tgtgatgggg caggatctgg ctgtctctgt ggtgctgacc     1800
aatcgtggta gtagccgacg cactgtgaag ttgcacctct acctttgtgt cacctactac    1860
actggtgtct ctgggcctac cttcaaggag gccaaaaagg aagtgacatt agccccagga     1920
gcctcggact ctgtgaccat gcctgtggcc tacaaggaat acaagcccca ccttgtggac    1980
caggggggcaa tgttgctcaa tgtctcaggc catgtcaagg agagtgggca ggtactagcc    2040
aagcaacaca ccttccgttt gcgcacccca gacctttctc ttacgttact gggagcagca    2100
gttgttggtc aggaatgtgg agtacagatc gtgttcaaga accccctgcc tgtcaccctc    2160
accaacgtcg tcttccggct cgaaggttct ggattacaga gacccaaggt cctcaatgtc    2220
ggggacatcg ggggtaatga gacagtcaca ctgcgccaga cgtttgttcc cgtgcgacca    2280
ggcccccgcc agctcattgc cagcctggac agtccacagc tttcccaagt gcacggtgtt    2340
attcaagtgg atgtggcccc agcctctgga ggcagcggtt tctcagatgc tggaggtgac    2400
agtcgctctg gggagaacat acctatggca tatcgaggtg gagcttaa                  2448
```

<210> SEQ ID NO 4
<211> LENGTH: 2475
<212> TYPE: DNA
<213> ORGANISM: Rattus norvegicus

<400> SEQUENCE: 4

```
atggaaggtc ctcgctcaga cgtgggccgc tgggggtagga gcccctggca gcccacgaca       60
ccgtcgccag agccagagcc agagccgag ccagacagaa gctcgcgctc cgccgagga        120
ggaggccgct ccttctgggc tcgctgttgt ggctgctgct cctgcgggaa cagagctgat      180
gatgactggg gacccgaacc ttctggctcc agaagccgag ggaccagctc ccggggtgga     240
ggctcccggg gtggggactc tcggggtagg gactctcgag gtggccgaag acctgagtct     300
cggggcagtg gtgtgaatgc agctggagat ggcaccatcc gagagggaat gctggttgtg     360
aatggtgtag atctgctgtg ctcgcgatca gaccagaacc gccgagagca ccacaccgat     420
gagtttgaat atgacgagct aattttgcgc cgtgggcagc ccttccacat aatcctcttc     480
ctgaaccggg agtatgagtc ctctgatcgc attgcccttg agcttctcat cggaaacaat     540
cctgaggtgg gcaagggcac ccacgtgatc atcccagtgg gtaagggagg cagcggtggc     600
tggaaggccc aagtgactaa gaccaatgga cacaacctaa ccctgcgcgt ccacaccctcc    660
```

-continued

```
cctaatgcca tcattggcaa gtttcaattc actgtccgta cacgctcaga ggctggcgag      720
ttccagctgc cctttgaccc ccgcaatgag atctacatcc tcttcaatcc ctggtgtcca      780
gaggacatag tgtatgtgga ccacgaagac tggcgacaag aatatgtgct taatgagtct      840
ggaagaatct actatgggac agaagcacag attggcgaac ggacctggaa ttatggccag      900
tttgaccatg gggtgctgga tgcctgcctg tacattctgg atcggagggg gatgccatat      960
ggaggtcgcg gggacccagt cagtgtctct cgggtcgtct ctgccatggt gaactccctg     1020
gatgacaatg gagttctgat tgggaactgg actggcgact actctcgagg caccaatccc     1080
tcagcgtggg tgggcagtgt ggagatcctg cttagctacc tacgcaccgg ctattccgtc     1140
ccctatggcc aatgctgggt ctttgccggt gtgaccacca cagtgctccg atgtctgggc     1200
cttgctaccc gtactgtcac caacttcaac tctgcacacg acacggacac gtccctcact     1260
atggacattt attttgatga acatgaag ccactggagc acctgaacca cgattctgtt      1320
tggaacttcc acgtgtggaa cgactgctgg atgaagaggc cagatctgcc ctcaggcttt     1380
gatgggtggc aggttgtgga tgccacaccc caggagacca gcagtggcat cttctgctgt     1440
ggcccctgtt cagtggagtc catcaagaat ggcttagtct acatgaagta tgacacacct     1500 ttcattttg ccgaggtaaa cagtgataag gtatactggc agcggcagga tgacggcagc      1560
ttcaagatcg tgtatgtgga agagaaagcc attggcacac tgattgtcac aaaggcgatc     1620
aactccaaca tgcgagagga catcacccac atctataagc acccagaagg ctcagaagca     1680
gagaggaagg ctgtggaaaa ggctgcggcc catggcagca aacctaatgt gtatgccacc     1740
cgggactctg ctgaggatgt ggcaatgcag gtggaggcac aggatgctgt gatggggcag     1800
gatctgactg tctctgtggt gttgaccaat cgtggcagta gccgacgcac tgtgaagttg     1860
cacctctacc tttgtgtcac ctactacact ggtgtctctg ggcctacctt caaggagacc     1920
aagaaagaag tggtattagc cccaggagcc tcggacactg tggccatgcc tgtggcctac     1980
aaggaataca agccccacct tgtggaccag ggggcaatgt tgctcaatgt ctcaggccat     2040
gtcaaggaga gtgggcaggt actagccaag caacacacct tccgtttgcg cacccccagac    2100 ctctctctga cattactggg agctgcagta gttggccagg aatgtgaagt ccagatcgtg     2160
ttcaagaacc ccctgcctat cacccctcacc aacgttgtct ccggctcga aggttctggg     2220 ttacagagac ccaaggtcct caatgttggg gacatcgggg gtaacgagac ggttacactg     2280
cgccagacat tgttcctgt gcgaccaggc ccccgccagc tcattgccag tctggacagt     2340
ccacagcttt cccaagtaca cggtgtcatt caagtggatg tggccccatc ctctggaggc     2400
agaggtttct cagaggctgt aggtgacagt cgctccgggg agaacatacc tatggcattt     2460
cgaggtggag cttag                                                      2475
```

<210> SEQ ID NO 5
<211> LENGTH: 817
<212> TYPE: PRT
<213> ORGANISM: Homo sapiens

<400> SEQUENCE: 5

Met Met Asp Gly Pro Arg Ser Asp Val Gly Arg Trp Gly Gly Asn Pro
1               5                   10                  15

Leu Gln Pro Pro Thr Thr Pro Ser Pro Glu Pro Glu Pro Glu Pro Asp
            20                  25                  30

Gly Arg Ser Arg Arg Gly Gly Gly Arg Ser Phe Trp Ala Arg Cys Cys
        35                  40                  45

```
Gly Cys Cys Ser Cys Arg Asn Ala Ala Asp Asp Trp Gly Pro Glu
 50                  55                  60

Pro Ser Asp Ser Arg Gly Arg Gly Ser Ser Gly Thr Arg Arg Pro
 65                  70                  75                  80

Gly Ser Arg Gly Ser Asp Ser Arg Arg Pro Val Ser Arg Gly Ser Gly
                 85                  90                  95

Val Asn Ala Ala Gly Asp Gly Thr Ile Arg Glu Gly Met Leu Val Val
            100                 105                 110

Asn Gly Val Asp Leu Leu Ser Ser Arg Ser Asp Gln Asn Arg Arg Glu
        115                 120                 125

His His Thr Asp Glu Tyr Glu Tyr Asp Glu Leu Ile Val Arg Arg Gly
    130                 135                 140

Gln Pro Phe His Met Leu Leu Leu Ser Arg Thr Tyr Glu Ser Ser
145                 150                 155                 160

Asp Arg Ile Thr Leu Glu Leu Leu Ile Gly Asn Asn Pro Glu Val Gly
                165                 170                 175

Lys Gly Thr His Val Ile Ile Pro Val Gly Lys Gly Ser Gly Gly
            180                 185                 190

Trp Lys Ala Gln Val Val Lys Ala Ser Gly Gln Asn Leu Asn Leu Arg
        195                 200                 205

Val His Thr Ser Pro Asn Ala Ile Ile Gly Lys Phe Gln Phe Thr Val
    210                 215                 220

Arg Thr Gln Ser Asp Ala Gly Glu Phe Gln Leu Pro Phe Asp Pro Arg
225                 230                 235                 240

Asn Glu Ile Tyr Ile Leu Phe Asn Pro Trp Cys Pro Glu Asp Ile Val
                245                 250                 255

Tyr Val Asp His Glu Asp Trp Arg Gln Glu Tyr Val Leu Asn Glu Ser
            260                 265                 270

Gly Arg Ile Tyr Tyr Gly Thr Glu Ala Gln Ile Gly Glu Arg Thr Trp
        275                 280                 285

Asn Tyr Gly Gln Phe Asp His Gly Val Leu Asp Ala Cys Leu Tyr Ile
    290                 295                 300

Leu Asp Arg Arg Gly Met Pro Tyr Gly Gly Arg Gly Asp Pro Val Asn
305                 310                 315                 320

Val Ser Arg Val Ile Ser Ala Met Val Asn Ser Leu Asp Asp Asn Gly
                325                 330                 335

Val Leu Ile Gly Asn Trp Ser Gly Asp Tyr Ser Arg Gly Thr Asn Pro
            340                 345                 350

Ser Ala Trp Val Gly Ser Val Glu Ile Leu Leu Ser Tyr Leu Arg Thr
        355                 360                 365

Gly Tyr Ser Val Pro Tyr Gly Gln Cys Trp Val Phe Ala Gly Val Thr
    370                 375                 380

Thr Thr Val Leu Arg Cys Leu Gly Leu Ala Thr Arg Thr Val Thr Asn
385                 390                 395                 400

Phe Asn Ser Ala His Asp Thr Asp Thr Ser Leu Thr Met Asp Ile Tyr
                405                 410                 415

Phe Asp Glu Asn Met Lys Pro Leu Glu His Leu Asn His Asp Ser Val
            420                 425                 430

Trp Asn Phe His Val Trp Asn Asp Cys Trp Met Lys Arg Pro Asp Leu
        435                 440                 445

Pro Ser Gly Phe Asp Gly Trp Gln Val Val Asp Ala Thr Pro Gln Glu
    450                 455                 460
```

```
Thr Ser Ser Gly Ile Phe Cys Cys Gly Pro Cys Ser Val Glu Ser Ile
465                 470                 475                 480

Lys Asn Gly Leu Val Tyr Met Lys Tyr Asp Thr Pro Phe Ile Phe Ala
            485                 490                 495

Glu Val Asn Ser Asp Lys Val Tyr Trp Gln Arg Gln Asp Asp Gly Ser
        500                 505                 510

Phe Lys Ile Val Tyr Val Glu Lys Ala Ile Gly Thr Leu Ile Val
    515                 520                 525

Thr Lys Ala Ile Ser Ser Asn Met Arg Glu Asp Ile Thr Tyr Leu Tyr
530                 535                 540

Lys His Pro Glu Gly Ser Asp Ala Glu Arg Lys Ala Val Glu Thr Ala
545                 550                 555                 560

Ala Ala His Gly Ser Lys Pro Asn Val Tyr Ala Asn Arg Gly Ser Ala
                565                 570                 575

Glu Asp Val Ala Met Gln Val Glu Ala Gln Asp Ala Val Met Gly Gln
            580                 585                 590

Asp Leu Met Val Ser Val Met Leu Ile Asn His Ser Ser Ser Arg Arg
        595                 600                 605

Thr Val Lys Leu His Leu Tyr Leu Ser Val Thr Phe Tyr Thr Gly Val
    610                 615                 620

Ser Gly Thr Ile Phe Lys Glu Thr Lys Lys Glu Val Glu Leu Ala Pro
625                 630                 635                 640

Gly Ala Ser Asp Arg Val Thr Met Pro Val Ala Tyr Lys Glu Tyr Arg
                645                 650                 655

Pro His Leu Val Asp Gln Gly Ala Met Leu Leu Asn Val Ser Gly His
            660                 665                 670

Val Lys Glu Ser Gly Gln Val Leu Ala Lys Gln His Thr Phe Arg Leu
        675                 680                 685

Arg Thr Pro Asp Leu Ser Leu Thr Leu Leu Gly Ala Ala Val Val Gly
    690                 695                 700

Gln Glu Cys Glu Val Gln Ile Val Phe Lys Asn Pro Leu Pro Val Thr
705                 710                 715                 720

Leu Thr Asn Val Val Phe Arg Leu Glu Gly Ser Gly Leu Gln Arg Pro
                725                 730                 735

Lys Ile Leu Asn Val Gly Asp Ile Gly Gly Asn Glu Thr Val Thr Leu
            740                 745                 750

Arg Gln Ser Phe Val Pro Val Arg Pro Gly Pro Arg Gln Leu Ile Ala
        755                 760                 765

Ser Leu Asp Ser Pro Gln Leu Ser Gln Val His Gly Val Ile Gln Val
    770                 775                 780

Asp Val Ala Pro Ala Pro Gly Asp Gly Phe Phe Ser Asp Ala Gly
785                 790                 795                 800

Gly Asp Ser His Leu Gly Glu Thr Ile Pro Met Ala Ser Arg Gly Gly
                805                 810                 815

Ala
```

<210> SEQ ID NO 6
<211> LENGTH: 815
<212> TYPE: PRT
<213> ORGANISM: Mus musculus

<400> SEQUENCE: 6

```
Met Glu Gly Pro Arg Ser Asp Val Gly Arg Trp Gly Arg Ser Pro Trp
1               5                   10                  15
```

-continued

```
Gln Pro Pro Thr Thr Pro Ser Pro Glu Pro Glu Pro Glu Pro
             20              25              30
Asp Arg Arg Ser Arg Ser Arg Arg Gly Gly Gly Arg Ser Phe Trp Ala
         35              40              45
Arg Cys Cys Gly Cys Cys Ser Cys Gly Asn Arg Gly Asp Asp Asp Trp
     50              55              60
Gly Pro Glu Pro Ser Gly Ser Arg Ser Arg Gly Thr Ser Ser Arg Gly
 65              70              75              80
Arg Asp Ser Arg Gly Gly Arg Arg Pro Glu Ser Arg Gly Ser Gly Val
             85              90              95
Asn Ala Ala Gly Asp Gly Thr Ile Arg Glu Gly Met Leu Val Val Thr
         100             105             110
Gly Val Asp Leu Leu Cys Ser Arg Ser Asp Gln Asn Arg Arg Glu His
     115             120             125
His Thr Asp Glu Phe Glu Tyr Asp Glu Leu Ile Val Arg Arg Gly Gln
130             135             140
Pro Phe His Met Ile Leu Phe Leu Asn Arg Glu Tyr Glu Ser Ser Asp
145             150             155             160
Arg Ile Ala Leu Glu Leu Leu Ile Gly Ser Asn Pro Glu Val Gly Lys
             165             170             175
Gly Thr His Val Ile Ile Pro Val Gly Lys Gly Gly Ser Gly Gly Trp
         180             185             190
Lys Ala Gln Val Thr Lys Asn Asn Gly His Asn Leu Asn Leu Arg Val
     195             200             205
His Thr Ser Pro Asn Ala Ile Ile Gly Lys Phe Gln Phe Thr Val Arg
210             215             220
Thr Arg Ser Glu Ala Gly Glu Phe Gln Leu Pro Phe Asp Pro Arg Asn
225             230             235             240
Glu Ile Tyr Ile Leu Phe Asn Pro Trp Cys Pro Glu Asp Ile Val Tyr
             245             250             255
Val Asp His Glu Asp Trp Arg Gln Glu Tyr Val Leu Asn Glu Ser Gly
         260             265             270
Arg Ile Tyr Tyr Gly Thr Glu Ala Gln Ile Gly Glu Arg Thr Trp Asn
     275             280             285
Tyr Gly Gln Phe Asp His Gly Val Leu Asp Ala Cys Leu Tyr Ile Leu
290             295             300
Asp Arg Arg Gly Met Pro Tyr Gly Gly Arg Gly Asp Pro Val Ser Val
305             310             315             320
Ser Arg Val Val Ser Ala Met Val Asn Ser Leu Asp Asp Asn Gly Val
             325             330             335
Leu Ile Gly Asn Trp Thr Gly Asp Tyr Ser Arg Gly Thr Asn Pro Ser
         340             345             350
Ala Trp Val Gly Ser Val Glu Ile Leu Leu Ser Tyr Leu Arg Thr Gly
     355             360             365
Tyr Ser Val Pro Tyr Gly Gln Cys Trp Val Phe Ala Gly Val Thr Thr
370             375             380
Thr Val Leu Arg Cys Leu Gly Phe Ala Thr Arg Thr Val Thr Asn Phe
385             390             395             400
Asn Ser Ala His Asp Thr Asp Thr Ser Leu Thr Met Asp Ile Tyr Phe
             405             410             415
Asp Glu Asn Met Lys Pro Leu Glu His Leu Asn His Asp Ser Val Trp
         420             425             430
```

Asn Phe His Val Trp Asn Asp Cys Trp Met Lys Arg Pro Asp Leu Pro
            435                 440                 445

Ser Gly Phe Asp Gly Trp Gln Val Val Asp Ala Thr Pro Gln Glu Thr
450                 455                 460

Ser Ser Gly Ile Phe Cys Cys Gly Pro Cys Ser Val Glu Ser Val Lys
465                 470                 475                 480

Asn Gly Leu Val Tyr Met Lys Tyr Asp Thr Pro Phe Ile Phe Ala Glu
            485                 490                 495

Val Asn Ser Asp Lys Val Tyr Trp Gln Arg Gln Asp Asp Gly Ser Phe
            500                 505                 510

Lys Ile Val Tyr Val Glu Glu Lys Ala Ile Gly Thr Leu Ile Val Thr
            515                 520                 525

Lys Ala Ile His Ser Asn Asn Arg Glu Asp Ile Thr His Ile Tyr Lys
            530                 535                 540

His Pro Glu Gly Ser Glu Ala Glu Arg Arg Ala Val Glu Lys Ala Ala
545                 550                 555                 560

Ala His Gly Ser Lys Pro Asn Val Tyr Ala Thr Arg Asp Ser Ala Glu
            565                 570                 575

Asp Val Ala Met Gln Val Glu Ala Gln Asp Ala Val Met Gly Gln Asp
            580                 585                 590

Leu Ala Val Ser Val Val Leu Thr Asn Arg Gly Ser Ser Arg Arg Thr
            595                 600                 605

Val Lys Leu His Leu Tyr Leu Cys Val Thr Tyr Tyr Thr Gly Val Ser
            610                 615                 620

Gly Pro Thr Phe Lys Glu Ala Lys Lys Glu Val Thr Leu Ala Pro Gly
625                 630                 635                 640

Ala Ser Asp Ser Val Thr Met Pro Val Ala Tyr Lys Glu Tyr Lys Pro
            645                 650                 655

His Leu Val Asp Gln Gly Ala Met Leu Leu Asn Val Ser Gly His Val
            660                 665                 670

Lys Glu Ser Gly Gln Val Leu Ala Lys Gln His Thr Phe Arg Leu Arg
            675                 680                 685

Thr Pro Asp Leu Ser Leu Thr Leu Leu Gly Ala Ala Val Val Gly Gln
            690                 695                 700

Glu Cys Gly Val Gln Ile Val Phe Lys Asn Pro Leu Pro Val Thr Leu
705                 710                 715                 720

Thr Asn Val Val Phe Arg Leu Glu Gly Ser Gly Leu Gln Arg Pro Lys
            725                 730                 735

Val Leu Asn Val Gly Asp Ile Gly Gly Asn Glu Thr Val Thr Leu Arg
            740                 745                 750

Gln Thr Phe Val Pro Val Arg Pro Gly Pro Arg Gln Leu Ile Ala Ser
            755                 760                 765

Leu Asp Ser Pro Gln Leu Ser Gln Val His Gly Val Ile Gln Val Asp
            770                 775                 780

Val Ala Pro Ala Ser Gly Gly Ser Gly Phe Ser Asp Ala Gly Gly Asp
785                 790                 795                 800

Ser Arg Ser Gly Glu Asn Ile Pro Met Ala Tyr Arg Gly Gly Ala
            805                 810                 815

<210> SEQ ID NO 7
<211> LENGTH: 824
<212> TYPE: PRT
<213> ORGANISM: Rattus norvegicus -continued

```
<400> SEQUENCE: 7

Met Glu Gly Pro Arg Ser Asp Val Gly Arg Trp Gly Arg Ser Pro Trp
1               5                   10                  15

Gln Pro Thr Thr Pro Ser Pro Glu Pro Glu Pro Glu Pro Glu Pro Asp
            20                  25                  30

Arg Ser Arg Ser Arg Arg Gly Gly Arg Ser Phe Trp Ala Arg
        35                  40                  45

Cys Cys Gly Cys Cys Ser Cys Gly Asn Arg Ala Asp Asp Trp Gly
    50                  55                  60

Pro Glu Pro Ser Gly Ser Arg Ser Arg Gly Thr Ser Ser Arg Gly Gly
65                  70                  75                  80

Gly Ser Arg Gly Gly Asp Ser Arg Gly Arg Asp Ser Arg Gly Gly Arg
                85                  90                  95

Arg Pro Glu Ser Arg Gly Ser Gly Val Asn Ala Ala Gly Asp Gly Thr
            100                 105                 110

Ile Arg Glu Gly Met Leu Val Val Asn Gly Val Asp Leu Leu Cys Ser
        115                 120                 125

Arg Ser Asp Gln Asn Arg Arg Glu His His Thr Asp Glu Phe Glu Tyr
    130                 135                 140

Asp Glu Leu Ile Leu Arg Arg Gly Gln Pro Phe His Ile Ile Leu Phe
145                 150                 155                 160

Leu Asn Arg Glu Tyr Glu Ser Ser Asp Arg Ile Ala Leu Glu Leu Leu
                165                 170                 175

Ile Gly Asn Asn Pro Glu Val Gly Lys Gly Thr His Val Ile Ile Pro
            180                 185                 190

Val Gly Lys Gly Gly Ser Gly Gly Trp Lys Ala Gln Val Thr Lys Thr
        195                 200                 205

Asn Gly His Asn Leu Thr Leu Arg Val His Thr Ser Pro Asn Ala Ile
    210                 215                 220

Ile Gly Lys Phe Gln Phe Thr Val Arg Thr Arg Ser Glu Ala Gly Glu
225                 230                 235                 240

Phe Gln Leu Pro Phe Asp Pro Arg Asn Glu Ile Tyr Ile Leu Phe Asn
                245                 250                 255

Pro Trp Cys Pro Glu Asp Ile Val Tyr Val Asp His Glu Asp Trp Arg
            260                 265                 270

Gln Glu Tyr Val Leu Asn Glu Ser Gly Arg Ile Tyr Tyr Gly Thr Glu
        275                 280                 285

Ala Gln Ile Gly Glu Arg Thr Trp Asn Tyr Gly Gln Phe Asp His Gly
    290                 295                 300

Val Leu Asp Ala Cys Leu Tyr Ile Leu Asp Arg Arg Gly Met Pro Tyr
305                 310                 315                 320

Gly Gly Arg Gly Asp Pro Val Ser Val Ser Arg Val Val Ser Ala Met
                325                 330                 335

Val Asn Ser Leu Asp Asp Asn Gly Val Leu Ile Gly Asn Trp Thr Gly
            340                 345                 350

Asp Tyr Ser Arg Gly Thr Asn Pro Ser Ala Trp Val Gly Ser Val Glu
        355                 360                 365

Ile Leu Leu Ser Tyr Leu Arg Thr Gly Tyr Ser Val Pro Tyr Gly Gln
    370                 375                 380

Cys Trp Val Phe Ala Gly Val Thr Thr Thr Val Leu Arg Cys Leu Gly
385                 390                 395                 400

Leu Ala Thr Arg Thr Val Thr Asn Phe Asn Ser Ala His Asp Thr Asp
                405                 410                 415
```

-continued

Thr Ser Leu Thr Met Asp Ile Tyr Phe Asp Glu Asn Met Lys Pro Leu
            420                 425                 430

Glu His Leu Asn His Asp Ser Val Trp Asn Phe His Val Trp Asn Asp
            435                 440                 445

Cys Trp Met Lys Arg Pro Asp Leu Pro Ser Gly Phe Asp Gly Trp Gln
            450                 455                 460

Val Val Asp Ala Thr Pro Gln Glu Thr Ser Ser Gly Ile Phe Cys Cys
465                 470                 475                 480

Gly Pro Cys Ser Val Glu Ser Ile Lys Asn Gly Leu Val Tyr Met Lys
                    485                 490                 495

Tyr Asp Thr Pro Phe Ile Phe Ala Glu Val Asn Ser Lys Val Tyr
            500                 505                 510

Trp Gln Arg Gln Asp Asp Gly Ser Phe Lys Ile Val Tyr Val Glu Glu
            515                 520                 525

Lys Ala Ile Gly Thr Leu Ile Val Thr Lys Ala Ile Asn Ser Asn Met
            530                 535                 540

Arg Glu Asp Ile Thr His Ile Tyr Lys His Pro Glu Gly Ser Glu Ala
545                 550                 555                 560

Glu Arg Lys Ala Val Glu Lys Ala Ala His Gly Ser Lys Pro Asn
                    565                 570                 575

Val Tyr Ala Thr Arg Asp Ser Ala Glu Asp Val Ala Met Gln Val Glu
            580                 585                 590

Ala Gln Asp Ala Val Met Gly Gln Asp Leu Thr Val Ser Val Val Leu
            595                 600                 605

Thr Asn Arg Gly Ser Ser Arg Arg Thr Val Lys Leu His Leu Tyr Leu
            610                 615                 620

Cys Val Thr Tyr Tyr Thr Gly Val Ser Gly Pro Thr Phe Lys Glu Thr
625                 630                 635                 640

Lys Lys Glu Val Val Leu Ala Pro Gly Ala Ser Asp Thr Val Ala Met
                    645                 650                 655

Pro Val Ala Tyr Lys Glu Tyr Lys Pro His Leu Val Asp Gln Gly Ala
            660                 665                 670

Met Leu Leu Asn Val Ser Gly His Val Lys Glu Ser Gly Gln Val Leu
            675                 680                 685

Ala Lys Gln His Thr Phe Arg Leu Arg Thr Pro Asp Leu Ser Leu Thr
            690                 695                 700

Leu Leu Gly Ala Ala Val Val Gly Gln Glu Cys Glu Val Gln Ile Val
705                 710                 715                 720

Phe Lys Asn Pro Leu Pro Ile Thr Leu Thr Asn Val Val Phe Arg Leu
                    725                 730                 735

Glu Gly Ser Gly Leu Gln Arg Pro Lys Val Leu Asn Val Gly Asp Ile
            740                 745                 750

Gly Gly Asn Glu Thr Val Thr Leu Arg Gln Thr Phe Val Pro Val Arg
            755                 760                 765

Pro Gly Pro Arg Gln Leu Ile Ala Ser Leu Asp Ser Pro Gln Leu Ser
            770                 775                 780

Gln Val His Gly Val Ile Gln Val Asp Val Ala Pro Ser Ser Gly Gly
785                 790                 795                 800

Arg Gly Phe Ser Glu Ala Val Gly Asp Ser Arg Ser Gly Glu Asn Ile
                    805                 810                 815

Pro Met Ala Phe Arg Gly Gly Ala
            820

<210> SEQ ID NO 8
<211> LENGTH: 818
<212> TYPE: PRT
<213> ORGANISM: Pan troglodytes

<400> SEQUENCE: 8

```
Met Met Asp Gly Pro Arg Ser Asp Val Gly Arg Trp Gly Gly Asn Pro
1               5                   10                  15

Leu Gln Pro Pro Thr Thr Pro Ser Pro Glu Pro Glu Pro Glu Pro Asp
            20                  25                  30

Gly Arg Ser Arg Arg Gly Gly Gly Arg Ser Phe Trp Ala Arg Cys
        35                  40                  45

Cys Gly Cys Cys Ser Cys Arg Asn Ala Ala Asp Asp Asp Trp Gly Pro
    50                  55                  60

Glu Pro Ser Asp Ser Arg Gly Arg Gly Ser Ser Ser Gly Thr Arg Arg
65                  70                  75                  80

Pro Gly Ser Arg Gly Ser Asp Ser Arg Arg Pro Val Ser Arg Gly Ser
                85                  90                  95

Gly Val Asn Ala Ala Gly Asp Gly Thr Ile Arg Glu Gly Met Leu Val
            100                 105                 110

Val Asn Gly Val Asp Leu Leu Ser Ser Arg Ser Asp Gln Asn Arg Arg
        115                 120                 125

Glu His His Thr Asp Glu Tyr Glu Tyr Asp Glu Leu Ile Val Arg Arg
    130                 135                 140

Gly Gln Pro Phe His Met Leu Leu Leu Ser Arg Thr Tyr Glu Ser
145                 150                 155                 160

Ser Asp Arg Ile Thr Leu Glu Leu Leu Ile Gly Asn Asn Pro Glu Val
                165                 170                 175

Gly Lys Gly Thr His Val Ile Ile Pro Val Gly Lys Gly Gly Ser Gly
            180                 185                 190

Gly Trp Lys Ala Gln Val Val Lys Ala Ser Gly Gln Asn Leu Asn Leu
        195                 200                 205

Arg Val His Thr Ser Pro Asn Ala Ile Ile Gly Lys Phe Gln Phe Thr
    210                 215                 220

Val Arg Thr Gln Ser Asp Ala Gly Glu Phe Gln Leu Pro Phe Asp Pro
225                 230                 235                 240

Arg Asn Glu Ile Tyr Ile Leu Phe Asn Pro Trp Cys Pro Glu Asp Ile
                245                 250                 255

Val Tyr Val Asp His Glu Asp Trp Arg Gln Glu Tyr Val Leu Asn Glu
            260                 265                 270

Ser Gly Arg Ile Tyr Tyr Gly Thr Glu Ala Gln Ile Gly Glu Arg Thr
        275                 280                 285

Trp Asn Tyr Gly Gln Phe Asp His Gly Val Leu Asp Ala Cys Leu Tyr
    290                 295                 300

Ile Leu Asp Arg Arg Gly Met Pro Tyr Gly Gly Arg Gly Asp Pro Val
305                 310                 315                 320

Ser Val Ser Arg Val Ile Ser Ala Met Val Asn Ser Leu Asp Asp Asn
                325                 330                 335

Gly Val Leu Ile Gly Asn Trp Ser Gly Asp Tyr Ser Arg Gly Thr Asn
            340                 345                 350

Pro Ser Ala Trp Val Gly Ser Val Glu Ile Leu Leu Ser Tyr Leu Arg
        355                 360                 365

Thr Gly Tyr Ser Val Pro Tyr Gly Gln Cys Trp Val Phe Ala Gly Val
    370                 375                 380
```

```
Thr Thr Thr Val Leu Arg Cys Leu Gly Leu Ala Thr Arg Thr Val Thr
385                 390                 395                 400

Asn Phe Asn Ser Ala His Asp Thr Asp Thr Ser Leu Thr Met Asp Ile
            405                 410                 415

Tyr Phe Asp Glu Asn Met Lys Pro Leu Glu His Leu Asn His Asp Ser
        420                 425                 430

Val Trp Asn Phe His Val Trp Asn Asp Cys Trp Met Lys Arg Pro Asp
    435                 440                 445

Leu Pro Ser Gly Phe Asp Gly Trp Gln Val Val Asp Ala Thr Pro Gln
450                 455                 460

Glu Thr Ser Ser Gly Ile Phe Cys Cys Gly Pro Cys Ser Val Glu Ser
465                 470                 475                 480

Ile Lys Asn Gly Leu Val Tyr Met Lys Tyr Asp Thr Pro Phe Ile Phe
            485                 490                 495

Ala Glu Val Asn Ser Asp Lys Val Tyr Trp Gln Arg Gln Asp Asp Gly
        500                 505                 510

Ser Phe Lys Ile Val Tyr Val Glu Glu Lys Ala Ile Gly Thr Leu Ile
    515                 520                 525

Val Thr Lys Ala Ile Ser Ser Asn Met Arg Glu Asp Ile Thr Tyr Leu
530                 535                 540

Tyr Lys His Pro Glu Gly Ser Asp Ala Glu Arg Lys Ala Val Glu Thr
545                 550                 555                 560

Ala Ala Ala His Gly Ser Lys Pro Asn Val Tyr Ala Asn Arg Gly Ser
            565                 570                 575

Ala Glu Asp Val Ala Met Gln Val Glu Ala Gln Asp Ala Val Met Gly
        580                 585                 590

Gln Asp Leu Met Val Ser Val Met Leu Thr Asn His Ser Ser Ser Arg
    595                 600                 605

Arg Thr Val Lys Leu His Leu Tyr Leu Ser Val Thr Phe Tyr Thr Gly
610                 615                 620

Val Ser Gly Thr Ile Phe Lys Glu Thr Lys Lys Glu Val Glu Leu Ala
625                 630                 635                 640

Pro Gly Ala Ser Asp Arg Val Thr Met Pro Val Ala Tyr Lys Glu Tyr
            645                 650                 655

Arg Pro His Leu Val Asp Gln Gly Ala Met Leu Leu Asn Val Ser Gly
        660                 665                 670

His Val Lys Glu Ser Gly Gln Val Leu Ala Lys Gln His Thr Phe Arg
    675                 680                 685

Leu Arg Thr Pro Asp Leu Ser Leu Thr Leu Leu Gly Ala Ala Val Val
690                 695                 700

Gly Gln Glu Cys Glu Val Gln Ile Val Phe Lys Asn Pro Leu Pro Val
705                 710                 715                 720

Thr Leu Thr Asn Val Val Phe Arg Leu Glu Gly Ser Gly Leu Gln Arg
            725                 730                 735

Pro Lys Ile Leu Asn Val Gly Asp Ile Gly Gly Asn Glu Thr Val Thr
        740                 745                 750

Leu Arg Gln Ser Phe Val Pro Val Arg Pro Gly Pro Arg Gln Leu Ile
    755                 760                 765

Ala Ser Leu Asp Ser Pro Gln Leu Ser Gln Val His Gly Val Ile Gln
770                 775                 780

Val Asp Val Ala Pro Ala Pro Gly Asp Gly Gly Phe Phe Ser Asp Ala
785                 790                 795                 800
```

```
Gly Gly Asp Ser His Leu Gly Glu Thr Ile Pro Met Ala Ser Arg Gly
                805                 810                 815

Gly Ala

<210> SEQ ID NO 9
<211> LENGTH: 836
<212> TYPE: PRT
<213> ORGANISM: Oryctolagus cuniculus

<400> SEQUENCE: 9

Met Asp Gly Pro Arg Ser Asp Met Gly Arg Ser Asp Val Ser Arg Ser
1               5                   10                  15

Asp Met Ser Arg Ser Asp Met Gly Arg Ser Asp Met Gly Arg Ser Asp
                20                  25                  30

Val Gly Arg Cys Gly Gly Gly Pro Leu Gln Pro Ser Ala Thr Pro Ser
            35                  40                  45

Pro Glu Pro Glu Pro Glu Pro Glu Pro Asp Arg Gly Ser Arg
        50                  55                  60

Ser Arg Gly Gly Arg Gly Arg Ser Phe Trp Ala Arg Cys Cys Gly Cys
65                  70                  75                  80

Cys Ser Cys Arg Asn Ala Ala Asp Asp Trp Gly Arg Glu Pro Ser
                85                  90                  95

Asp Ser Arg Asp Arg Gly Ser Ser Ser Arg Gly Gly Arg Pro Asp Ser
                100                 105                 110

Arg Gly Gly Gly Val Asn Ala Ala Gly Asp Gly Thr Ile Arg Glu Gly
            115                 120                 125

Met Leu Val Val Thr Gly Val Asp Leu Leu Ser Ser Arg Ser Asp Gln
130                 135                 140

Asn Arg Arg Glu His His Thr Asp Glu Phe Glu Tyr Glu Glu Leu Ile
145                 150                 155                 160

Val Arg Arg Gly Gln Pro Phe His Leu Val Leu Phe Leu Ser Arg Pro
                165                 170                 175

Tyr Glu Ser Ser Asp Arg Ile Ala Leu Glu Leu Gln Ile Gly Asn Asn
                180                 185                 190

Pro Glu Val Gly Lys Gly Thr His Val Ile Pro Val Gly Lys Gly
            195                 200                 205

Asn Ser Gly Gly Trp Lys Ala Gln Val Thr Lys Ala Ser Gly Gln Thr
210                 215                 220

Leu Asn Leu Arg Val His Ser Pro Ala Ser Ala Ile Ile Gly Lys Phe
225                 230                 235                 240

Gln Phe Thr Val Arg Thr Arg Thr Glu Ala Gly Glu Phe Gln Leu Pro
                245                 250                 255

Phe Asp Pro Arg Asn Glu Ile Tyr Ile Leu Phe Asn Pro Trp Cys Pro
                260                 265                 270

Glu Asp Ile Val Tyr Val Asp His Glu Asp Trp Arg Gln Asp Tyr Val
            275                 280                 285

Leu Asn Glu Ser Gly Arg Ile Tyr Tyr Gly Thr Glu Ala Gln Ile Gly
        290                 295                 300

Glu Arg Thr Trp Asn Tyr Gly Gln Phe Asp His Gly Val Leu Asp Ala
305                 310                 315                 320

Cys Leu Tyr Ile Leu Asp Arg Arg Gly Met Pro Tyr Gly Gly Arg Gly
                325                 330                 335

Asp Pro Val Ser Val Ser Arg Val Ile Ser Ala Met Val Asn Ser Leu
            340                 345                 350
```

```
Asp Asp Asn Gly Val Leu Ile Gly Asn Trp Ser Gly Asp Tyr Ser Arg
        355                 360                 365

Gly Thr Asn Pro Ser Ala Trp Val Gly Ser Val Glu Ile Leu Leu Ser
370                 375                 380

Tyr Leu Arg Thr Gly Tyr Ser Val Pro Tyr Gly Gln Cys Trp Val Phe
385                 390                 395                 400

Ala Gly Val Thr Thr Thr Val Leu Arg Cys Leu Gly Leu Ala Thr Arg
                405                 410                 415

Thr Val Thr Asn Phe Asn Ser Ala His Asp Thr Asp Thr Ser Leu Thr
            420                 425                 430

Met Asp Ile Tyr Phe Asp Glu Asn Met Lys Pro Leu Glu His Leu Asn
        435                 440                 445

Arg Asp Ser Val Trp Asn Phe His Val Trp Asn Asp Cys Trp Met Lys
    450                 455                 460

Arg Pro Asp Leu Pro Ser Gly Phe Asp Gly Trp Gln Val Val Asp Ala
465                 470                 475                 480

Thr Pro Gln Glu Thr Ser Ser Gly Ile Phe Cys Cys Gly Pro Cys Ser
                485                 490                 495

Val Glu Ser Val Lys Asn Gly Leu Val Tyr Met Lys Tyr Asp Thr Pro
            500                 505                 510

Phe Ile Phe Ala Glu Val Asn Ser Asp Lys Val Tyr Trp Gln Arg Gln
        515                 520                 525

Asp Asp Gly Ser Phe Lys Ile Val Tyr Val Glu Glu Lys Ala Ile Gly
    530                 535                 540

Thr Leu Ile Val Thr Lys Ala Val Arg Ser His Met Arg Glu Asp Ile
545                 550                 555                 560

Thr His Ile Tyr Lys His Pro Glu Gly Ser Asp Ala Glu Arg Lys Ala
                565                 570                 575

Val Glu Thr Ala Ala His Gly Ser Lys Pro Asn Val Tyr Asp Ser
            580                 585                 590

Arg Asp Ser Ala Glu Asp Val Ala Met Gln Val Glu Ala Gln Asp Ala
        595                 600                 605

Val Met Gly Gln Asp Leu Thr Val Ser Val Leu Thr Asn Arg Ser
    610                 615                 620

Ser Ser Arg Arg Thr Val Lys Leu His Leu Tyr Leu Ser Val Thr Phe
625                 630                 635                 640

Tyr Thr Gly Val Thr Gly Ser Ile Phe Lys Glu Ser Lys Lys Glu Val
                645                 650                 655

Val Leu Ala Ala Gly Ser Ser Asp Ser Val Val Met Pro Val Ala Tyr
            660                 665                 670

Lys Glu Tyr Arg Pro His Leu Val Asp Gln Gly Ala Met Leu Leu Asn
        675                 680                 685

Val Ser Gly His Val Lys Glu Ser Gly Gln Val Leu Ala Lys Gln His
    690                 695                 700

Thr Phe Arg Val Arg Thr Pro Asp Leu Ser Leu Thr Leu Leu Gly Ala
705                 710                 715                 720

Ala Val Val Gly Gln Glu Cys Glu Val Gln Ile Val Phe Arg Asn Pro
                725                 730                 735

Leu Pro Ile Thr Leu Thr Asn Val Val Phe Arg Leu Glu Gly Ser Gly
            740                 745                 750

Leu Gln Arg Pro Lys Ile Leu Asn Val Gly Asp Ile Gly Gly Asn Glu
        755                 760                 765
```

Thr Val Thr Leu Arg Gln Thr Phe Val Pro Val Arg Pro Gly Pro Arg
    770                 775                 780

Gln Leu Ile Ala Ser Leu Asp Ser Pro Gln Leu Ser Gln Val His Gly
785                 790                 795                 800

Val Ile Gln Val Asp Val Ala Pro Ala Ser Gly Gly Arg Gly Phe Leu
                805                 810                 815

His Ala Gly Gly Asp Ser Tyr Ser Gly Glu Thr Ile Pro Met Thr Ser
            820                 825                 830

Arg Gly Glu Ala
        835

<210> SEQ ID NO 10
<211> LENGTH: 815
<212> TYPE: PRT
<213> ORGANISM: Canis lupus familiaris

<400> SEQUENCE: 10

Met Asp Gly Pro Arg Ser Asp Val Gly Arg Trp Gly Gly Asn Pro Trp
1               5                   10                  15

Gln Pro Pro Thr Thr Pro Ser Pro Glu Pro Glu Pro Glu Pro Glu Pro
                20                  25                  30

Glu Arg Arg Ser Arg Arg Gly Gly Arg Ser Phe Trp Ala Arg Cys Cys
            35                  40                  45

Gly Cys Cys Ser Cys Arg Asn Arg Ala Asp Asp Trp Gly Pro Glu
    50                  55                  60

Pro His Arg Asp Arg Gly Ser Gly Ser Gly Arg Arg Arg Pro Asp Ser
65                  70                  75                  80

Arg Gly Ser Asp Ser Arg Arg Pro Gly Ser Arg Ala Ser Gly Val Asn
                85                  90                  95

Ala Ala Gly Asp Gly Thr Ile Arg Glu Gly Met Leu Val Val Thr Gly
            100                 105                 110

Val Asp Leu Leu Ser Ser Arg Ser Asp Gln Asn Arg Arg Glu His His
        115                 120                 125

Thr Asp Glu Phe Glu Tyr Asp Glu Leu Ile Ile Arg Arg Gly Gln Pro
    130                 135                 140

Phe His Met Val Leu His Phe Ser Arg Pro Tyr Glu Ser Ser Asp Arg
145                 150                 155                 160

Val Ala Leu Glu Leu Leu Ile Gly Asn Asn Pro Glu Val Gly Lys Gly
                165                 170                 175

Thr His Val Ile Ile Pro Val Gly Lys Gly Ser Gly Gly Trp Lys
            180                 185                 190

Ala Gln Val Thr Lys Ala Ser Gly Gln Asn Leu Asn Leu Arg Val His
        195                 200                 205

Thr Ser Pro Asn Ala Ile Ile Gly Lys Phe Gln Phe Thr Val Arg Thr
    210                 215                 220

His Ser Glu Ala Gly Glu Phe Gln Leu Pro Phe Asp Pro His Asn Glu
225                 230                 235                 240

Ile Tyr Ile Leu Phe Asn Pro Trp Cys Pro Glu Asp Ile Val Tyr Val
                245                 250                 255

Asp His Glu Asp Trp Arg Gln Glu Tyr Val Leu Asn Glu Ser Gly Arg
            260                 265                 270

Ile Tyr Tyr Gly Thr Glu Ala Gln Ile Gly Glu Arg Thr Trp Asn Tyr
        275                 280                 285

```
Gly Gln Phe Asp His Gly Val Leu Asp Ala Cys Leu Tyr Ile Leu Asp
    290                 295                 300

Arg Arg Gly Met Pro Tyr Gly Gly Arg Gly Asp Pro Val Ser Val Ser
305                 310                 315                 320

Arg Val Ile Ser Ala Met Val Asn Ser Leu Asp Asp Asn Gly Val Leu
                325                 330                 335

Ile Gly Asn Trp Ser Gly Asp Tyr Ser Arg Gly Thr Asn Pro Ser Ala
            340                 345                 350

Trp Val Gly Ser Val Glu Ile Leu Leu Ser Tyr Leu Arg Thr Gly Tyr
        355                 360                 365

Ser Val Pro Tyr Gly Gln Cys Trp Val Phe Ala Gly Val Thr Thr Thr
370                 375                 380

Val Leu Arg Cys Leu Gly Leu Ala Thr Arg Thr Val Thr Asn Phe Asn
385                 390                 395                 400

Ser Ala His Asp Thr Asp Thr Ser Leu Thr Met Asp Ile Tyr Phe Asp
                405                 410                 415

Glu Asn Met Lys Pro Leu Glu His Leu Asn His Asp Ser Val Trp Asn
            420                 425                 430

Phe His Val Trp Asn Asp Cys Trp Met Lys Arg Pro Asp Leu Pro Ser
        435                 440                 445

Gly Phe Asp Gly Trp Gln Val Val Asp Ala Thr Pro Gln Glu Thr Ser
450                 455                 460

Ser Gly Ile Phe Cys Cys Gly Pro Cys Ser Val Glu Ser Ile Lys Asn
465                 470                 475                 480

Gly Leu Val Tyr Met Lys Tyr Asp Thr Pro Phe Ile Phe Ala Glu Val
                485                 490                 495

Asn Ser Asp Lys Val Tyr Trp Gln Arg Gln Asp Asp Gly Ser Phe Lys
            500                 505                 510

Ile Val Tyr Val Glu Glu Lys Ala Ile Gly Thr Leu Ile Val Thr Lys
        515                 520                 525

Ala Val Gly Ser Asn Met Gln Asp Asp Val Thr His Ile Tyr Lys His
530                 535                 540

Pro Glu Gly Ser Glu Ala Glu Arg Lys Ala Val Glu Thr Ala Ala Ala
545                 550                 555                 560

His Gly Ser Lys Pro Asn Val Tyr Thr Asn Arg Asp Ser Ala Glu Asp
                565                 570                 575

Val Ala Leu Gln Val Glu Ala Gln Asp Ala Val Met Gly Gln Asp Leu
            580                 585                 590

Thr Val Ser Val Val Leu Thr Asn Arg Gly Ser Ser Thr Arg Thr Val
        595                 600                 605

Lys Leu His Leu Tyr Leu Ser Val Thr Phe Tyr Thr Gly Val Thr Gly
610                 615                 620

Pro Val Phe Lys Glu Ser Lys Lys Glu Val Val Leu Ala Pro Gly Ala
625                 630                 635                 640

Thr Glu Arg Val Ser Met Pro Val Ala Tyr Lys Glu Tyr Arg Pro Gln
                645                 650                 655

Ile Val Asp Gln Gly Ser Met Leu Leu Asn Val Ser Gly His Val Lys
            660                 665                 670

Glu Asn Gly Gln Val Leu Ala Lys Gln His Thr Phe Arg Leu Arg Thr
        675                 680                 685

Pro Asp Leu Ser Leu Thr Leu Leu Gly Ala Ala Val Val Gly Gln Glu
690                 695                 700
```

-continued

| | | | | | | | | | | | | | | |
|---|---|---|---|---|---|---|---|---|---|---|---|---|---|---|
| Cys | Glu | Val | Gln | Ile | Val | Phe | Lys | Asn | Pro | Leu | Pro | Val | Thr | Leu | Thr |
| 705 | | | | | 710 | | | | | 715 | | | | | 720 |
| Asn | Val | Val | Phe | Arg | Leu | Glu | Gly | Ser | Gly | Leu | Gln | Arg | Pro | Lys | Ile |
| | | | | 725 | | | | | 730 | | | | | 735 | |
| Leu | Asn | Val | Gly | Asp | Ile | Gly | Gly | Asn | Glu | Thr | Val | Thr | Leu | His | Gln |
| | | | 740 | | | | | 745 | | | | | 750 | | |
| Lys | Phe | Val | Pro | Val | Arg | Pro | Gly | Pro | Arg | Gln | Leu | Ile | Ala | Ser | Leu |
| | | 755 | | | | | 760 | | | | | 765 | | | |
| Asp | Ser | Pro | Gln | Leu | Ser | Gln | Val | His | Gly | Val | Ile | Gln | Val | Asp | Val |
| | 770 | | | | | 775 | | | | | 780 | | | | |
| Ala | Pro | Ala | Pro | Gly | Gly | Gly | Phe | Phe | Ser | Asn | Ala | Gly | Gly | Asn | |
| 785 | | | | | 790 | | | | | 795 | | | | | 800 |
| Ser | Pro | Leu | Gly | Glu | Thr | Ile | Pro | Met | Ala | Ser | Arg | Gly | Gly | Ala | |
| | | | | 805 | | | | | 810 | | | | | 815 | |